United States Patent
Nakasuji et al.

(10) Patent No.: US 6,593,152 B2
(45) Date of Patent: Jul. 15, 2003

(54) ELECTRON BEAM APPARATUS AND METHOD OF MANUFACTURING SEMICONDUCTOR DEVICE USING THE APPARATUS

(75) Inventors: Mamoru Nakasuji, Kanagawa (JP); Tohru Satake, Kanagawa (JP); Kenji Watanabe, Kanagawa (JP); Takeshi Murakami, Tokyo (JP); Nobuharu Noji, Kanagawa (JP); Hirosi Sobukawa, Kanagawa (JP); Tsutomu Karimata, Kanagawa (JP); Shoji Yoshikawa, Tokyo (JP); Toshifumi Kimba, Kanagawa (JP); Shin Oowada, Kanagawa (JP); Mutsumi Saito, Kanagawa (JP); Muneki Hamashima, Saitama (JP); Toru Takagi, Kanagawa (JP); Naoto Kihara, Kanagawa (JP); Hiroshi Nishimura, Kanagawa (JP)

(73) Assignees: Ebara Corporation, Tokyo (JP); Nikon Corporation, Tokyo (JP)

(*) Notice: Subject to any disclaimer, the term of this patent is extended or adjusted under 35 U.S.C. 154(b) by 0 days.

(21) Appl. No.: 09/985,325

(22) Filed: Nov. 2, 2001

(65) Prior Publication Data

US 2002/0142496 A1 Oct. 3, 2002

(30) Foreign Application Priority Data

| Nov. 2, 2000 | (JP) | 2000/335833 |
| Nov. 2, 2000 | (JP) | 2000/336305 |
| Nov. 6, 2000 | (JP) | 2000/337370 |
| Nov. 6, 2000 | (JP) | 2000/337491 |
| Nov. 17, 2000 | (JP) | 2000/350935 |
| Nov. 20, 2000 | (JP) | 2000/352720 |
| Nov. 21, 2000 | (JP) | 2000/353831 |
| Nov. 22, 2000 | (JP) | 2000/355294 |
| Nov. 29, 2000 | (JP) | 2000/362752 |
| Nov. 30, 2000 | (JP) | 2000/364556 |
| Jan. 12, 2001 | (JP) | 2001/005140 |
| Feb. 8, 2001 | (JP) | 2001/031901 |
| Feb. 8, 2001 | (JP) | 2001/031906 |
| Feb. 9, 2001 | (JP) | 2001/033599 |
| Apr. 5, 2001 | (JP) | 2001/106656 |
| May 2, 2001 | (JP) | 2001/134981 |
| May 28, 2001 | (JP) | 2001/158571 |

(51) Int. Cl.$^7$ ............ H01L 21/66; G01N 23/00
(52) U.S. Cl. ............ 438/14; 250/310; 250/492.3
(58) Field of Search ............ 438/14, 15, 16, 438/17, 18; 250/306, 307, 310, 311, 492.1, 492.2, 492.3

(56) References Cited

U.S. PATENT DOCUMENTS

| 4,726,689 A | 2/1988 | Pollock ............ 384/12 |
| 4,912,052 A | 3/1990 | Miyoshi et al. ............ 324/751 |
| 5,359,197 A | 10/1994 | Komatsu et al. ............ 250/310 |
| 5,892,224 A | 4/1999 | Nakasuji ............ 250/310 |
| 5,981,947 A | 11/1999 | Nakasuji et al. ............ 250/310 |
| 6,087,667 A | 7/2000 | Nakasuji et al. ............ 250/492.2 |
| 6,125,522 A | 10/2000 | Nakasuji ............ 29/458 |
| 2002/0015143 A1 * | 2/2002 | Yin et al. ............ 355/133 |

OTHER PUBLICATIONS

Electron Ion Beam Handbook, pp. 115–119 (1988) with partial translation.

(List continued on next page.)

*Primary Examiner*—Evan Pert
(74) *Attorney, Agent, or Firm*—Armstrong, Westerman & Hattori, LLP

(57) ABSTRACT

The present invention provides an electron beam apparatus for evaluating a sample surface, which has a primary electro-optical system for irradiating a sample with a primary electron beam, a detecting system, and a secondary electro-optical system for directing secondary electron beams emitted from the sample surface by the irradiation of the primary electron beam to the detecting system.

60 Claims, 47 Drawing Sheets

OTHER PUBLICATIONS

B. Lischke et al., Japanese Journal of Applies Physics, vol. 28, No. 10, pp. 2058–2064, 1989.

P. Sandland et al., "An Electron Beam Inspection Sytem for X–ray Mask Production," Journal of Vacuum Science and Technology, vol. 9, No. 6, 1991, pp. 3005–3009.

W.D. Meisburger et al., "Requirements and Performance of an Electron Beam Column Designed for X–ray Mask Inspection," Journal of Vacuum Science and Technology, vol. 9, No. 6, 1991, pp. 3010–3014.

U.S. patent application Ser. No. 09/985,323, filed Nov. 2, 2001, Mamoru Nakasuji et al., Electron Beam Apparatus and device Production Method Using the Electron Beam Apparatus.

U.S. patent application Ser. No. 09/985,324, filed Nov. 2, 2001, Toshifumi Kimba et al., "Apparatus for Inspecting Material with Electron Beam, Method for Operating Same and Method for Manufacturing Semiconductor Device Using Former".

U.S. patent application Ser. No. 09/985,322, filed Nov. 2, 2001, Mamoru Nakasuji et al., "Electron Beam Apparatus and Method of Manufacturing Semiconductor Device Using the Apparatus".

U.S. patent application Ser. No. 09/985,331, filed Nov. 2, 2001, Mamoru Nakasuji et al., "Method for Inspecting Substrate, Substrate Inspecting System and Electron Beam Apparatus".

* cited by examiner

ELECTRON BEAM APPARATUS AND METHOD OF MANUFACTURING SEMICONDUCTOR DEVICE USING THE APPARATUS

BACKGROUND OF THE INVENTION

The present invention relates to a technique for testing or inspecting a property or aspect of a sample such as a wafer. In more detail, the present invention relates to an electron beam apparatus applicable to a defect detection and/or line width measurement of a wafer during a semiconductor manufacturing process and so on, in which electron beams are irradiated to a sample, secondary electrons emitted from the sample and varying according to a property of the sample surface are captured, and image data is created therefrom to evaluate patterns on the sample surface with a high throughput on the basis of the image data. The present invention also relates to an evaluation system and a semiconductor device manufacturing method, both of which utilize the electron beam apparatus. In the present description, the meaning of the term "evaluation" of a sample also includes the meaning of "inspection" such as defect detection and line width measurement of a sample.

In semiconductor processes, design rules are now going to enter the era of 100 nm, and the production scheme is shifting from small-kind mass production represented by DRAM to a multi-kind small production such as SOC (silicon on chip). Associated with this shifting, the number of manufacturing steps has been increased, and an improved yield of each process is essential, so that testing for defects caused by the process becomes important.

With the trend of increasingly higher integration of semiconductor devices and finer patterns, a need exists for high resolution, high throughput testing apparatuses. A resolution of 100 nm or less is required for examining defects on a wafer of 100 nm design rule. Also, as manufacturing steps are increased in response to the requirement of higher integration of devices, the amount of testing is increased and thus a higher throughput is required. Further, as devices are formed of an increased number of layers, testing apparatuses are required to have the ability to detect defective contacts (electric defect) of vias which connect lines on layers to each other. While optical defect testing apparatuses are mainly used at present, it is anticipated that electron beam based defect testing apparatuses will substitute for optical defect testing apparatus as a dominant testing apparatus in the future from a viewpoint of the resolution and defective contact testing capabilities. However, the electron beam based defect testing apparatus also has a disadvantage in that it is inferior to the optical one in the throughput. For this reason, a need exists for the development of a high resolution, high throughput electron beam based testing apparatus which is capable of electrically detecting defects.

It is said that the resolution of an optical defect testing apparatus is limited to one half of the wavelength of used light, and the limit is approximately 0.2 $\mu$m in an example of practically used optical defect detecting apparatus which uses visible light. On the other hand, in electron beam based systems, scanning electron microscopes (SEM) have been commercially available. The scanning electron microscope has a resolution of 0.1 $\mu$m and takes a testing time of eight hours per 20 cm wafer. The electron beam based system also has a significant feature that it is capable of testing electric defects (broken lines, defective conduction of lines, defective conduction of vias, and so on). However, it takes so long testing time that it is expected to develop a defect testing apparatus which can rapidly conduct a test. Further, a testing apparatus is expensive and low in throughput as compared with other process apparatuses, so that it is presently used after critical steps, such as after etching, deposition (including copper coating), CMP (chemical-mechanical polishing) planarization processing, and so on.

A testing apparatus in accordance with an electron beam based scanning (SEM) scheme will be described. An SEM based testing apparatus narrows down an electron beam which is linearly irradiated to a sample for scanning. The diameter of the electron beam corresponds to the resolution. On the other hand, by moving a stage in a direction perpendicular to a direction in which the electron beam is scanned, a region under observation is Two-dimensionally irradiated with the electron beam. In general, the width over which the electron beam is scanned, extends over several hundred $\mu$m. Secondary electron beams emitted from the sample by the irradiation of the focussed electron beam (called the "primary electron beam") are detected by a combination of a scintillator and a photomultiplier (photomultiplier tube) or a semiconductor based detector (using PIN diodes). The coordinates of irradiated positions and the amount of the secondary electron beams (signal strength) are combined to generate an image which is stored in a storage device or output on a CRT (Braun tube). The foregoing is the principle of SEM (scanning electron microscope). From an image generated by this system, defects on a semiconductor (generally, Si) wafer is detected in the middle-of a manufacturing procedure. A detecting speed corresponding to the throughput, is determined by the intensity of a primary electron beam (current value), a size of a pixel, and a response speed of a detector. Currently available maximum values are 0.1 $\mu$m for the beam diameter (which may be regarded as the same as the resolution), 100 nA for the current value of the primary electron beam, and 100 MHz for the response speed of the detector, in which case it is said that a testing speed is approximately eight hours per wafer of 20 cm diameter. Therefore, there exists a problem that a testing speed is significantly low in comparison with that in an optical based testing apparatus. For instance, the former testing speed is 1/20 or less of the latter testing speed.

If a beam current is increased in order to achieve a high throughput, a satisfactory SEM image cannot be obtained in the case of a wafer having an insulating membrane on its surface because charging occurs.

As another method for improving an inspection speed, in terms of which an SEM system is poor, there have been proposed SEM systems (multi-beam SEM systems) and apparatuses employing a plurality of electron beams. According to the systems and apparatuses, an inspection speed is improved in proportion to the number of electron beams. However, as a plurality of primary electron beams impinge obliquely on a wafer and a plurality of secondary electron beams are pulled from the wafer obliquely, only secondary electrons released obliquely from the wafer are caught by a detector. Further, a shadow occasionally appears on an image and secondary electrons from a plurality of electron beams are difficult to separate from one another, which disadvantageously results in a mix of the secondary electrons.

Still further, there has been no suggestion or consideration about an interaction between an electron beam apparatus and other sub-systems in an evaluation system employing a multi-beam based electron beam apparatus and thus, at present there aren't any complete evaluation systems of a high throughput. In the meantime, as a wafer to be inspected becomes greater, sub-systems must be re-designed to accommodate to a greater wafer, a solution for which has not yet been suggested either.

SUMMARY OF THE INVENTION

The present invention has been accomplished with a view to obviating the aforementioned problems of prior art and therefore, it is an object of the present invention to provide an evaluation system employing an SEM electron beam apparatus of a multi-beam type and especially an evaluation system capable of improving a throughput of inspection processing.

It is another object of the present invention to provide an SEM electron beam apparatus of a multi-beam type capable of improving not only a throughput of inspection processing but also detection accuracy.

It is still another object of the present invention to provide a method of manufacturing semiconductor devices, according to which a semiconductor wafer can be evaluated by utilizing such an electron beam apparatus or evaluation system as mentioned above irrespective of whether it is in the middle of a fabrication process or upon completion of a fabrication process.

In order to achieve the above objects, the present invention is constituted as follows. That is, a plurality of primary electron beams (multi-beam) are employed to scan a sample in the one-dimensional direction (X direction). The primary electron beams pass through an ExB filter (Wien filter) to impinge perpendicularly upon the surface of the sample, and secondary electrons released from the sample are separated from the primary electron beams by the ExB filter to be pulled obliquely in relation to the axis of the primary electron beams to converge or form an image on a detection system by means of a lens system. Then, a stage is moved in the perpendicular direction (Y direction) with respect to the primary electron beam scanning direction (X direction) to obtain continuous images.

When the primary electron beams pass through the ExB filter, a condition (Wien condition) where the force applied to the electron beams from the electrical field is equal to the force applied from the magnetic field and the directions of the forces are opposite, is set so that the primary electron beams go straight. On the other hand, since the secondary electrons and the primary electron beams advance in the opposite directions, the directions of the forces applied to the secondary electrons from the electrical field and magnetic field are the same and thus, the secondary electrons are deflected from the axial direction of the primary electron beams. As a result, the primary electron beams and secondary electron beams are separated from each other. When electron beams pass through an ExB filter, aberration is larger if the electron beams curve than if the electron beams travel straight. Given that, the optical system of the present invention is designed in such a manner as to cause primary electron beams, which require high accuracy, to go straight and cause secondary electron beams, which do not necessarily require high accuracy, to deflect.

A detection system of the present invention consists of detectors respectively corresponding to primary electron beams, which are arranged such that a secondary electron deriving from its corresponding primary electron beam impinges on the corresponding detector by means of an image-formation system, whereby interaction of signals, that is, cross-talk can be substantially reduced. As a detector, a combination of a scintillator and a photomultiplier, a PIN diode, etc. may be employed. In the electron beam apparatus according to one embodiment of the present invention, sixteen primary electron beams are employed and a beam current of 20 nA having a beam diameter of 0.1 $\mu$m is obtained from each of them and therefore, a value of current obtained from the sixteen electron beams in the electron beam apparatus is three times as great as that obtained from the commercially available apparatus at present.

Further, an electron gun for the electron beam apparatus of the present invention uses a thermal cathode as an electron beam source, and $LaB_6$ is employed as an electron emitting material (emitter). Other materials may be used as long as they have a high melting point (low steam pressure at high temperatures) and small work function. In the present invention, two different ways of providing multiple electron beams are employed. One is to pull one electron beam from an emitter (with one protrusion) and pass the electron beam through a thin plate with a plurality of apertures, thereby obtaining a plurality of electron beams. The other is to provide an emitter with a plurality of protrusions and pull a plurality of electron beams directly from the protrusions. The both ways make use of the properties of an electron beam that an electron beam is more easily emitted from the tip of a protrusion. Electron beams from an electron beam source employing other methods, for example, thermal field emission type electron beams may be employed. A thermal electron beam source uses a system for heating an electron emission material to emit electrons, whereas a thermal field emission electron beam source uses a system for applying a high electric field to an electron emission material to emit electrons and further heating an electron beam emission portion to stabilize electron emission.

BRIEF DESCRIPTION OF THE DRAWINGS

FIGS. 6A and 6B show an enlarged view of the wafer rack, in which FIG. 6A is a side view thereof and FIG. 6B is a cross section thereof taken along the line E—E in FIG. 6A;

FIGS. 12A and 12B illustrate an electron beam calibration mechanism applicable to the electron beam apparatus concerning the present invention, in which FIG. 12A is a side view thereof and FIG. 12B is a plan view thereof;

DETAILED DESCRIPTION OF THE INVENTION

In the following, embodiments of an evaluation system according to the present invention will be described in a case that evaluation samples are semiconductor substrates or wafers having patterns on surfaces thereof. It should be noted that samples other than the wafer are applicable.

Figure 1:
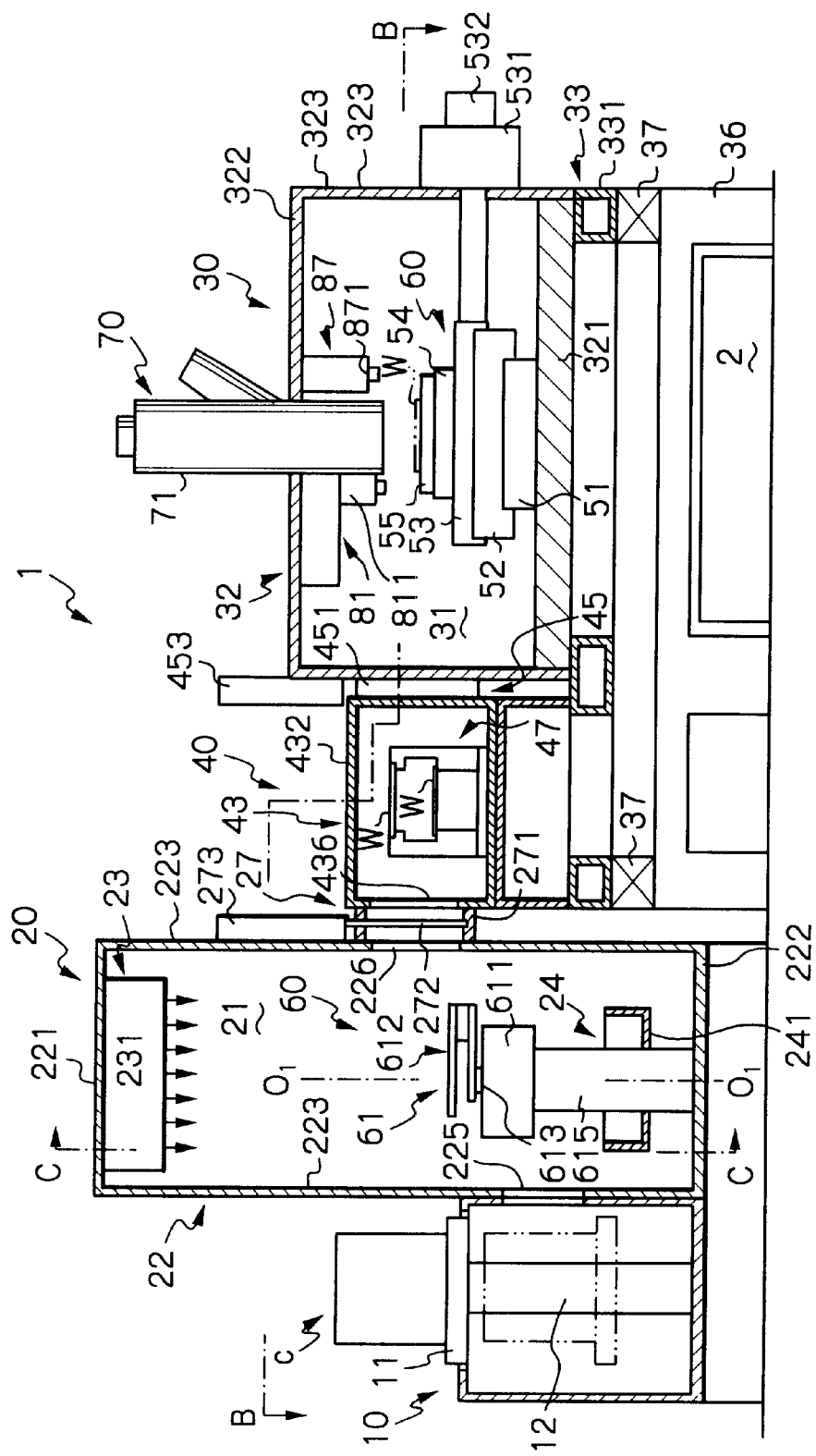
FIG. 1 is an elevation view illustrating major components of an evaluation system according to the present invention.
Figure 2:
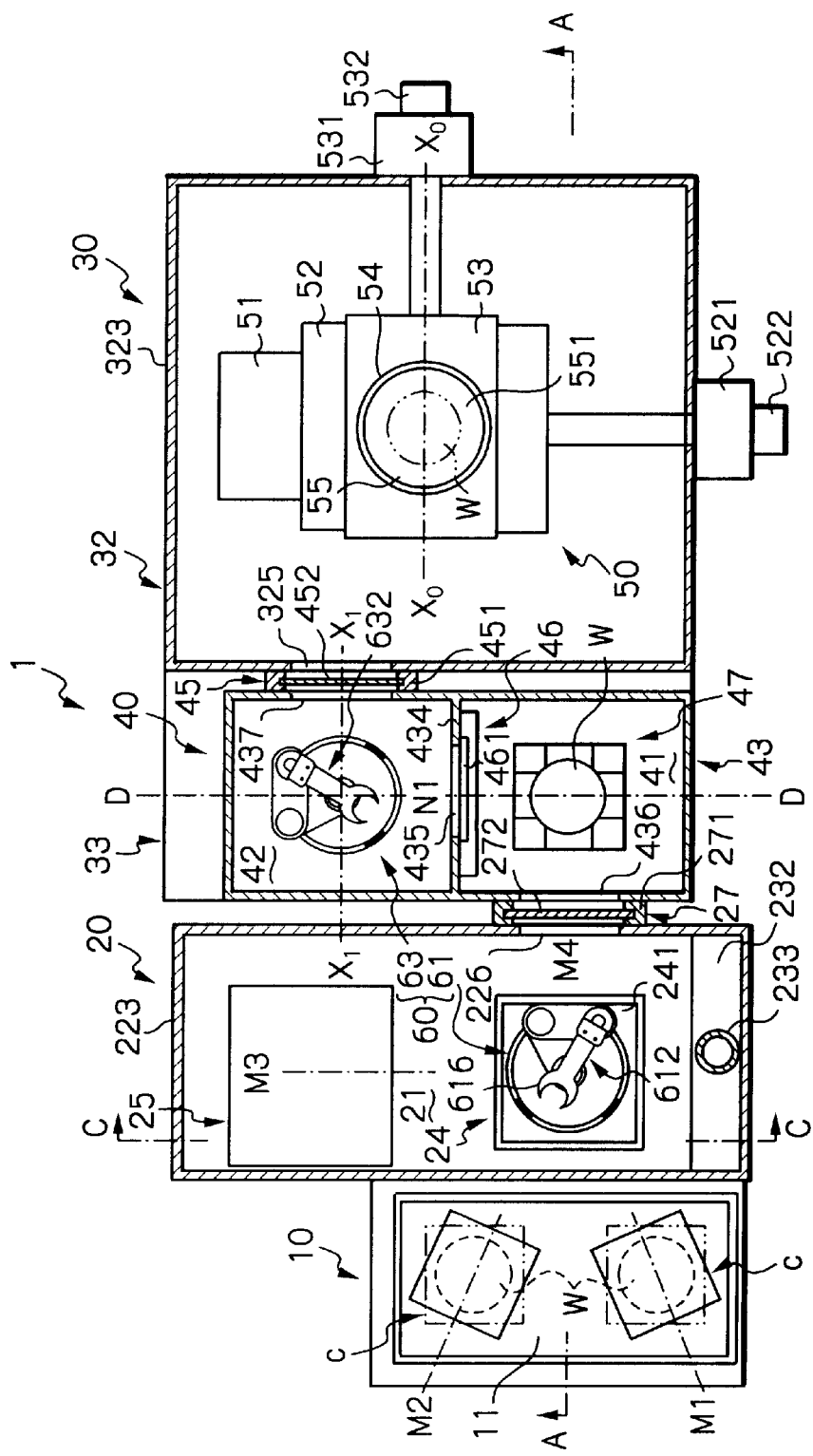
FIG. 2 is a plan view illustrating major components of the evaluation system indicated in FIG. 1 seen from above along the line in B—B in FIG. 1.

FIGS. 1 and 2 respectively shows a cross-sectional and plan views illustrating main components of evaluation system 1 according to an embodiment of the present invention. The evaluation system 1 comprises a cassette holder 10 for holding a cassette which stores a plurality of wafers; a mini-environment chamber 20; a main housing 30; a loader housing 40 disposed between the mini-environment chamber 20 and the main housing 30 to define two loading chambers; a loader 60 for loading a wafer from the cassette holder 10 (onto a stage apparatus 50 disposed in the main housing 30); the stage apparatus 50 for carrying and moving the wafer W; and an electro-optical system 70 installed in the vacuum main housing 30. These components are arranged in a positional relationship as illustrated in FIGS. 1 and 2. The evaluation system further comprises a pre-charge unit 81 disposed in the vacuum main housing 30; a potential applying mechanism 83 (see in FIG. 11) for applying a wafer with a potential; an electron beam calibration mechanism 85 (see in FIG. 12); and an optical microscope 871 which forms part of an alignment controller 87 for aligning the wafer on the stage apparatus 50.

Constitutions of the main components (sub-system) will next be explained in detail.

Cassette Holder 10

The cassette holder 10 is configured to hold a plurality (two in this embodiment) of cassettes c(for example, closed cassettes such as SMIF, FOUP manufactured by Assist Co.) in which a plurality (for example, twenty-five) wafers are placed side by side in parallel, oriented in the vertical direction. The cassette holder 10 can be arbitrarily selected for installation adapted to a particular loading mechanism. Specifically, when a cassette is automatically loaded into the cassette holder by a robot or the like, the cassette holder 10 having a structure adapted to the automatic loading can be installed. When a cassette is manually loaded into the cassette holder 10, the cassette holder 10 having an open cassette structure can be installed. In this embodiment, the cassette holder 10 is a type adapted to the automatic cassette loading, and comprises, for example, an up/down table 11, and an elevating mechanism 12 for moving the up/down table 11 up and down. The cassette ccan be automatically set onto the up/down table 11 in a state indicated by chain lines in FIG. 2. After the setting, the cassette cis automatically rotated to a state indicated by solid lines in FIG. 2 so that it is directed to the axis of pivotal movement of a first carrier unit within the mini-environment chamber 20. In addition, the up/down table 11 is moved down to a state indicated by chain lines in FIG. 1. In this way, since the cassette holder 10 for use in automatic loading, or the cassette holder 10 for use in manual loading may be both implemented by those in known structures, detailed description on their structures and functions are omitted.

Figure 3:
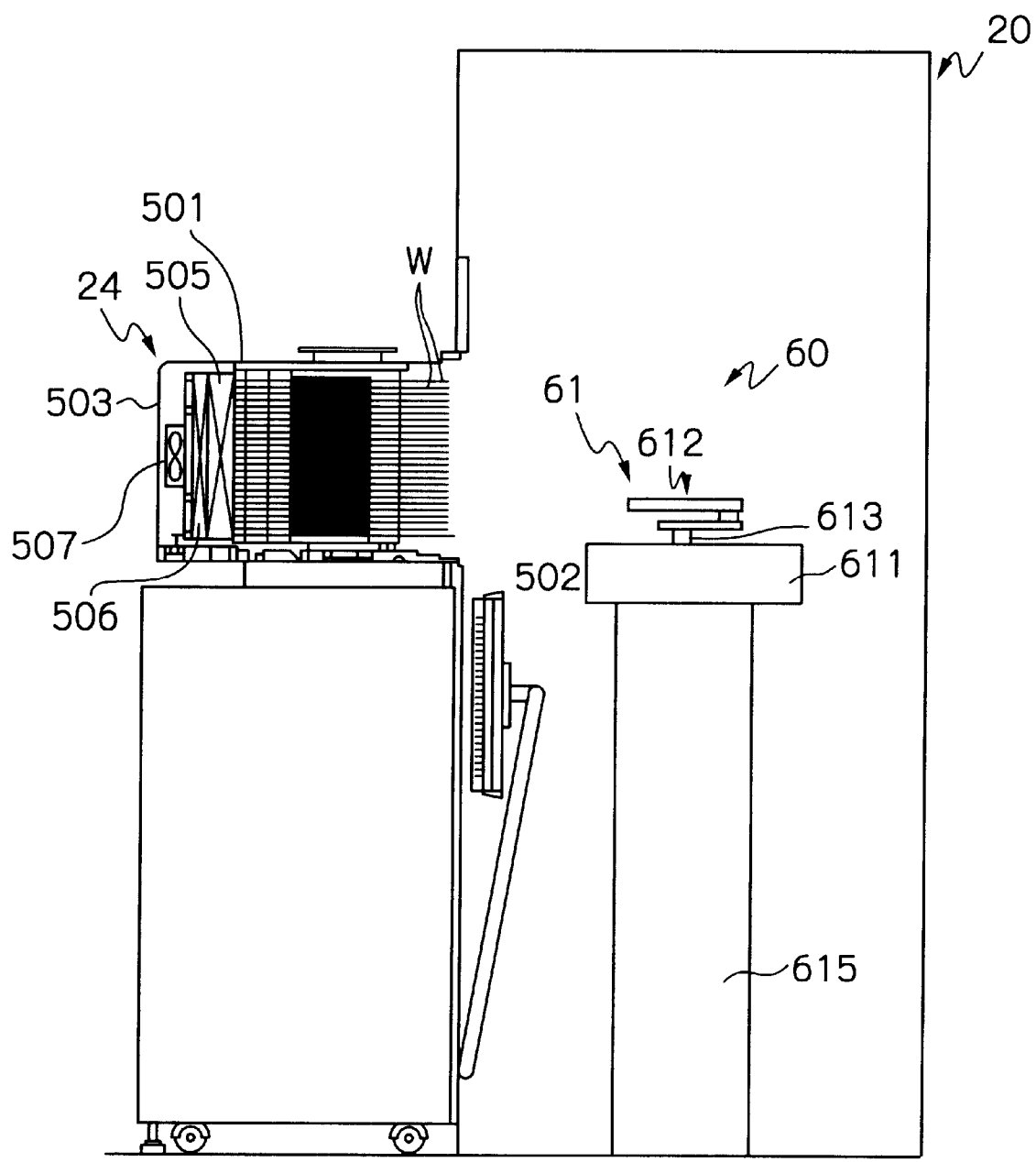
FIG. 3 illustrates a relationship between a wafer transfer chamber and a loader.

FIG. 3 shows a modification to a mechanism for automatically loading a cassette. A plurality of 300 mm wafers W are contained in a slotted pocket (not shown) fixed to the inner surface of a chamber 501 for carriage and storage. This wafer carrying section 24 comprises a chamber 501 of a squared cylinder, a wafer carrying in/out door 502 connected to the chamber 501 and an automatic aperture apparatus for a door at a substrate carrying in/out aperture positioned at a side of the chamber 501 and capable of aperture and closing mechanically the aperture, a cap 503 positioned in opposite to the aperture for covering an aperture for the purpose of detachably mounting filers and fan motors, and a slotted pocket 507 for holding a wafer W. In this embodiment, the wafers are carried in and out by means of a robot type carrying unit 612 of the loader 60.

It should be noted that wafers accommodated in the manufacturing processes. Specifically, accommodated in the cassette are wafers which have undergone a deposition process, CMP, ion implantation and so on; wafers each formed with wiring patterns on the surface thereof; or wafers which have not been formed with wiring patterns. Since a large number of wafers accommodated in the cassette a are spaced from each other in the vertical direction and arranged side by side in parallel, and the first carrier unit has an arm which is vertically movable, a wafer at an arbitrary position can be held by the first carrier unit which will be described later in detail.

Mini-Environment Device 20

Figure 4:
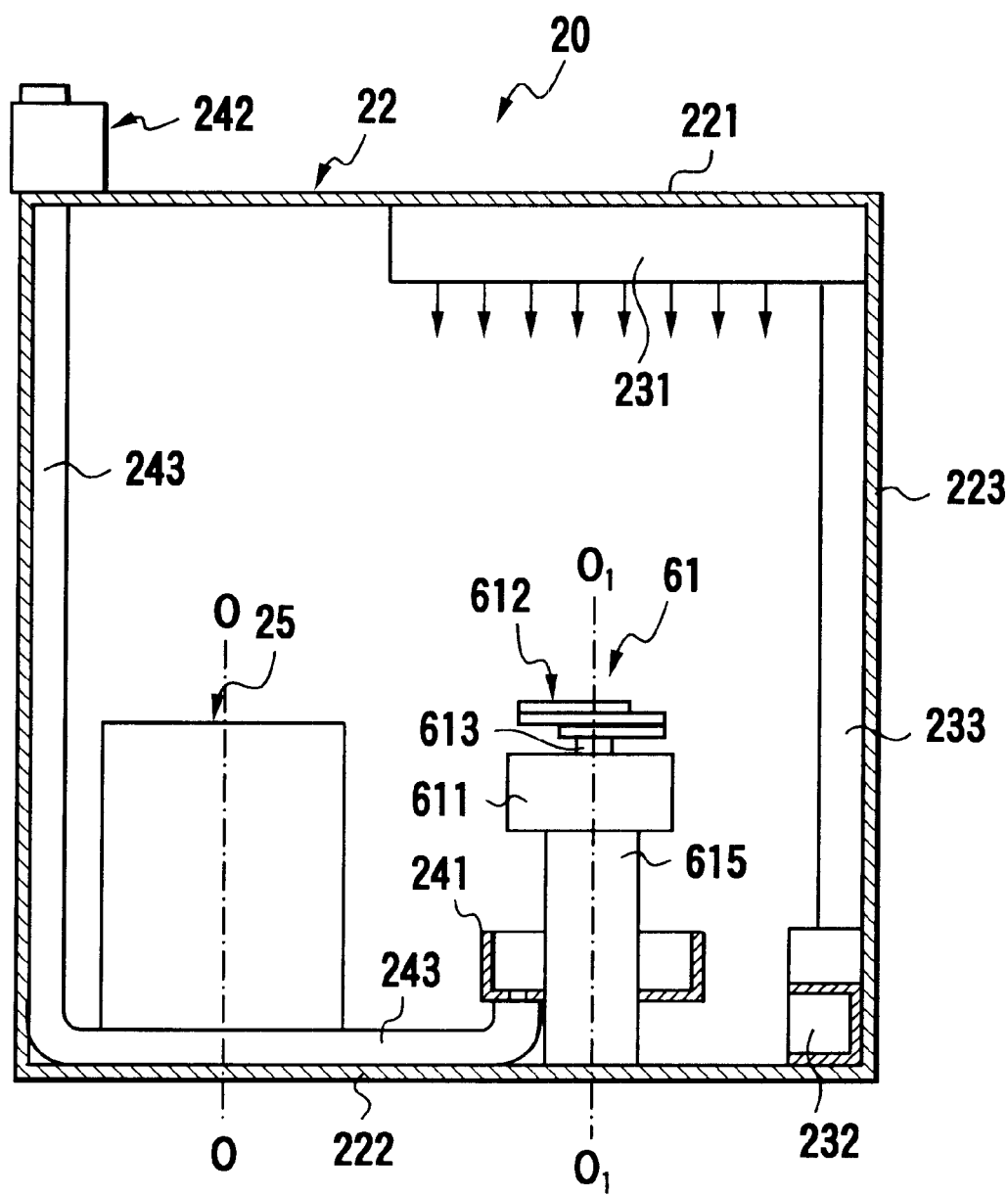
FIG. 4 is a cross section of the mini environment device shown in FIG. 1 taken along the line C—C in FIG. 1.

In FIG. 4 shows an elevation of the mini-environment device 20 in a direction different to that in FIG. 1. As illustrated in FIG. 4 as well as FIGS. 1 and 2, the mini-environment device 20 comprises a housing 22 defining a mini-environment space 21 that is controlled for the atmosphere; a gas circulator 23 for circulating a gas such as clean air within the mini-environment space 21 to execute the atmosphere control; a discharger 24 for recovering a portion of air supplied into the mini-environment space 21 to discharge it; and a prealigner 25 for roughly aligning a sample, i.e., a wafer placed in the mini-environment space 21.

The housing 22 has a top wall 221, bottom wall 222, and peripheral wall 223 which surrounds four sides of the housing 22, to provide a structure for isolating the mini-environment space 21 from the outside. For controlling the atmosphere in the mini-environment space 21, as illustrated in FIG. 4, the gas circulator 23 comprises a gas supply unit 231 attached to the top wall 221 within the mini-environment space 21 for cleaning a gas (air in this embodiment) and delivering the cleaned gas downward through one or more gas nozzles (not shown) in laminar flow; a recovery duct 232 disposed on the bottom wall 222 within the mini-environment space for recovering air which has flown down to the bottom; and a conduit 233 for connecting the recovery duct 232 to the gas supply unit 231 for returning recovered air to the gas supply unit 231.

In this embodiment, the gas supply unit 231 takes about 20% of air to be supplied, from the outside of the housing 22 to clean the air in the mini-environment space 21. However, the percentage of gas taken from the outside may be arbitrarily selected. The gas supply unit 231 comprises an HEPA or ULPA filter in a known structure for creating cleaned air. The laminar down-flow of cleaned air is mainly supplied such that the air passes a carrying surface formed by the first carrier unit (which is described later) disposed within the mini-environment space 21 to prevent particle particles, which could be produced by the carrier unit, from attaching to the wafer. Therefore, the down-flow nozzles need not be positioned near the top wall as illustrated, but is only required to be above the carrying surface formed by the carrier unit. In addition, the air is not supplied over the entire mini-environment space 21. It should be noted that an ion wind may be used as cleaned air to ensure the cleanliness. Also, a sensor may be provided within the mini-environment space 21 for observing the cleanliness such that the apparatus is shut down when the cleanliness is degraded. An access port 225 is formed in a portion of the peripheral wall 223 of the housing 22 that is adjacent to the cassette holder 10. A gate valve in a known structure may be provided near the access port 225 to shut the port from the mini-environment device 20. The laminar down-flow near the wafer may be, for example, at a rate of 0.3 to 0.4 m/sec. The gas supply unit 231 may be disposed outside the mini-environment space 21 instead of within the space.

The discharger 24 comprises a suction duct 241 disposed at a position below the wafer carrying surface of the carrier unit and below the carrier unit; a blower 242 disposed outside the housing 22; and a conduit 243 for connecting the suction duct 241 to the blower 242. The discharger 24 aspires a gas flowing down around the carrier unit and including particle, which could be produced by the carrier unit, through the suction duct 241, and discharges the gas outside the housing 22 through the conduits 243, 244 and the blower 242. In this event, the gas may be discharged into an pumping pipe (not shown) which is laid to the vicinity of the housing 22.

The prealigner 25 disposed within the mini-environment space 21 optically or mechanically detects an orientation flat (which refers to a flat portion formed along the outer periphery of a circular wafer and hereunder called as ori-fla) formed on the wafer, or one or more V-shaped notches formed on the outer peripheral edge of the wafer, and previously aligns the position of the waver in a rotating direction about the axis $O_1$—$O_1$ at an accuracy of approximately ± one degree. The prealigner forms part of a mechanism for determining the coordinates of the wafer, and executes a rough alignment of the wafer. Since the pre-aligner itself may be of a known structure, explanation on its structure and operation is omitted. Though not shown, a recovery duct for the discharger may also be provided below the prealigner so that air including particle discharged from the prealigner, may be discharged to the outside.

Main Housing 30

As illustrated in FIGS. 1 and 2, the main housing 30 which defines the working chamber 31, comprises a housing body 32 that is supported by a housing supporting device 33 carried on a vibration isolator 37 disposed on a base frame 36. The housing supporting device 33 comprises a frame structure 331 assembled into a rectangular form. The housing body 32 comprises a bottom wall 321 mounted on and securely carried on the frame structure 331; a top wall 322; and a peripheral wall 323 which is connected to the bottom wall 321 and the top wall 322 and surrounds four sides of the housing body 32, thereby isolating the working chamber 31 from the outside. In this embodiment, the bottom wall 321 is made of a relatively thick steel plate to prevent distortion due to the weight of equipment carried thereon such as the stage apparatus 50. Alternatively, another structure may be employed. In this embodiment, each of the housing body 32 and the housing supporting device 33 is assembled into a rigid construction, and the vibration isolator 37 blocks vibrations from the floor, on which the base frame 36 is installed, from being transmitted to the rigid structure. A portion of the peripheral wall 323 of the housing body 32 that adjoins the loader housing 40 is formed with an access port 325 for introducing and removing a wafer.

The vibration isolator may be either of an active type which has an air spring, a magnetic bearing and so on, or a passive type likewise having these components. Since any known structure may be employed for the vibration isolator, description on the structure and functions of the vibration isolator itself is omitted. The working chamber 31 is kept in a vacuum atmosphere by a vacuum system (not shown) in a known structure. A controller 2 for controlling the operation of the overall evacuation system is disposed below the base frame 36.

In the evaluation system 1, some housings including the main housing 30 are kept in vacuum atmosphere. A system for evaporating such a housing comprises a vacuum pump, vacuum valve, vacuum gauge, and vacuum pipes, and evaporates the housing such as an electro-optical system portion, detector portion, wafer housing, load lock housing or the like, in accordance with a predetermined sequence. The vacuum valves are adjusted to kept a required vacuum level of the housings. Further, the vacuum levels are always monitored, and when an abnormal vacuum level is detected, an interlock function enables isolation valves to shut dawn the path between chambers or between a chamber and a pumping system to kept the required vacuum level of the housing. As to the vacuum pump, a turbo-molecular pump can be utilized for main evacuation, and a dry pump of a Roots type can be utilized for rough evacuation. The pressure at a test location (electron beam irradiated region) is $10^{-3}$ to $10^{-5}$ Pa. Preferably, pressure of $10^{-4}$ to $10^{-6}$ Pa is practical.

Loader Housing 40

Figure 5:
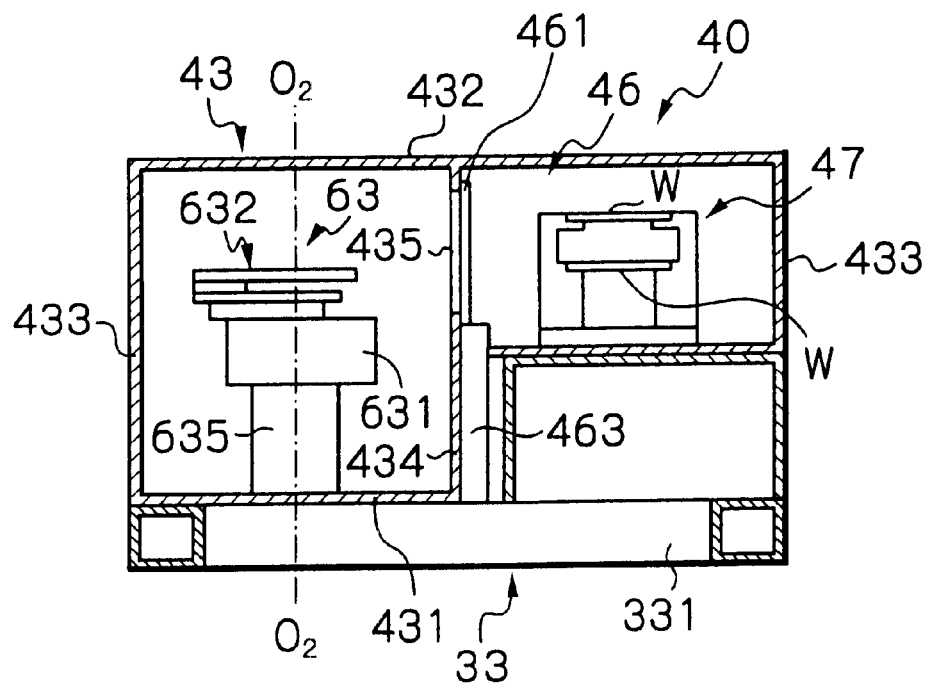
FIG. 5 illustrates the loader housing indicated in FIG. 1 seen along the line D—D in FIG. 2.

FIG. 5 shows an elevation of the loader housing 40, in view of the direction different to that in FIG. 1. As illustrated in FIG. 5 as well as FIGS. 1 and 2, the loader housing 40 comprises a housing body 43 which defines a first loading chamber 41 and a second loading chamber 42. The housing body 43 comprises a bottom wall 431; a top wall 432; a peripheral wall 433 which surrounds four sides of the housing body 43; and a partition wall 434 for partitioning the first loading chamber 41 and the second loading chamber 42 to isolate the two loading chambers from the outside. The partition wall 434 is formed with an aperture, i.e., an access port 435 for passing a wafer W between the two loading chambers. Also, a portion of the peripheral wall 433 that adjoins the mini-environment device 20 and the main housing 30, is formed with access ports 436, 437. The housing body 43 of the loader housing 40 is carried on and supported by the frame structure 331 of the housing supporting device 33. This prevents the vibrations of the floor from being transmitted to the loader housing 40 as well.

The access port 436 of the loader housing 40 is in alignment with the access port 226 of the housing 22 of the mini-environment device 20, and a gate valve 27 is provided for selectively blocking a communication between the mini-environment space 21 and the first loading chamber 41. The gate valve 27 has a sealing member 271 which surrounds the peripheries of the access ports 226, 436 and is fixed to the side wall 433 in close contact therewith; a door 272 for blocking air from flowing through the access ports in cooperation with the sealing material 271; and a driver 273 for moving the door 272. Likewise, the access port 437 of the loader housing 40 is in alignment with the access port 325 of the housing body 32, and a gate valve 45 is provided for selectively blocking a communication between the second loading chamber 42 and the working chamber 31 in a hermetic manner. The gate valve 45 comprises a sealing member 451 which surrounds the peripheries of the access ports 437, 325 and is fixed to side walls 433, 323 in close contact therewith; a door 452 for blocking air from flowing through the access ports in cooperation with the sealing material 451; and a driver 453 for moving the door 452. Further, the aperture formed through the partition wall 434 is provided with a gate valve 46 for closing the aperture with the door 461 to selectively blocking a communication between the first and second loading chambers in a hermetic manner. These gate valves 27, 45, 46 are configured to provide air-tight sealing for the respective chambers when they are in a closed state. Since these gate valves may be implemented by conventional ones, detailed description on their structures and operations is omitted.

It should be noted that a method of supporting the housing 22 of the mini-environment chamber 20 is different from a method of supporting the loader housing 40. Therefore, for preventing vibrations from being transmitted from the floor through the mini-environment chamber 20 to the loader housing 40 and the main housing 30, a vibration-absorption damper member may be disposed between the housing 22 and the loader housing 40 to provide air-tight sealing for the peripheries of the access ports.

Within the first loading chamber 41, a wafer rack 47 is disposed for supporting a plurality (two in this embodiment) of wafers spaced in the vertical direction and maintained in a horizontal state. As illustrated in FIG. 6, the wafer rack 47 comprises posts 472 fixed at four corners of a rectangular substrate 471, spaced from one another, in an upright state. Each of the posts 472 is formed with supporting devices 473, 474 in two stages, such that peripheral edges of wafers W are carried on and held by these supporting devices. Then, bottoms of arms of the first and second carrier units, later described, are brought closer to wafers from adjacent posts and chuck the wafers.

The loading chambers 41, 42 can be controlled for the atmosphere to be maintained in a high vacuum state (at a vacuum degree of $10^{-5}$ to $10^{-6}$ Pa) by a vacuum evacuator (not shown) in a conventional structure including a vacuum pump, not shown. In this event, the first loading chamber 41 may be held in a low vacuum atmosphere as a low vacuum chamber, while the second loading chamber 42 may be held in a high vacuum atmosphere as a high vacuum chamber, to effectively prevent contamination of wafers. The employment of such a loading housing structure including two loading chambers allows a wafer W to be carried, without significant delay from the loading chamber the working chamber. The employment of such a loading chamber structure provides for an improved throughput for the defect testing, and the highest possible vacuum state around the electron source which is required to be kept in a high vacuum state.

The first and second loading chambers 41, 42 are connected to vacuum pumping pipes and vent pipes for an inert gas (for example, dried pure nitrogen) (neither of which are shown), respectively. In this way, the atmospheric state within each loading chamber is attained by an inert gas vent (which injects an inert gas to prevent an oxygen gas and so on other than the inert gas from attaching on the surface). Since an apparatus itself for implementing the inert gas vent is known in structure, detailed description thereon is omitted.

In the main housing 30 of the invention using electron beams, when representative lanthanum hexaborate (LaB6) used as an electron source for an electro-optical system, later described, is once heated to such a high temperature that causes emission of thermal electrons, it should not be exposed to oxygen within the limits of possibility so as not to shorten the lifetime. In the invention, the exposure to oxygen can be prevented without fail by carrying out the atmosphere control as mentioned above at a stage before introducing the wafer W into the working chamber of the main housing in which the electro-optical system 70 is disposed.

Stage apparatus 50

The stage apparatus 50 comprises a fixed table 51 disposed on the bottom wall 321 of the main housing 30; a Y-table 52 movable in a Y-direction on the fixed table (the direction vertical to the drawing sheet in FIG. 1); an X-table 53 movable in an X-direction on the Y-table 52 (in the left-to-right direction in FIG. 1); a turntable 54 rotatable on the X-table; and a holder 55 disposed on the turntable 54. A wafer is releasably held on a wafer carrying surface 551 of the holder 55. The holder 55 may be of a conventional structure which is capable of releasably chucking a wafer by means of a mechanical or electrostatic chuck feature. The stage apparatus 50 uses servo motors, encoders and a variety of sensors (not shown) to operate the above tables to permit highly accurate alignment of a wafer held on the carrying surface 551 by the holder 55 in the X-direction, Y-direction and Z-direction (the Z-direction is the up-down direction in FIG. 1) with respect to electron beams irradiated from the electro-optical system 70, and in a direction ($\theta$ direction) about the axis normal to the wafer supporting surface. The alignment in the Z-direction may be made such that the position on the carrying surface 551 of the holder 55, for example, can be finely adjusted in the Z-direction. In this event, a reference position on the carrying surface is sensed by a position measuring device using a laser of an extremely small diameter (a laser interference range finder using the principles of interferometer) to control the position by a feedback circuit (not shown). Additionally or alternatively, the position of a notch or an orientation flat of a wafer is measured to sense a plane position or a rotational position of the wafer relative to the electron beam to control the position of the wafer by rotating the turntable 54 by a stepping motor which can be controlled in extremely small angular increments. It may be possible to remove the holder 55 and carry a wafer W directly on the rotational table. In order to maximally prevent particle produced within the working chamber, servo motors 531, 531 and encoders 522, 532 for the stage apparatus 50 are disposed outside the main housing 30. Since the stage apparatus 50 may be of a conventional structure used, for example, in steppers and so on, detailed description on its structure and operation is omitted. Likewise, since the laser interference range finder may also be of a conventional one, detailed description on its structure and operation is omitted.

It is also possible to establish a basis for signals which are generated by previously inputting a rotational position, and X-Y-positions of a wafer relative to the electron beams in a signal detecting system or an image processing system, later described. The wafer chucking mechanism provided in the holder 55 is configured to apply a voltage for chucking a wafer to an electrode of an electrostatic chuck, and the alignment is made by pinning three points on the outer periphery of the wafer (preferably spaced equally in the circumferential direction). The wafer chucking mechanism comprises two fixed aligning pins and a push-type clamp pin. The clamp pin can implement automatic chucking and automatic releasing, and constitutes a conducting spot for applying the voltage.

Figure 6A:
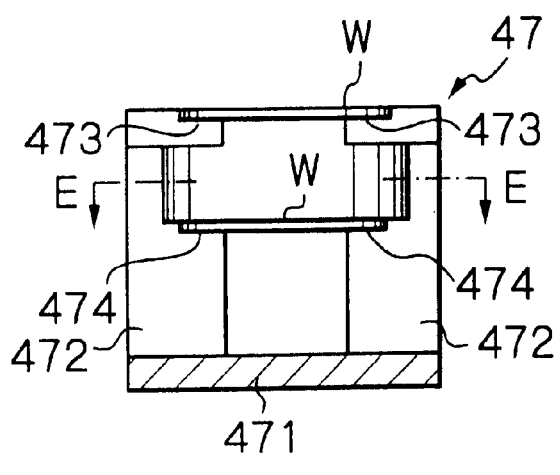
Figure 6B:
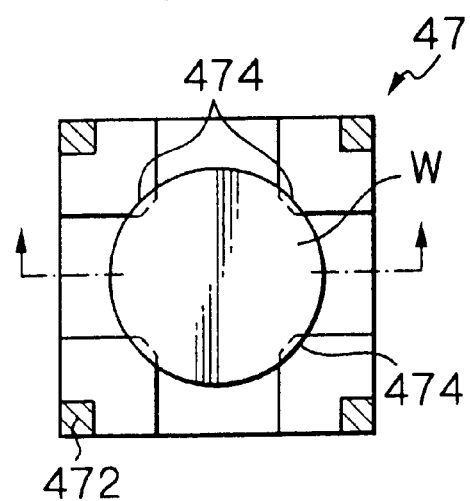

While in this embodiment, the X-table is defined as a table which is movable in the left-to-right direction in FIG. 6(a); and the Y-table as a table which is movable in the up-down direction, a table movable in the left-to-right direction in FIG. 2 may be defined as the Y-table; and a table movable in the up-down direction as the X-table.

Loader 60

The loader 60 comprises a robot-type first carrier unit 61 disposed within the housing 22 of the mini-environment chamber 20; and a robot-type second carrier unit 63 disposed within the second loading chamber 42.

The first carrier unit 61 comprises a multi-node arm 612 rotatable about an axis $O_1$—$O_1$ with respect to a driver 611.

While an arbitrary structure may be used for the multi-node arm, the multi-node arm in this embodiment has three parts which are pivotably attached to each other. One part of the arm 612 of the first carrier unit 61, i.e., the first part closest to the driver 611 is attached to a rotatable shaft 613 by a driving mechanism (not shown) of a conventional structure, disposed within the driver 611. The arm 612 is pivotable about the axis $O_1$—$O_1$ by means of the shaft 613, and radially telescopic as a whole with respect to the axis $O_1$—$O_1$ through relative rotations among the parts. At a bottom of the third part of the arm 612 furthest away from the shaft 613, a chuck 616 in a conventional structure for chucking a wafer, such as a mechanical chuck or an electrostatic chuck, is disposed. The driver 611 is movable in the vertical direction by an elevating mechanism 615 of a conventional structure.

The first carrier unit 61 extends the arm 612 in either a direction M1 or a direction M2 (FIG. 2) within two cassettes cheld in the cassette holder 10, and removes a wafer accommodated in a cassette cby carrying the wafer on the arm or by chucking the wafer with the chuck (not shown) attached at the bottom of the arm. Subsequently, the arm is retracted (in a state as illustrated in FIG. 2), and then rotated to a position at which the arm can extend in a direction M3 toward the prealigner 25, and stopped at this position. Then, the arm is again extended to transfer the wafer held on the arm to the prealigner 25. After receiving a wafer from the prealigner 25, contrary to the foregoing, the arm is further rotated and stopped at a position at which it can extend to the second loading chamber 41 (in the direction M4), and transfers the wafer to a wafer receiver 47 within the second loading chamber 41. For mechanically chucking a wafer, the wafer should be chuck bed on a peripheral region (in a range of approximately 5 mm from the peripheral edge). This is because the wafer is formed with devices (circuit patterns) over the entire surface except for the peripheral region, and chucking the inner region would result in failed or defective devices.

The second carrier unit 63 is basically identical to the first carrier unit 61 in structure except that the second carrier unit 63 carries a wafer between the wafer rack 47 and the carrying surface of the stage apparatus 50, so that detailed description thereon is omitted.

Each of the first and second carrier units 61, 63 carry a wafer from a cassette held in the cassette holder 10 to the stage apparatus 50 disposed in the working chamber 31 and vice versa, while remaining substantially in a horizontal state. The arms of the carrier units 61, 63 are moved in the vertical direction only when a wafer is removed from and inserted into a cassette, when a wafer is carried on and removed from the wafer rack, and when a wafer is carried on and removed from the stage apparatus 50. It is therefore possible to smoothly carry a larger wafer, for example, a wafer having a diameter of 30 cm.

Next, how a wafer is carried will be described in sequence from the cassette cheld by the cassette holder 10 to the stage apparatus 50 disposed in the working chamber 31.

As described above, when the cassette is manually set, the cassette holder 10 having a structure adapted to the manual setting is used, and when the cassette is automatically set, the cassette holder 10 having a structure adapted to the automatic setting is used. In this embodiment, as the cassette cis set on the up/down table 11 of the cassette holder 10, the up/down table 11 is moved down by the elevating mechanism 12 to align the cassette cwith the access port 225.

As the cassette is aligned with the access port 225, a cover (not shown) provided for the cassette is opened, and a cylindrical cover is applied between the cassette cand the access port 225 of the mini-environment to block the cassette and the mini-environment space 21 from the outside. Since these structures are known, detailed description on their structures and operations is omitted. When the mini-environment device 20 is provided with a gate valve for aperture and closing the access port 225, the gate valve is operated to open the access port 225.

On the other hand, the arm 612 of the first carrier unit 61 remains oriented in either the direction M1 or M2 (in the direction M1 in this description). As the access port 225 is opened, the arm 612 extends to receive one of wafers accommodated in the cassette at the bottom. While the arm and a wafer to be removed from the cassette are adjusted in the vertical position by moving up or down the driver 611 of the first carrier unit 61 and the arm 612 in this embodiment, the adjustment may be made by moving up and down the up/down table 11 of the cassette holder 10, or made by both.

As the arm 612 has received the wafer, the arm 621 is retracted, and the gate valve is operated to close the access port (when the gate valve is provided). Next, the arm 612 is pivoted about the axis $O_1$—$O_1$ such that it can extend in the direction M3. Then, the arm 612 is extended and transfers the wafer carried at the bottom or grabbed by the chuck onto the prealigner 25 which aligns the orientation of the rotating direction of the wafer (the direction about the central axis vertical to the wafer plane) within a predetermined range. Upon completion of the alignment, the carrier unit 61 retracts the arm 612 after a wafer has been received from the prealigner 25 to the bottom of the arm 612, and takes a posture in which the arm 612 can be extended in a direction M4. Then, the door 272 of the gate valve 27 is moved to open the access ports 223, 236, and the arm 612 is extended to place the wafer on the upper stage or the lower stage of the wafer rack 47 within the first loading chamber 41. It should be noted that before the gate valve 27 opens the access ports to transfer the wafer to the wafer rack 47, the aperture 435 formed through the partition wall 434 is closed by the door 461 of the gate valve 46 in an air-tight state.

In the process of carrying a wafer by the first carrier unit, clean air flows (as down flows) in laminar flow from the gas supply unit 231 disposed on the housing of the mini-environment chamber to prevent particle from attaching on the upper surface of the wafer during the carriage. A portion of the air near the carrier unit (in this embodiment, about 20% of the air supplied from the supply unit 231, mainly contaminated air) is aspired from the suction duct 241 of the discharger 24 and discharged outside the housing. The remaining air is recovered through the recovery duct 232 disposed on the bottom of the housing and returned again to the gas supply unit 231.

As the wafer is placed into the wafer rack 47 within the first loading chamber 41 of the loader housing 40 by the first carrier unit 61, the gate valve 27 is closed to seal the loading chamber 41. Then, the first loading chamber 41 is filled with an inert gas to expel air. Subsequently, the inert gas is also evacuated so that a vacuum atmosphere dominates within the loading chamber 41. The vacuum atmosphere within the loading chamber 41 may be at a low vacuum degree. When a certain degree of vacuum is provided within the loading chamber 41, the gate valve 46 is operated to open the access port 434 which has been sealed by the door 461, and the arm 632 of the second carrier unit 63 is extended to receive one wafer from the wafer receiver 47 with the chuck at the bottom (the wafer is carried on the bottom or grabbed by the chuck attached to the bottom). Upon completion of the receipt of the wafer, the arm 632 is retracted, followed by the gate valve 46 again operated to close the access port 435 by the door 461. It should be noted that the arm 632 has previously taken a posture in which it can extend in the direction N1 of the wafer rack 47 before the gate valve 46 is operated to open the access port 435. Also, as described above, the access ports 437, 325 have been closed by the door 452 of the gate valve 45 before the gate valve 46 is operated to block the communication between the second loading chamber 42 and the working chamber 31 in an air-tight state, so that the second loading chamber 42 is evacuated.

As the gate valve 46 is operated to close the access port 435, the second loading chamber 42 is again evacuated at a higher degree of vacuum than the first loading chamber 41. Meanwhile, the arm 632 of the second carrier unit 63 is rotated to a position at which it can extend toward the stage apparatus 50 within the working chamber 31. On the other hand, in the stage apparatus 50 within the working chamber 31, the Y-table 52 is moved upward, as viewed in FIG. 2, to a position at which the center line $O_0$—$O_0$ of the X-table 53 substantially matches an X-axis $X_1$—$X_1$ which passes a pivotal axis $O_2$—$O_2$ of the second carrier unit 63. The X-table 53 in turn is moved to the position closest to the leftmost position in FIG. 2, and remains awaiting at this position. When the second loading chamber 42 is evacuated to substantially the same degree of vacuum as the working chamber 31, the door 452 of the gate valve 45 is moved to open the access ports 437, 325, allowing the arm 632 to extend so that the bottom of the arm 632, which holds a wafer, approaches the stage apparatus 50 within the working chamber 31. Then, the wafer is placed on the carrying surface 551 of the stage apparatus 50. As the wafer has been placed on the carrying surface 551, the arm 632 is retracted, followed by the gate 45 operated to close the access ports 437, 325.

The foregoing description has been made on the operation until a wafer in the cassette a is carried and placed on the stage apparatus 50. For returning a wafer, which has been carried on the stage apparatus 50 and processed, from the stage apparatus 50 to the cassette c, the operation reverse to the foregoing is performed. Since a plurality of wafers are stored in the wafer rack 47, the first carrier unit 61 can carry a wafer between the cassette and the wafer rack 47 while the second carrier unit 63 is carrying a wafer between the wafer rack 47 and the stage apparatus 50, so that the testing operation can be efficiently carried out.

Specifically, if an already-processed wafer A and a unprocessed wafer B are placed on the wafer rack 47 of the second carrier unit, (1) the unprocessed wafer B is moved to the stage apparatus 50 and a process for the wafer B starts. In the middle of this process, (2) the processed wafer A is moved to the wafer rack 47 from the stage apparatus 50. A unprocessed wafer C is likewise extracted from the wafer rack 47 by the arm and is aligned by the pre-aligner. Then, the wafer C is moved to the wafer rack of the loading chamber 41. By doing so, it is possible to replace the wafer A with the unprocessed wafer C in the wafer rack 47 during the wafer B is being processed.

Depending upon how such an apparatus for performing a test or evaluation is utilized, a plurality of the stage apparatus 50 can be disposed to cause a wafer to be transferred from one wafer rack 47 to each stage apparatus, making it possible to process a plurality of wafers in a similar manner.

Figure 7A:
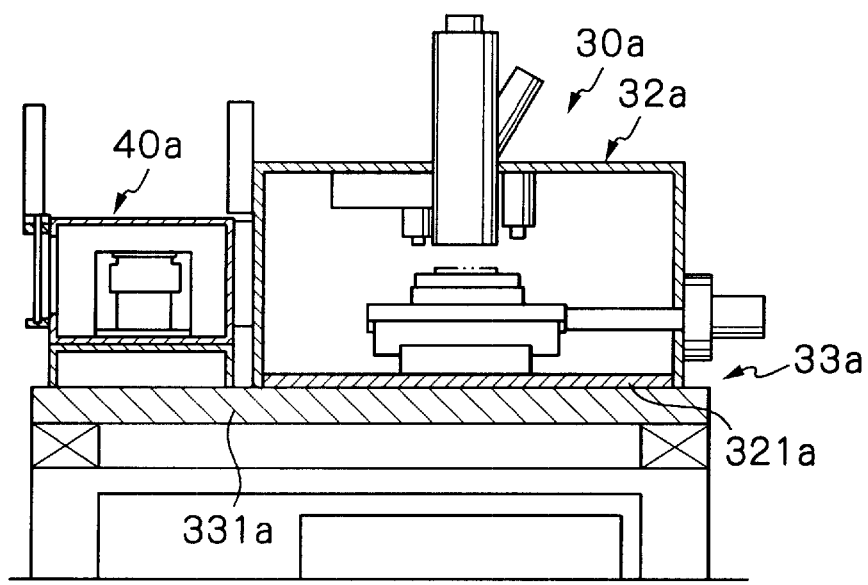
FIGS. 7A and 7B illustrate a variation of a method of supporting a main housing.
Figure 7B:
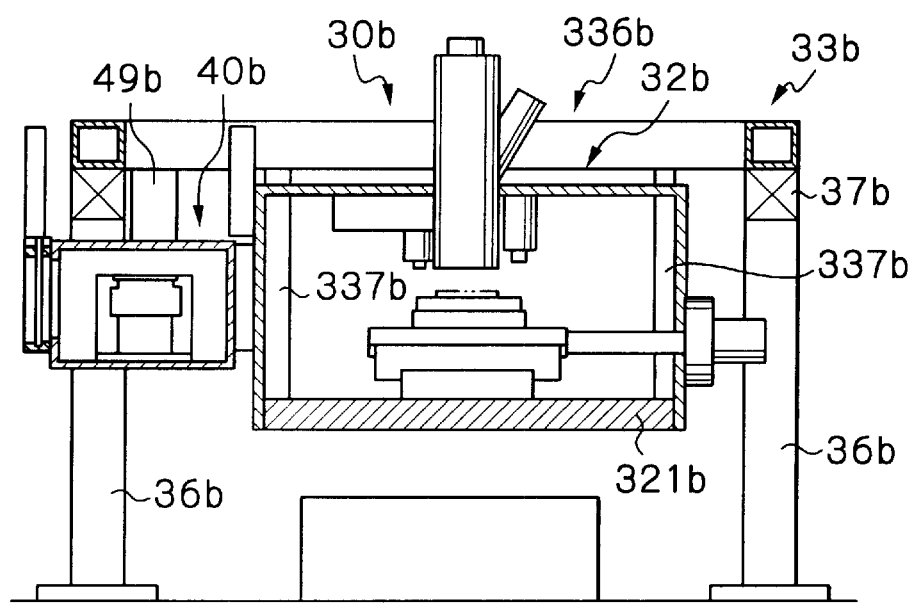

FIGS. 7A and 7B illustrate an exemplary modification to the method of supporting the main housing 30. In an exemplary modification illustrated in FIG. 7A, a housing supporting device 33a is made of a thick rectangular steel plate 331a, and a housing body 32a is carried on the steel plate. Therefore, the bottom wall 321a of the housing body 32a is thinner than the bottom wall 222 of the housing body 32 in the foregoing embodiment. In an exemplary modification illustrated in FIG. 7B, a housing body 32b and a loader housing 40b are suspended by a frame structure 336b of a housing supporting device 33b. Lower ends of a plurality of vertical frames 337b fixed to the frame structure 336b are fixed to four corners of a bottom wall 321b of the housing body 32b, such that the peripheral wall and the top wall are supported by the bottom wall. A vibration isolator 37b is disposed between the frame structure 336b and a base frame 36b. Likewise, the loader housing 40 is suspended by a suspending member 49b fixed to the frame structure 336. In the exemplary modification of the housing body 32b illustrated in FIG. 7B, the housing body 32b is supported in suspension, the general center of gravity of the main housing and a variety of devices disposed therein can be brought downward. The methods of supporting the main housing and the loader housing are configured to prevent vibrations from being transmitted from the floor to the main housing and the loader housing.

In another exemplary modification, not shown, the housing body of the main housing is only supported by the housing supporting device from below, while the loader housing may be placed on the floor in the same way as the adjacent mini-environment chamber. Alternatively, in a further exemplary modification, not shown, the housing body of the main housing is only supported by the frame structure in suspension, while the loader housing may be placed on the floor in the same way as the adjacent mini-environment device.

Electro-optical System 70

The electro-optical system 70 comprises a column or column 71 fixed on the housing body 32. Disposed within the column 71 are an electro-optical system comprised of a primary electro-optical system (hereinafter simply called the "primary optical system") and a secondary electro-optical system (hereinafter simply called the "secondary optical system"), and a detecting system.

Figure 8:
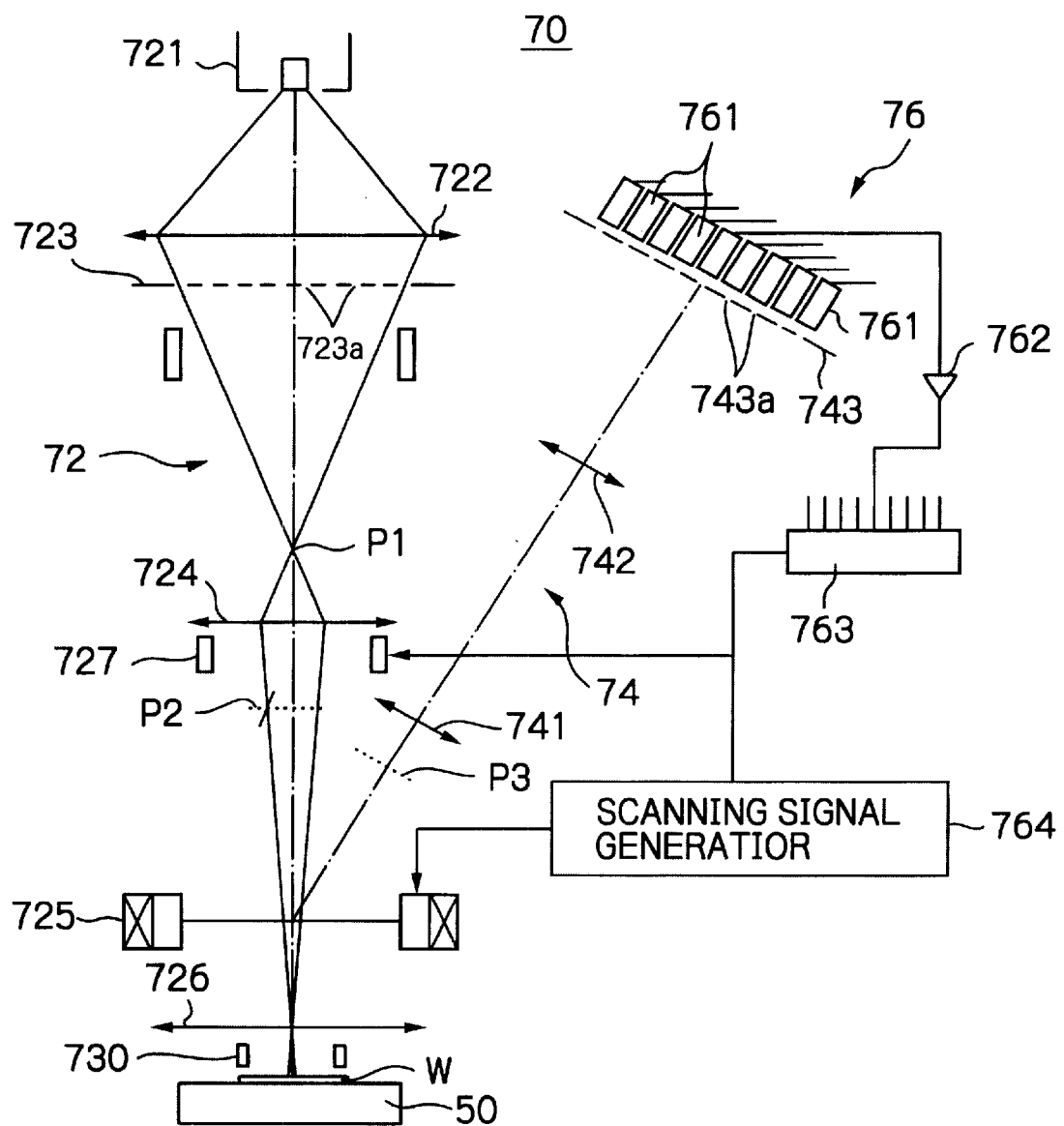
FIG. 8 schematically illustrates an embodiment of an electron beam apparatus concerning the present invention, which can be applied to the evaluation system indicated in FIG. 1.

FIG. 8 shows an embodiment of the electro-optical system 70. In the drawing, 72 denotes a primary optical system, 74 a secondary optical system and 76 a detecting system. FIG. 8 also illustrates a stage apparatus 50 carrying a wafer W and a scanning signal generation circuit 764 which is a part of a control apparatus. The primary optical system 72 irradiates the surface of the sample or wafer W with electron beams, and comprises an electron gun 721 for emitting an electron beam(s); a condenser lens 722 comprised of an electrostatic lens for converging the primary the electron beam emitted from the electron gun 721; a multi-aperture plate 723 located below the condenser lens 722 and having a plurality of apertures, for forming a plurality of primary electron beams or multi-beams from the primary electron beam from the gun 721; a reducing lens 724 comprised of an electrostatic lens for reducing the primary electron beams; a Wien filter or an ExB separator or deflector 725; and an objective lens 726. These components are arranged in order with the electron gun 721 placed at the top, as illustrated in FIG. 8, and settled such that the optical axes of the electron beams irradiated are orthogonal to the surface of the wafer W.

Figure 9A:
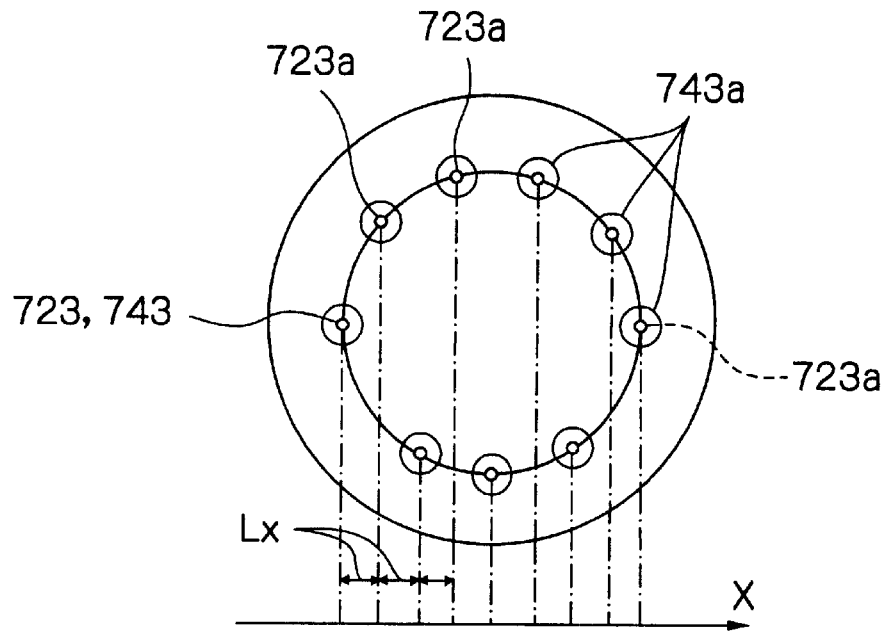
FIG. 9A illustrates an arrangement of apertures bored on a multi-aperture plate used in primary and secondary optical systems of the electron beam apparatus shown in FIG. 8.

In order to reduce aberration effect of field curvature by the reducing lens 724 and objective lens 726, the multiapertures 723a (9 apertures in this embodiment) are positioned through the multi-aperture plate 723 such that when the apertures are projected on the X-axis, the distance Lx between the adjacent points on the X-axis is equal, as shown in FIG. 9A.

The secondary optical system 74 comprises magnification lenses 741, 742 each comprised of an electrostatic lens which pass secondary electrons separated from the primary optical system by an ExB deflector 725; and a multi-aperture plate 743. A plurality of apertures 743a of the multi-aperture plate 743 are located such that they coincide, one by one, with the apertures 723a of the multi-aperture plate 723 of the primary optical system, as illustrated in FIG. 9A.

The detecting system 76 comprises a plurality of detectors 761 (9 detectors in this embodiment) the number of which is equal to that of the apertures 743a of the multi-aperture plate 743 of the secondary optical system 74 and located correspondingly thereto; and an image processing section 763 connected through A/D converters 762. The image processing section 763 is not necessary to physically located in the electro-optical system 70.

Next, the operation of the electro-optical system 70 configured as described above will be described. The primary electron beam emitted from the electron gun 721 is converged by the condenser lens 722 to form a cross-over at a point P. The primary electron beam which has been converged by the condenser lens 722 passes through the apertures 723a of the multi-aperture plate 723, resulting in that a multiple electron beams are created. Each of the multi-electron beams is then reduced by the reducing lens 724 and projected at a point P2. After the focussing at the point P2, the beam passes the objective lens 726 to focus on the surface of the wafer W. In this situation, the primary electron beams are deflected by a deflector 727 located between the reducing lens 724 and the objective lens 726 to be scanned on the surface of the wafer W. The deflector 727 deflects the primary electron beams in response to a scanning signal applied thereto.

Figure 9B:
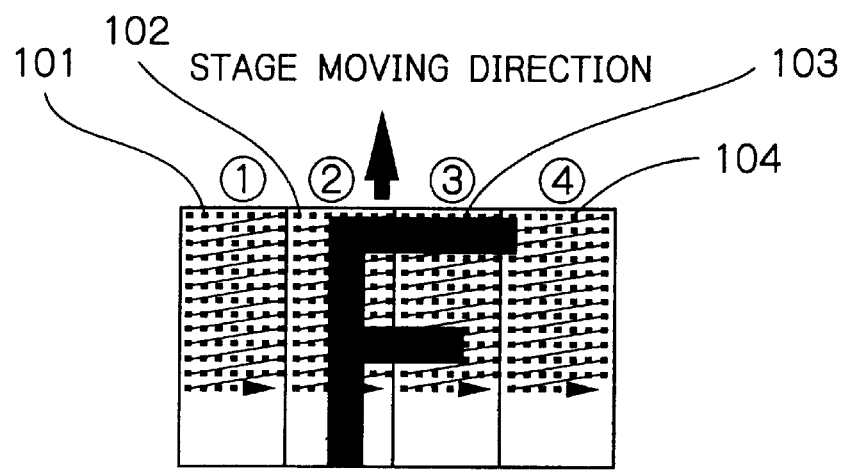
FIG. 9B depicts a mode of primary electron beam scanning.

A method of irradiating primary electron beams by the primary optical system 72 will next be explained, with reference to FIG. 9B. In the example of FIG. 9B, in order to make explanation brief, four primary electron beams 101, 102, 103, 104 are employed. It is assumed that each of the electron beams is scanned by 50 μm width. As to the beam 101, it scans in the right direction from the left end, returns to the left end immediately after reaching the right end, and again scans in the right direction. Since the four electron beams scan simultaneously on a wafer surface, a throughput can be improved.

Returning to FIG. 8, a plurality of points on the wafer W are illuminated by a plurality of focussed primary electron beams (nine beams in the embodiment in FIG. 8), resulting in that secondary electrons are emitted from the illuminated points. The secondary electrons are then converged by pulling the electric field created by the objective lens, deflected by the ExB separator 725 to be directed to the secondary optical system 74. An image created by the secondary electrons are focussed at a point P3 which is closer than the point P2. This is because a primary electron has energy of about 500 eV and the secondary electron has energy of only several eV.

Figure 10A:
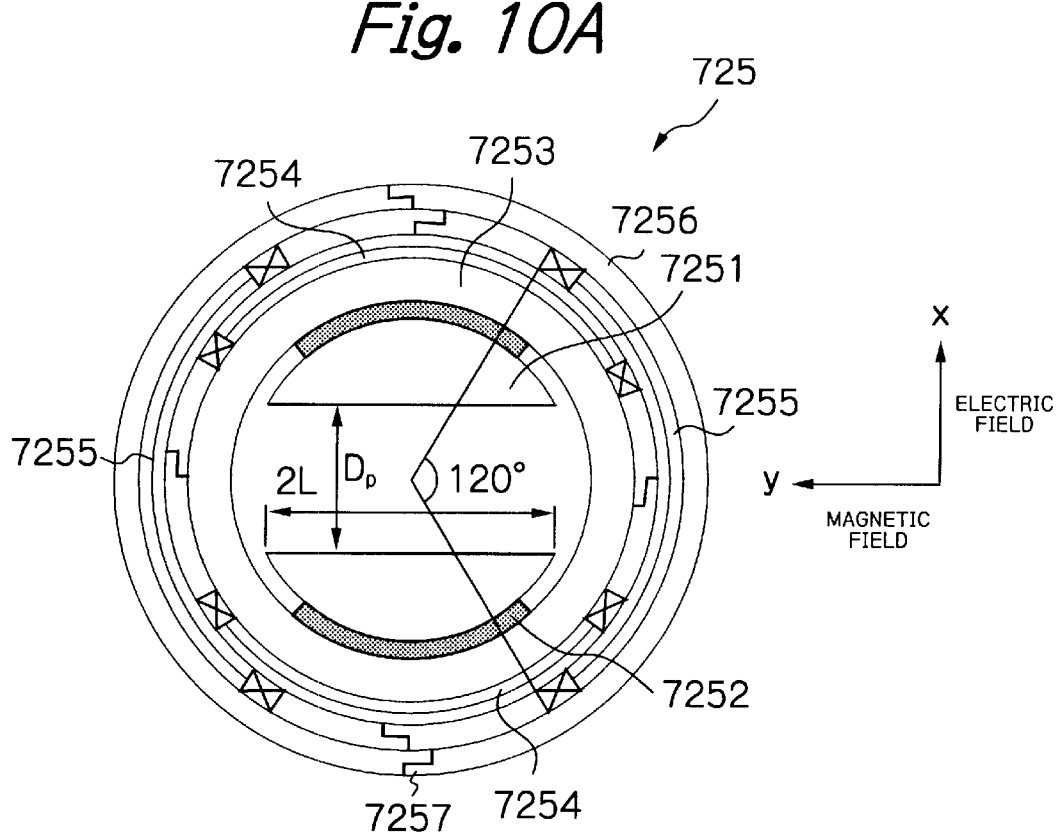
FIGS. 10A and 10B illustrate embodiments of an ExB separator applicable to the electron beam apparatus concerning the present invention.

It will be explained the ExB separator 725 with reference to FIG. 10. FIG. 10A illustrates an example of the ExB separator applicable to the electro-optical apparatus according to the present invention. The ExB separator comprises an electro-static deflector and electromagnetic deflector. FIG. 10 shows a cross sectional view in X-Y plane perpendicular to an optical axis (perpendicular to the drawing surface) OA1. The X and Y-axes are perpendicular to each other.

The electro-static deflector has a pair of electrodes (electro-static deflection electrodes) 7251 in a vacuum to create a electric field in the X direction. The electro-static deflection electrodes 7251 are mounted on an inside wall 7253 of the vacuum via isolation spacers 7252, the distance Dp therebetween is set to be smaller than a length 2L of the electro-static deflection electrodes in the Y direction. By setting the above, a range where a strength of the electric field around the Z-axis or the optical axis is substantially constant may be made wide. However, ideally, it is better to set Dp<L to create a more wider range having a constant strength electric field.

In particular, the strength of the electric field is not constant in a range of Dp/2 from the end of the electrode. Therefore, the range where a strength of the electric field is constant is represented by 2L-Dp which is a center potion of the electrode, excluding the non-constant regions. Accordingly, in order to create a range where the strength electric field is constant, it is necessary to settle to satisfy 2L>Dp, and it is more preferable to set L>Dp to create a broader range thereof.

The electromagnetic deflector for creating a magnetic field in the Y direction is provided outside the vacuum wall 7253. The electromagnetic deflector comprises electromagnetic coils 7254, 7255, which generate magnetic fields in the X and Y directions. Although only the coil 7255 can provide the magnetic field in the Y direction, the coil for generating the magnetic field in the X direction is also provided to improve the perpendicular character between the electric and magnetic fields. Namely, the component in the -X direction of the magnetic field created by the coil 7254 cancels the component in the +X direction created by the coil 7255 to obtain the improved perpendicular character between the electric and magnetic fields.

Each of the coils for generating the magnetic field consists of two parts to be installed outside the vacuum wall, which are mounted on the surface of the vacuum wall 7253 from the both sides thereof, and fixedly clamped at portions 7257 with screws or the like.

The most outer layer 7256 of the ExB separator is formed as yokes made of Permalloy or ferrite. The most outer layer 7256 consists of two parts, and are mounted on the outer surface of the coil 7255 and fixedly clamped at portions 7257 with screws or the like.

Figure 10B:
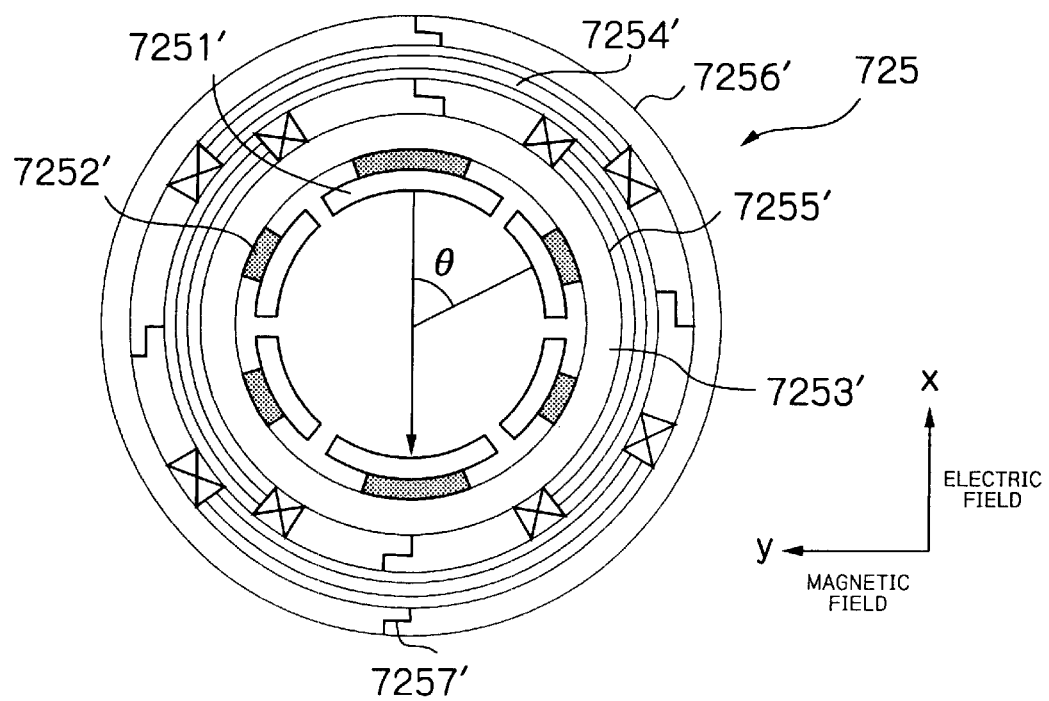

FIG. 10B illustrates another example of the ExB separator applicable to the electro-optical system 70 according to this invention, with a cross sectional view perpendicular to an optical axis. This ExB separator is different to the example shown in FIG. 10A in the point of view that it includes six electro-static deflection electrodes 7251. In FIG. 10B, components of the ExB separator corresponding to those of FIG. 10A are denoted by the same reference numerals with "'", and description thereof is omitted. The electro-static deflection electrodes 7251' are supplied with the voltages k*cosθi (k: constant value), where θi (i=0, 1, 2, 3, 4, 5) is an angle between a line from the electrode center to the optical axis and the electric field direction (X direction)

The ExB separator illustrated in FIG. 10B has coils 7254', 7255' for generating magnetic fields in the X and Y directions to control the perpendicular character, similar to that in FIG. 10A.

The ExB separator shown in FIG. 10B can provide a wider range where the electric field strength is constant, in comparison with that in FIG. 10A.

The coils for generating the magnetic fields are of a saddle-shaped type in the ExB separators illustrated in FIGS. 10A and 10B. However, a coil of a troidal type can also be employed. Further, the ExB separators shown in FIG. 10 can be applied to embodiments of the electron beam apparatuses explained below as well as the electron beam apparatus 70 shown in FIG. 8.

Returning to FIG. 8, the images of the secondary electron beams focussed at the point P3 are again focussed at respective corresponding apertures 743a of the multi-aperture detection plate 743 by through the magnification lenses 741, 742, and detected the detectors 761 correspondingly located to the apertures 743a. The detectors 761 convert the detected beams to electric signals representing the strength of the beams. The electric signals are converted to digital signals at the A/D converters 762 and inputted to the image processing unit 763. As the detectors 761, PN junction diodes which directly detect strengths of electron beams, PMT (photo multiplier tubes) which detect strengths of electron beams after converting them to radiation light by a fluorescent plate.

The image processing unit 763 provides image data obtained from the input digital data. The image processing unit 763 receives a scanning signal which is used to deflect the primary electron beams, from the control unit 2 (FIG. 1). Therefore, the image processing unit receives a signal representing positions of irradiated points on the wafer, and hence can produce an image representing the wafer surface. By comparing the image obtained as above with a predetermined reference pattern, the quality of the pattern on the wafer to be evaluated is determined.

Further, by moving the pattern on the wafer to be evaluated to a position near the optical axis of the primary optical system by registration, obtaining a line width evaluation signal by line-scanning, and by calibrating it, a line width of a pattern on the wafer surface can be detected.

In a prior electron beam apparatus, secondary electrons which are generated when primary electron beams are irradiated on a wafer, are focussed to a point via two steps lenses common to the primary electrons, are deflected by an ExB separator 725 located at the focal point, and are imaged at multiple detectors without passing any lens. As to the common lenses of the primary and secondary optical systems, since it is required to adjust a lens conditions of the primary optical system prior to that of the secondary optical system, a focal condition and enlarging rate of the secondary optical system cannot be controlled. Therefore, the focal condition and enlarging rate thereof cannot be sufficiently adjusted when they are incorrect.

On the other hand, in the present invention, after the secondary electrons are deflected by the ExB separator 725, they are enlarged by the lens of the secondary optical system, a focal condition and enlarging rate can be adjustable apart from a lens condition setting of the primary optical system.

After the primary electron beams pass through the apertures of the multi-aperture plate 723 of the primary optical system, they are focussed on the wafer W, and thereby the secondary electrons are emitted from the wafer. The secondary electron beams are then imaged at the detectors 761. In this event, it is necessary to minimize three aberration effects which are distortion, axial chromatic aberration, and field astigmatism derived in the primary optical system.

In particular, in the case where optical paths of the primary and secondary electron beams are partially common, since primary electron streams and secondary electron streams flow through the common optical path, a beam current having 2 times flows, and thus peculiar in the focal condition of the primary electron beam caused by a space charge effect is two times. Also, it is difficult to adjust the axes of the primary and secondary electron beams in the common optical path. That is, when an adjustment of the axis of the primary electron beams, the axis of the secondary electron beams may be out of their condition, and when an adjustment of an axis of the secondary electron beams, the axis of the primary electron beams may be out of their condition. Further, in the common optical path, when the lens is adjusted to satisfy a focal condition of the primary electron beams, a focal condition of the secondary electron beams may be out of the condition, and the focal condition of the secondary electron beams is adjusted, the focal condition of the primary electron beams may be out of the condition.

Therefore, it is better to design the common path as short as possible. However, when an ExB separator 725 is installed at a position under an objective lens 726, this occurs a problem that an image plan distance of the objective lens is longer, and thereby aberrations are larger. In the present invention, the ExB separator 725 is installed at a side of the electron gun 721 with respect to the objective lens, resulting in that the primary and secondary optical systems commonly employ only a single lens.

In addition, as to relationships between spaces among the primary electron beams and the secondary optical system, when the primary electron beams are spaced to each other by a distance larger than the aberration of the secondary optical system to reduce cross-talk between the beams.

Further, it is preferable to set an deflection angle of the electro-static deflector 727 to be $-\frac{1}{2}$ of an electromagnetic deflection angle by the electromagnetic deflector of the ExB separator 725. Since the chromatic aberration of deflection may be small by setting above, a beam diameter of the beam may be made relatively small even the beam passes the ExB separator.

Pre-charge Unit 81

The pre-charge unit 81, as illustrated in FIG. 1, is disposed adjacent to the column 71 of the electro-optical system 70 within the working chamber 31. Since this evaluation system 1 is configured to test a wafer for device patterns or the like formed on the surface thereof by irradiating the wafer with electron beams, the surface of the wafer may be charged up depending on conditions such as the wafer material, energy of the irradiated electrons, and so on. Further, even on the surface of a single wafer, some regions may be highly charged, while the other regions may be lowly charged. Variations in the amount of charge on the surface of the wafer would cause corresponding variations in information provided by the resulting secondary electrons, thereby failing to acquire correct information. For preventing such variations, in this embodiment, the pre-charge unit 81 is provided with a charged particle irradiating unit 811. Before testing electrons are irradiated to a predetermined region on a wafer, charged particles are irradiated from the charged particle irradiating unit 811 of the pre-charge unit 81 to eliminate variations in charge. The charges on the surface of the wafer previously form an image of the surface of the wafer, which image is evaluated to detect possible variations in charge to operate the pre-charge unit 81 based on the detection. Alternatively, the pre-charge unit 81 may irradiate a blurred primary electron beam.

In a method of detecting an electrical defect of a wafer, it is capable to utilize such a phenomenon that when there are electrically isolated and conductive portions on the wafer, voltages of the portions are different to each other. In order that, a wafer is pre-charged to cause a difference in potential between portions which are intended to be electrically isolated, provided that one of them is conductive in fact, and then electron beams are irradiated on the wafer to detect the voltage difference therebetween. By analyzing the detected data, the conductive portion which is intended to be isolated can be detected.

In such a method of detecting an electrical defect, the pre-charge unit 81 can be employed to pre-charge a wafer.

Potential Applying Unit 83

Figure 11:
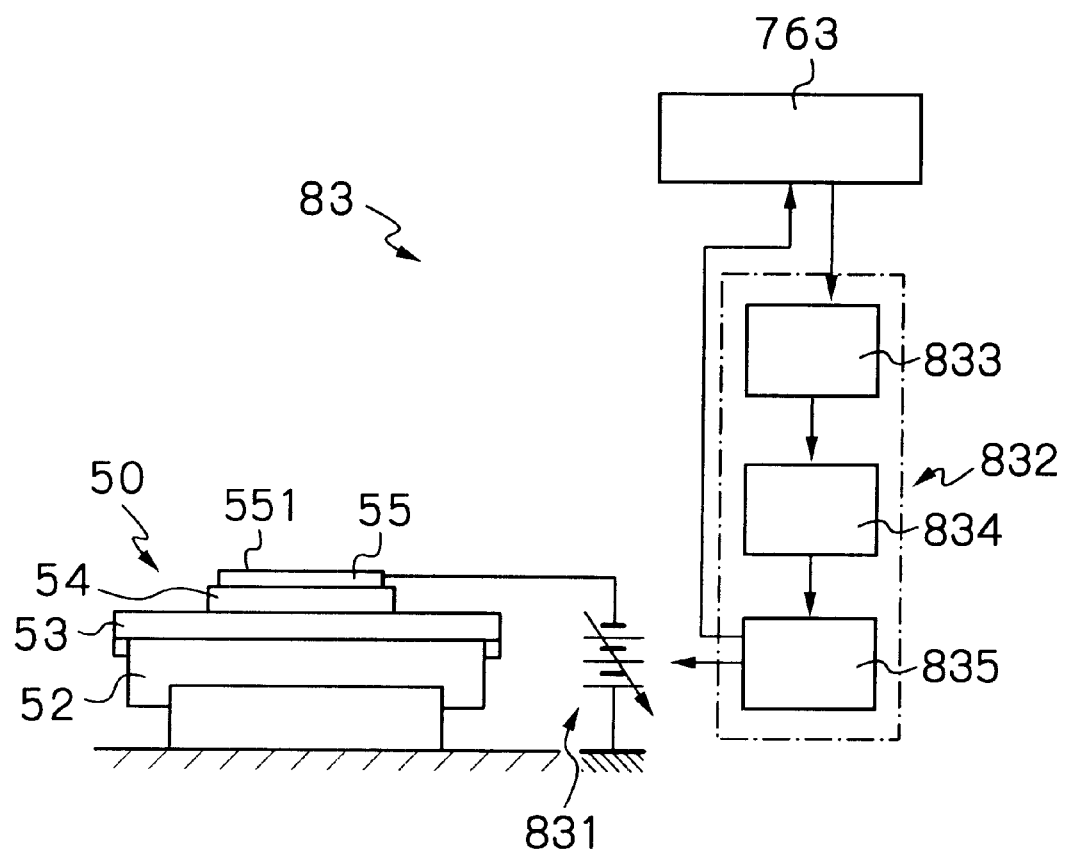
FIG. 11 illustrates a potential application system applicable to the electron beam apparatus concerning the present invention.

FIG. 11 shows a constitution of the potential applying mechanism 83. The mechanism 83 applies a potential of i several volts to a carrier of a stage, on which the wafer is placed, to control the generation of secondary electrons based on the fact that the information on the secondary electrons emitted from the wafer (secondary electron yield) depend on the potential on the wafer. The potential applying mechanism 83 also serves to decelerate the energy originally possessed by irradiated electrons to provide the wafer with irradiated electron energy of approximately 100 to 500 eV.

As illustrated in FIG. 11, the potential applying mechanism 83 comprises a voltage applying device 831 electrically connected to the carrying surface 551 of the stage apparatus 50; and a charge-up examining/voltage determining system (hereinafter examining/determining system) 832. The examining/determining system 832 comprises a monitor 833 electrically connected to an image processing unit 763 of the detecting system 76 in the electro-optical system 70; an operator 834 connected to the monitor 833; and a CPU 835 connected to the operator 834. The CPU 835 is incorporated in the control unit 2 (FIG. 1), and supplies a voltage control signal to the voltage applying device 831. The CPU 835 further provides some components of the electron system with control signals. For instance, it applies a scanning signal to the deflector 727 (FIG. 8) of the electro-optical system 70. In the potential applying mechanism 83, the monitor 833 displays an image reproduced by the image processing unit 763. By studying the image, an operator can search, using an operation input unit 834 and CPU 835, a potential at which the wafer is hardly charged, and control the potential applying device 831 to provide the potential to the holder 55 of the stage apparatus 50.

Electron Beam Calibration Mechanism 85

Figure 12A:
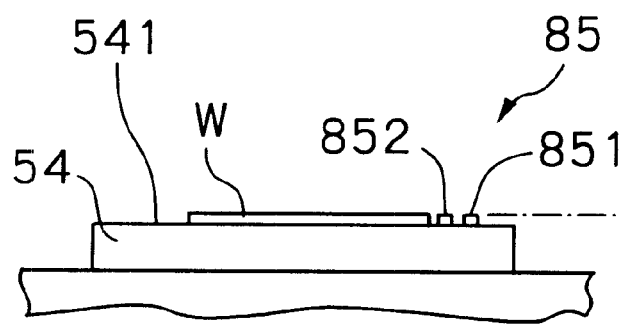
Figure 12B:
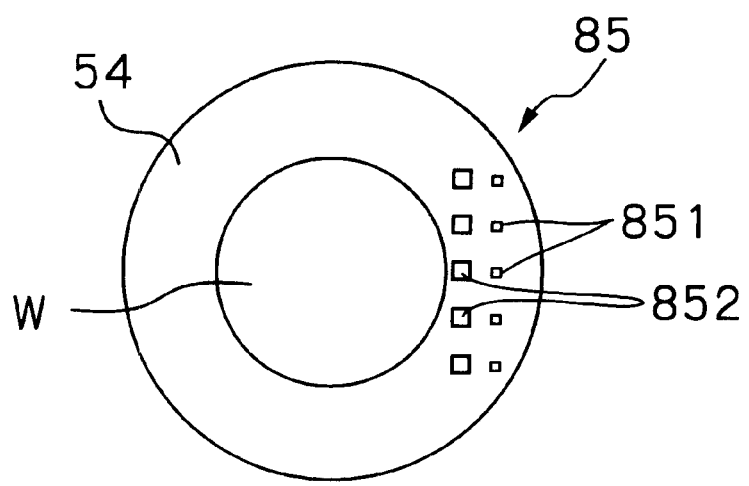

As illustrated in FIGS. 12A and 12B, the electron beam calibration mechanism 85 comprises a plurality of Faraday cups 851, 852 for measuring a beam current, disposed at a plurality of positions in a lateral region of the wafer carrying surface 541 on the turntable 54. The Faraday cups 851 are provided for a narrow beam (approximately $\phi=2$ $\mu$m), while the Faraday cups 852 for a wide beam (approximately $\phi=30$ $\mu$m). The Faraday cuts 851 for a narrow beam measure a beam profile by driving the turntable 54 step by step, while the Faraday cups 852 for a wide beam measure a total amount of currents. The Faraday cups 851, 852 are mounted on the wafer carrying surface 541 such that their top surfaces are coplanar with the upper surface of the wafer W carried on the carrying surface 541. In this way, the primary electron beam emitted from the electron gun is monitored at all times, and a voltage to the electron gun is controlled so that the strength of the electron beams applied at the wafer W is substantially constant. That is, since electron guns cannot emit a constant electron beams at all times but varies in the emission current as it is used over time, the electron beam strength is calibrated by the calibration mechanism.

Alignment Controller 87

The alignment controller 87 aligns the wafer W with the electro-optical system 70 using the stage apparatus 50. The alignment controller 87 performs the control for rough alignment through wide field observation using the optical microscope 871 (a measurement with a lower magnification than a measurement made by the electro-optical system); high magnification alignment using the electro-optical system of the electro-optical system 70; focus adjustment; testing region setting; pattern alignment; and so on. The wafer is tested at a low magnification in this way because an alignment mark must be readily detected by an electron beam when the wafer is aligned by observing patterns on the wafer in a narrow field using the electron beam for automatically testing the wafer for patterns thereon.

The optical microscope 871 is disposed on the housing 30. Alternatively, it may be movably disposed within the Ad housing 30. A light source (not shown) for operating the optical microscope 871 is additionally disposed within the housing 30. The electro-optical system for observing the wafer at a high magnification, shares the electro-optical systems (primary optical system 72 and secondary optical system 74) of the electro-optical system 70.

Figure 13:
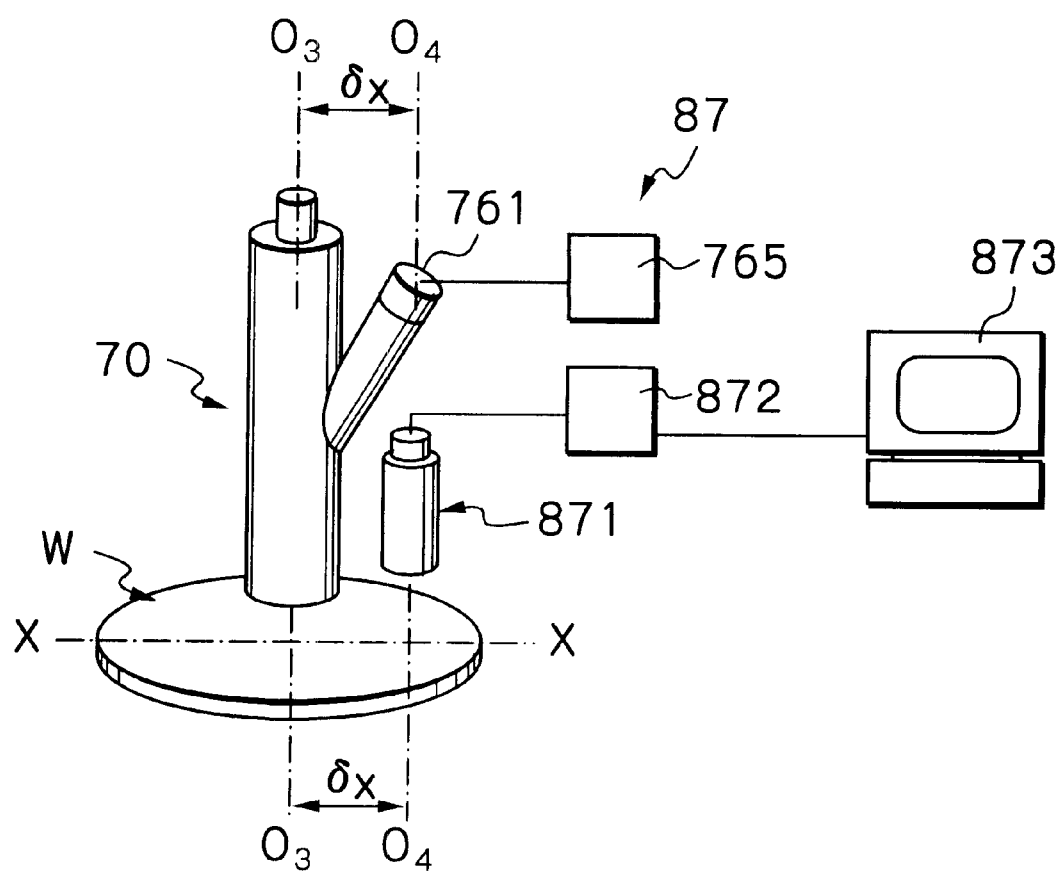
FIG. 13 schematically illustrates a device for controlling an alignment of wafers, which is applicable to the electron beam apparatus concerning the present invention.

The configuration of the alignment controller 87 may be generally illustrated in FIG. 13. For observing a point of interest on a wafer at a low magnification, the X-stage or Y-stage of the stage apparatus 50 is controlled to move the point of interest on the wafer into a field of the optical microscope 871. The wafer is studied in a wide field by the optical microscope 871, and the point of interest on the wafer to be observed is displayed on a monitor 873 through a CCD 872 to roughly determine a position to be observed. In this event, the magnification of the optical microscope may be changed from a low magnification to a high magnification.

Next, the stage apparatus 50 is moved by a distance corresponding to a spacing äx between the optical axis of the electro-optical system 70 and the optical axis of the optical microscope 871 to move the point on the wafer under observation, previously determined by the optical microscope 871, to a point in the field of the electro-optical system 70. In this event, since the distance δx between the axis $O_3$—$O_3$ of the electro-optical system and the axis $O_4$—$O_4$ of the optical microscope 871 is previously known (while it is assumed that the electro-optical system 70 is deviated from the optical microscope 871 in the direction along the X-axis in this embodiment, they may be deviated in the Y direction as well as in the X direction), the point under observation can be moved to the viewing position by moving the stage apparatus 50 by the distance δx. After the point under observation has been moved to the viewing position of the electro-optical system 70, the point under observation is imaged by the electro-optical system at a high magnification for storing a resulting image or displaying the image on the monitor 765.

After the point under observation on the wafer imaged by the electro-optical system at a high magnification is displayed on the monitor, misalignment of the stage apparatus 50 with respect to the center of rotation of the turntable 54 in the wafer rotating direction, or misalignment δθ of the wafer in the wafer rotating direction with respect to the optical axis $O_3$—$O_3$ of the electro-optical system 70 are detected in a conventional method. Then, the operation of the stage apparatus 50 is controlled to align the wafer, based on the detected values and data on a testing mark attached on the wafer, or data on the shape of the patterns on the wafer which have been acquired in separation.

Controller 2

The controller mainly comprises a main controller, a control controller and a stage controller.

The main controller has a man-machine interface through which the operation by an operator (input of various instructions/commands and menus, instruction to start a test, switch between automatic and manual test modes, input of all commands necessary when the manual test mode) is performed. Further, the main controller performs a communication to a host computer in a factory, control of a vacuum evacuation system, carriage of a sample such as a wafer, control of alignment, transmission of commands to the control controller and the stage controller and receipt of information. Moreover, the main controller has a function of obtaining an image signal from the optical microscope, a stage vibration correcting function for feeding back a vibration signal of the stage to the electro-optical system to correct a deteriorated image, and an automatic focus correcting function for detecting a Z-direction (the direction of the axis of the primary optical system) displacement of a sample observing position to feed back the displacement to the electro-optical system so as to automatically correct the focus. Reception and transmission of a feedback signal to the electro-optical system and a signal from the stage can be performed through the control controller and the stage controller.

The control controller is mainly responsible for control of the electro-optical system, or control of highly accurate voltage sources for electron gun, lenses, aligner and Wien filter). Specifically, the control controller effects control (gang control) of automatic voltage setting to each lens system and the aligner in correspondence with each operation mode, for example, causes a region to be irradiated by a constant electron current even if the magnification is changed, and automatically sets a voltage applied to each lens system and the aligner in correspondence with each magnification.

The stage controller is mainly responsible for control regarding the movement of the stage and enables the achievement of accurate X and Y-direction movements of micrometer order (tolerance: ±0.5 micrometer). Further, the stage controller achieves control of rotation (θ control) of the stage within an error accuracy of ±0.3 seconds.

The evaluating system according to the invention as described above, can functionally combine the electron beam apparatus of a multi-beam type with the respective components of the evaluation system, resulting in that samples can be evaluated with a high throughput. If a sensor for detecting a clean level of the environment housing, it is possible to test samples while monitoring refuses in the housing. Further, since the pre-charge unit is provided, a wafer made of an insulation material may not be affected from charging.

Some embodiments of a combination of a stage apparatus 50 and a charged particle beam irradiation portion of a electro-optical system 70 in the electron beam apparatus accommodated in the evaluation system 1 according to the present invention.

When testing a sample such as a semiconductor wafer possessed with ultra accurate processing, a stage apparatus 50 which is capable of accurately positioning the wafer in a vacuum working chamber 31, is required. As such a stage apparatus usable in such a case that ultra accurately positioning is required, a mechanism for supporting X-Y stage with a hydrostatic bearings with a non-contact manner, is employed. In this event, a degree of vacuum is maintained in the vacuum chamber or working chamber 31 by forming a differential pumping mechanism for pumping a high pressure gas in a range of the hydrostatic bearing so that the high pressure gas supplied from the hydrostatic bearings will not be pumped directly to the working chamber 31. In the description, the term "vacuum" means a vacuum condition so-called in this field.

Figure 14A:
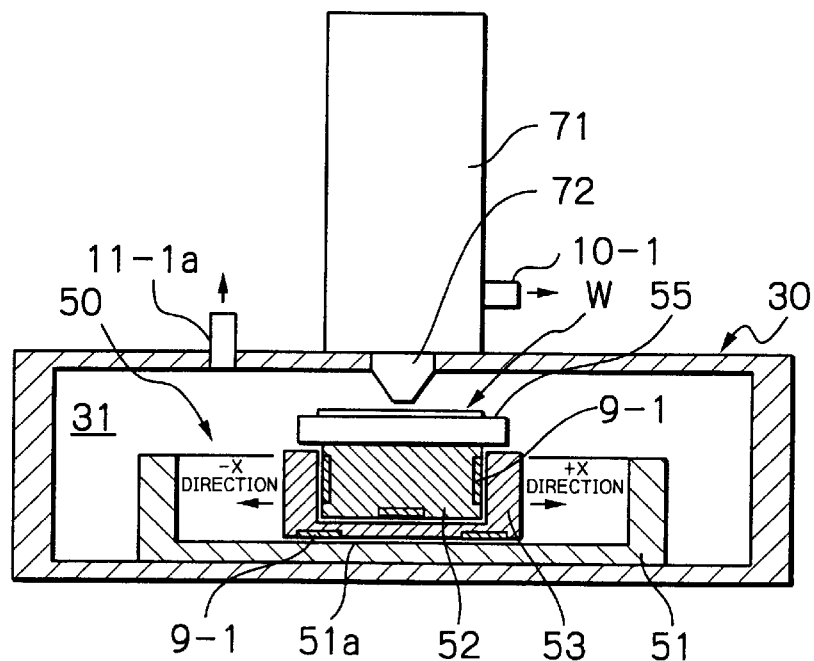
FIGS. 14A and 14B illustrate, a relationship between an X-Y stage and a charged particle beam irradiation means of an electron optical system in a conventional electron beam apparatus.
Figure 14B:
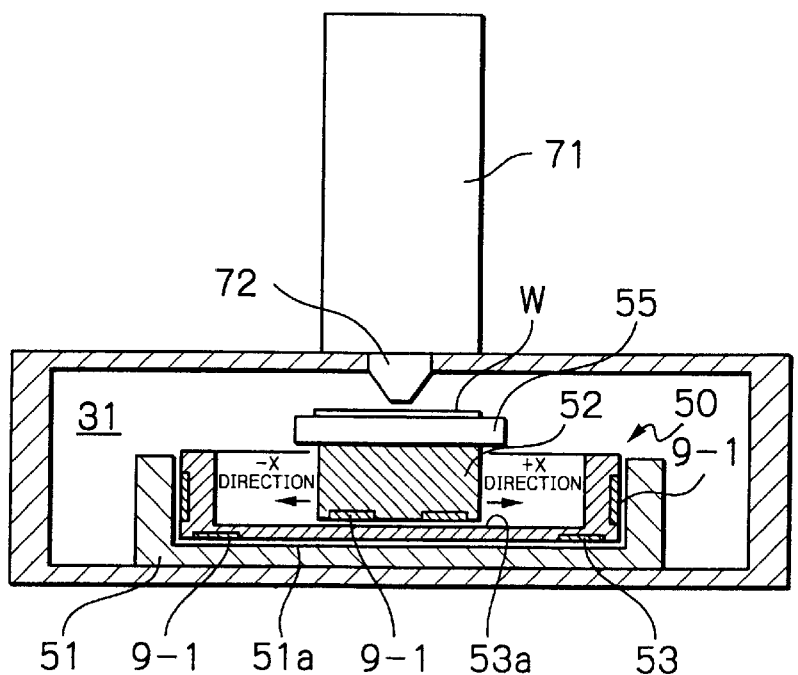

An example of the combination of a stage apparatus and electro-optical system 70 according to the prior art is illustrated in FIG. 14. FIGS. 14A and 14B are elevation and side views, respectively. In the prior art, a bottom of a column 71 of an electron beam apparatus for generating an electron beam to irradiate a wafer, i.e., an electron beam emitting tip 72 is attached to a main housing 30 which constitutes a vacuum chamber 31. The inside of the column 71 is evacuated to vacuum by a vacuum pipe 10-1, and the chamber 31 is evacuated to a vacuum by a vacuum pipe 11-1a. Then, electron beam is emitted from the bottom 72 of the column 71 to a sample such as a wafer W placed therebelow.

The wafer W is removably held on a holder 55 in a known method. The holder 55 is mounted on the top surface of a Y-table 52 of an X-Y stage. The Y-table 52 has a plurality of hydrostatic bearings 9-1 attached on surfaces (both left and right side surfaces and a lower surface in FIG. 14A) opposite to a guide surface of an X-table 53. The Y-table 52 is movable in the Y-direction (in the left-to-right direction in FIG. 12B), while maintaining a small gap between the guide surface and the opposite surfaces by the action of the hydrostatic bearings 9-1. Further, around the hydrostatic bearings 9-1, a differential pumping mechanism is disposed to prevent a high pressure gas supplied to the hydrostatic bearings 9-1 from leaking into the inside of the vacuum chamber 31. This situation is shown in FIG. 15.

Figure 15:
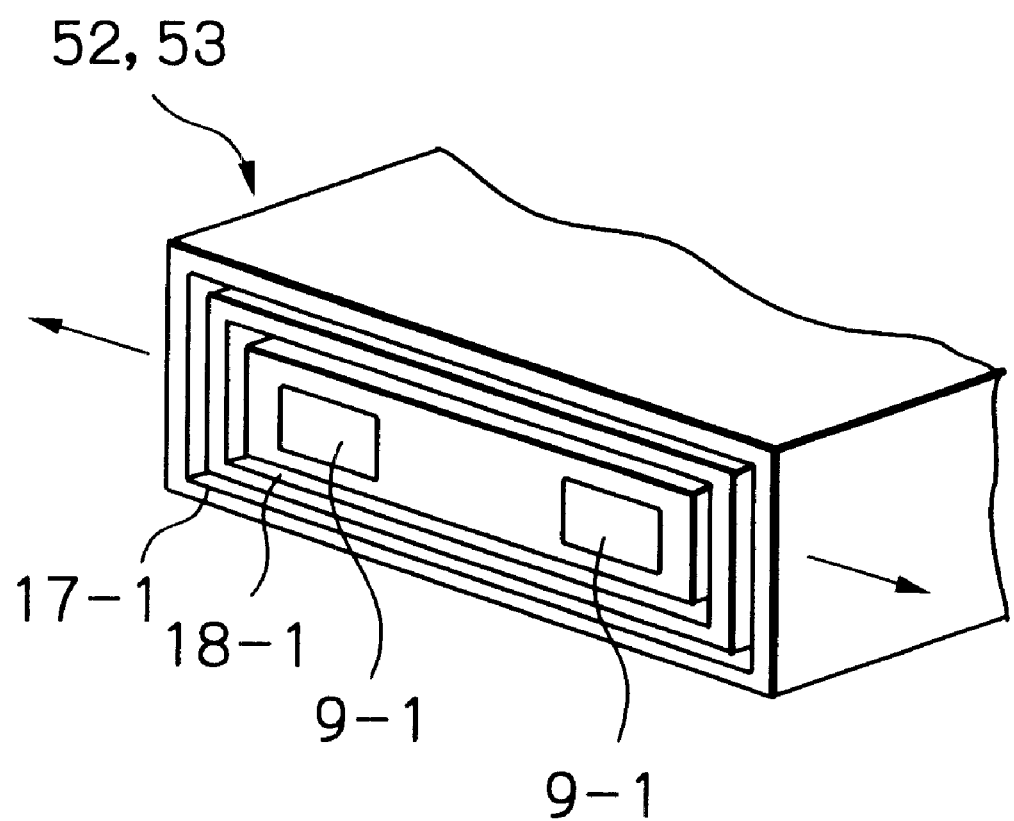
FIG. 15 illustrates the state of the bottom of the X-Y stage indicated in FIG. 14.

As illustrated in FIG. 15, double grooves 18-1 and 17-1 are formed around the hydrostatic bearings 9-1, and these grooves are evacuated to vacuum at all times by a vacuum pipe and a vacuum pump, not shown. With such a structure, the Y-table 52 is supported in a non-contact state in vacuum so that it is freely movable in the Y-direction. These double grooves 18-1 and 17-1 are formed to surround the hydrostatic bearings 9-1 of the Y-table 52, on the surface on which the hydrostatic bearings are disposed. Since the hydrostatic bearing may have a known structure, detailed description thereon is omitted.

The X-table 53, which carries the Y-table 52 has a concave shape open directed upwardly, as is apparent from FIG. 14. The X-table 53 is also provided with completely similar hydrostatic bearings and grooves, such that the X-table 53 is supported to a stage stand or fixed table 51 in a non-contact manner, and is freely movable in the X-direction.

By combining movements of these Y-table 52 and X-table 53, it is possible to move the wafer W to an arbitrary position in the horizontal direction with respect to the bottom of the column, i.e., the electron beam emitting tip 72 to emit electron beams to a desired position of the wafer W.

In the combination of the stage apparatus 50 and the electron beam emitting tip 72 can be employed in the evaluation system according to the present invention. However, there are problems below.

In the prior combination of the hydrostatic bearings 9-1 and the differential pumping mechanism, the guide surfaces 53a, 51a opposing to the hydrostatic bearings 9-1 reciprocate between a high pressure gas atmosphere around the hydrostatic bearings and a vacuum environment within the working chamber 31 as the X-Y stage is moved. In this event, while the guide surfaces are exposed to the high pressure gas atmosphere, the gas is adsorbed to the guide surfaces, and the adsorbed gas is released as the guide surfaces are exposed to the vacuum environment. Such states are repeated. Therefore, as the X-Y stage is moved, the degree of vacuum within the working chamber 31 is degraded, rising a problem that the aforementioned processing such as exposure, testing and working, by use of the electron beam cannot be stably performed and that the wafer is contaminated.

Figure 16A:
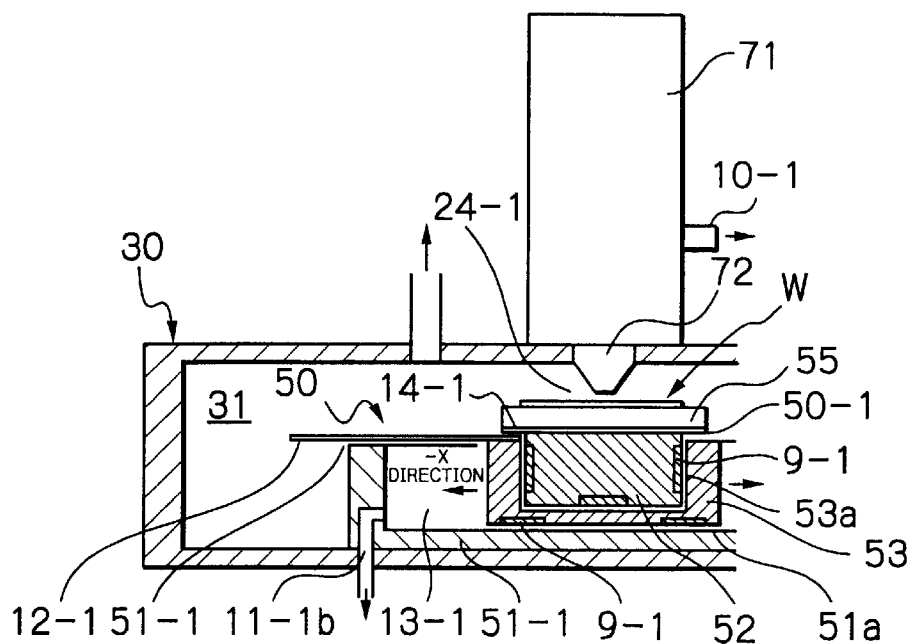
FIGS. 16A and 16B illustrates a relationship between an X-Y stage and a charged particle beam irradiation means of an electron optical system according to an embodiment of an electron beam apparatus of the present invention.
Figure 16B:
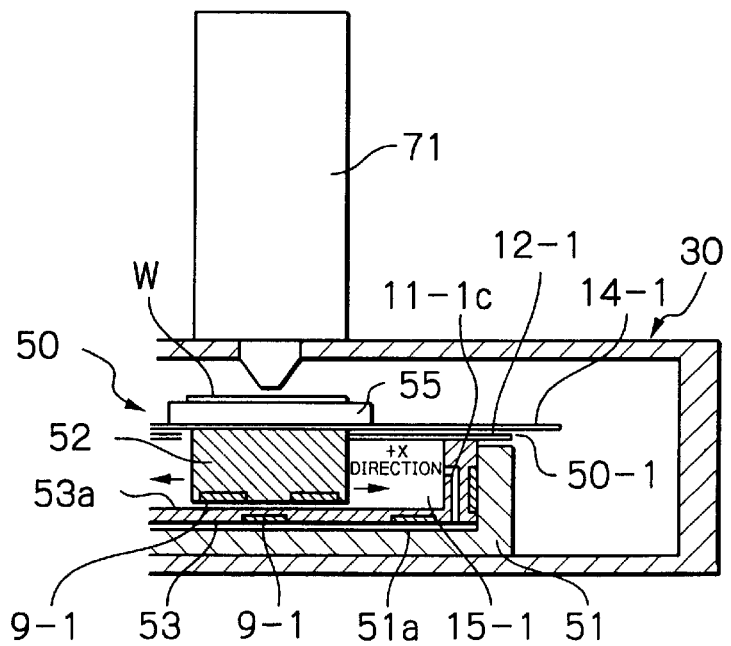

Therefore, an apparatus is required which prevents the degree of vacuum from degrading to permit stable processing such as testing and working by use of an electron beam. FIG. 16 shows an embodiment of the combination of the stage apparatus 50 and the electron beam emitting tip 72 of an electro-optical system 70, which can derive advantages above. In FIG. 16, FIGS. 16A and 16B are front and side views, respectively.

As illustrated in FIG. 16, a partition plate 14-1 largely extending substantially horizontally in the ±Y directions (in the left and right directions in FIG. 16B) is attached on the top surface of a Y-table 52, such that a reducer 50-1 having a small conductance is formed at all times between the top surface of the X-table 53 and the partition plate 14-1. Also, on the top surface of an X-table 53, a partition plate 12-1 is placed to extend in the ±X directions (in the left and right directions in FIG. 14A), such that a reducer 51-1 is formed at all time between the top surface of a fixed table 51 and the partition plate 12-1. The fixed table 51 is mounted on a bottom wall in a main housing 30 in a conventional manner.

Thus, since the reducers 50-1 and 51-1 are formed at all times when the wafer table or holder 55 is moved to whichever position, so that even if a gas is released from the guide surfaces 53a and 51a while the Y-table 52 and X-table 53 are moved, the movement of the released gas is prevented by the reducers 50-1 and 51-1. Therefore, it is possible to significantly suppress an increase in pressure in a space 24-1 near the wafer irradiated with electron beams.

The side and lower surfaces of the movable section or Y-table 52 and the lower surface of the X-table 53 of the stage apparatus 50 are formed with grooves, around the hydrostatic bearings 9-1, for differential pumping, as illustrated in FIG. 15. Since evacuation to vacuum is performed through these grooves, the released gas from the guide surfaces are mainly pumped by these differential pumping mechanism when the reducers 1550, 1551 are formed. Therefore, the pressures in the spaces 13-1 and 15-1 within the stage apparatus 50 are higher than the pressure within the working chamber 30. Therefore, if locations which are evacuated to vacuum are separately provided, not only the spaces 13-1 and 15-1 are evacuated through the differential pumping grooves 17-1 and 18-1, but also the pressures in the spaces 13-1 and 15-1 can be reduced to further suppress an increase in pressure near the wafer W. Vacuum evacuation passages 11-1b and 11-1c are provided for this purpose. The evacuation passage 11-1b extends through the fixed table 51 and the main housing 30 and communicates with the outside of the housing 30. The evacuation passage 11-1c is formed in the X-table 53 and opened to the lower surface of the X-table.

While the provision of the partition plates 12-1 and 14-1 results in a requirement of increasing the size of the working chamber 30 such that the chamber 30 does not interfere with the partition walls, this aspect can be improved by making the partition plates of a retractile material or in a telescopical structure. In such an improved embodiment, the partition wall is made of rubber or in bellows form, and its end in the moving direction is fixed to the X-table 53 for the partition plate 14-1, and to an inner wall of the housing 8 for the partition plate 12-1, respectively.

Figure 17:
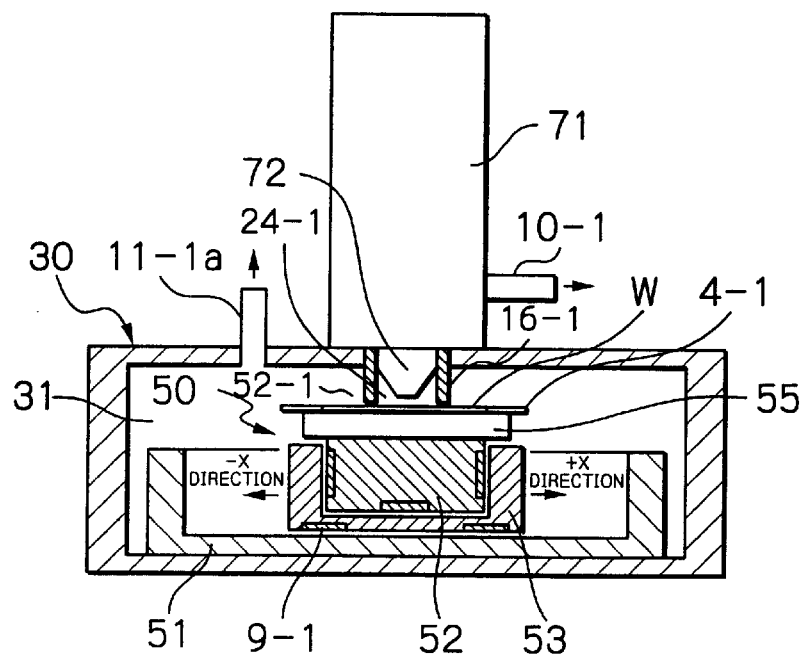
FIG. 17 illustrates a relationship between an X-Y stage and a charged particle beam irradiation means of an electron optical system according to another embodiment of an electron beam apparatus of the present invention.

FIG. 17 illustrates another embodiment of the combination of the stage apparatus 50 and the electron emitting tip 72 of the electro-optical system 70. In the example, a cylindrical partition 16-1 is formed around the bottom of the column 71, i.e., the electron beam emitting tip 72 to provide a reducer between the top surface of the wafer W and the electron beam emitting tip 72. In such a configuration, even if a gas is released from the X-Y stage to cause an increased pressure within the working chamber 31, a pressure difference is produced between the inside of the chamber C and the inside 1524 of the partition, because the inside 24-1 of the partition is partitioned by the partition 16-1 and the gas is pumped through the vacuum pipe 10-1. Therefore, an increased pressure within the space 24-1 in the partition may be suppressed. While a gap between the partition 16-1 and the surface of the wafer W should be settled depending on the pressure maintained within the working chamber 31 and around the emitting tip 72, approximately several tens of μm to several mm are proper. The inside of the partition 16-1 is communicated with the vacuum pipe 10-1 by a conventional method.

Also, since electron beam apparatus may apply a wafer W with a high voltage of approximately several kV, a conductive material placed near the wafer gives rise to a discharge. In this case, the partition 16-1 may be made of an insulating material such as ceramics to prevent a discharge between the wafer W and the partition 16-1.

A ring member 4-1 disposed around the wafer W is a plate-shaped adjusting part fixed to the wafer base or holder 55, which is set at the same level as the wafer such that a small gap 25-1 is formed over the entire periphery of the bottom of the partition 16-1. Therefore, even when electron beams are irradiated to whichever position of the wafer W, the constant small gap 52-1 is formed at all times at the bottom of the partition 16-1, thereby making it possible to stably maintain the pressure in the space 24-1 around the bottom of the column 71.

Figure 18:
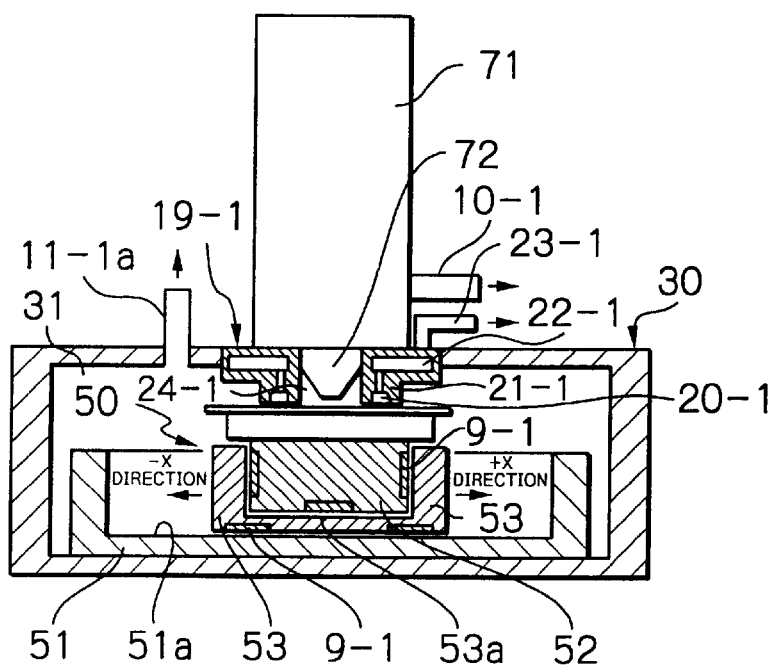
FIG. 18 illustrates a relationship between an X-Y stage and a charged particle beam irradiation means of an electron optical system according to still another embodiment of an electron beam apparatus of the present invention.

FIG. 18 illustrates a still another embodiment of the combination of the stage apparatus 50 and the electron beam emitting tip 72 of the electron beam apparatus. A partition 19-1 containing a differential pumping structure is disposed around an electron beam emitting tip 72 of the column 71. The partition 19-1 has a cylindrical shape, and a circumferential groove 20-1 is formed inside. An pumping passage 21-1 extends upward from the circumferential grove. The pumping passage is connected to a vacuum pipe 23-1 through an internal space 22-1. There is a small gap ranging from several tens of μm to several mm between the lower end of the partition wall 19-1 and the upper surface of the wafer W.

In the configuration shown in FIG. 18, even if a gas is released from the stage apparatus 50 in association with a movement of the X-Y stage to cause an increased pressure within a working chamber 30, and the gas is going to flow into the electron beam emitting tip 72, the partition 19-1 reduces the gap between the wafer W and the tip to make the conductance extremely small. Therefore, the gas is impeded from flowing into the electron beam emitting tip 72 and the amount of flowing gas is reduced. Further, the introduced gas is pumped from the circumferential groove 20-1 to the vacuum pipe 1523, so that substantially no gas flows into the space 24-1 around the electron beam emitting tip 72, thereby making it possible to maintain the pressure around the electron beam emitting tip 72 at a desired high vacuum.

Figure 19:
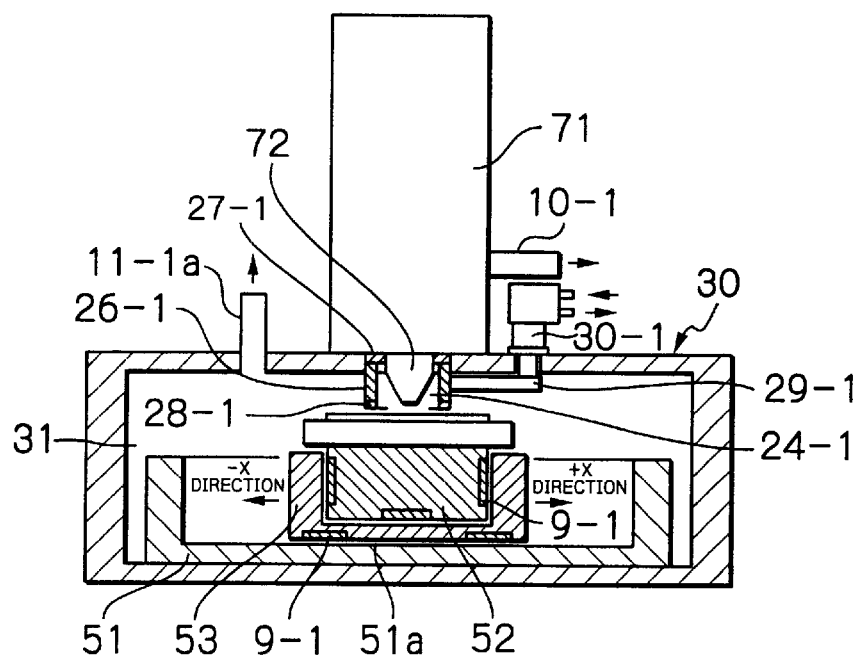
FIG. 19 illustrates a relationship between an X-Y stage and a charged particle beam irradiation means of an electron optical system according to further another embodiment of an electron beam apparatus of the present invention.

FIG. 19 illustrates another embodiment of the combination of the stage apparatus 50 and the electron beam emitting tip 72 of the electro-optical system 70. In this embodiment, a partition 26-1 is formed around the electron beam emitting tip 72 in the working chamber 31 to separate the electron beam emitting tip 72 from the chamber 31. This partition 26-1 is coupled to a freezer 30-1 through a supporting member 29-1 made of a high thermally conductive material such as copper or aluminum, and is cooled at −100° C. to −200° C. A member 27-1 is provided for preventing thermal conduction between the cooled partition 26-1 and the column 71, and is made of a low thermally conductive material such as ceramics resin material. Also, a member 28-1, which is made of a non-insulating material such as ceramics, is formed at a lower end of the partition 26-1 for preventing the wafer W and the partition 26-1 from discharging therebetween.

In the configuration shown in FIG. 19, gas molecules which are going to flow from the working chamber 31 into the electron beam emitting tip 72 are impeded by the partition 26-1 from flowing toward the electron beam emitting tip, and even if the molecules flow, they are frozen and trapped on the surface of the partition 26-1, thereby making it possible to maintain low the pressure in the space around the electron beam emitting tip 72.

As the freezer, a variety of freezers can be used such as a liquid nitrogen based freezer, an He freezer, a pulse tube type freezer, and so on.

Figure 20:
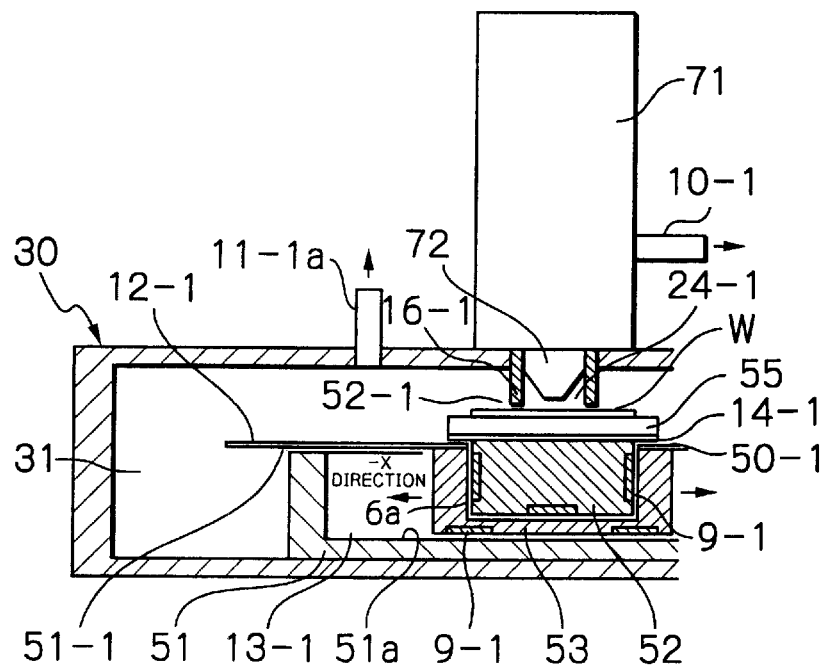
FIG. 20 illustrates a relationship between an X-Y stage and a charged particle beam irradiation means of an electron optical system according to still another embodiment of an electron beam apparatus of the present invention.
Figure 40:
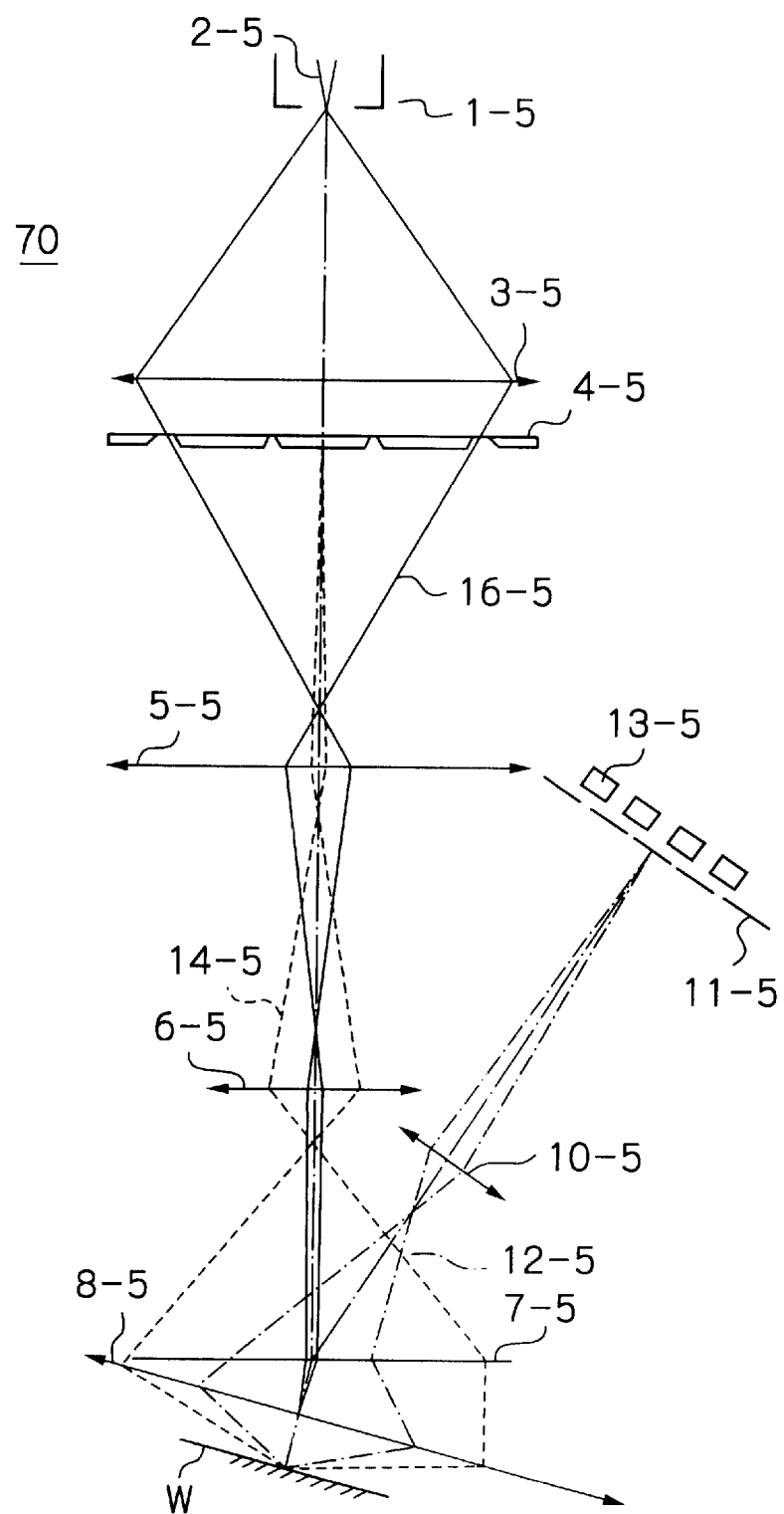
FIG. 40 schematically illustrates another embodiment of an electron beam apparatus according to the present invention.

FIG. 20 illustrates a further embodiment of the combination of the stage apparatus 50 and the electron beam emitting tip 72 of the electro-optical system 70. Similar to the constitution shown in FIG. 16, a partition plates 12-1, 14-1 are disposed on both movable sections of the X-Y stage or Y and X-tables 52, 53. Therefore, even if the sample base or holder 55 is moved to an arbitrary position, the space 13-1 within the stage apparatus and the inside of the working chamber 31 are partitioned by these partitions through reducers 50-1, 51-1. Further, a partition 16-1 similar to that illustrated in FIG. 17 is formed around the electron beam emitting tip 72 to partition the inside of the working chamber 31 and the space 24-1, in which the electron beam emitting tip 72 is positioned, through a reducer 52-1. Therefore, even if a gas adsorbed on the stage is released into the space 13-1 while the stage is moved, to increase the pressure in this space, an increased pressure in the working chamber 31 is suppressed, and an increased pressure in the space 24-1 is further suppressed. In this way, the pressure in the space 24-1 around the electron beam irradiation tip 71 can be maintained in a low state. In addition, the space 24-1 can be stably maintained at a yet lower pressure, by utilizing the partition 19-1 which contains a differential pumping mechanism, or the partition 26-1 cooled by a freezer which is illustrated in FIG. 40, as the partition 16-1.

In this embodiment with regard to the electron beam emitting tip, the stage apparatus can be accurately positioned in the vacuumed working chamber, and the pressure around the irradiation tip is prevented from increasing, resulting in obtaining a high quality image data.

Figure 21:
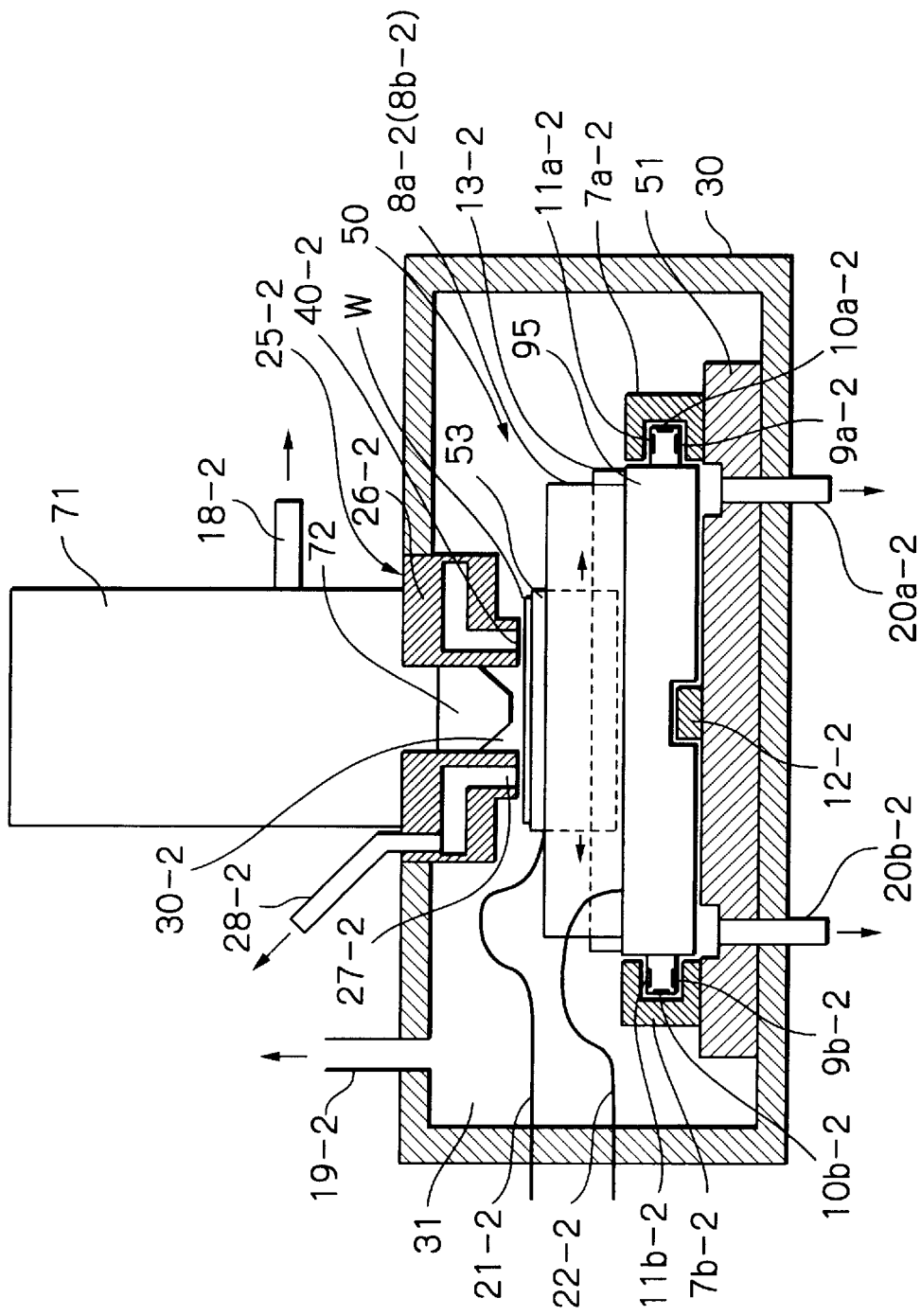
FIG. 21 illustrates a relationship between an X-Y stage and a charged particle beam irradiation means of an electron optical system according to still another embodiment of an electron beam apparatus of the present invention.

FIG. 21 shows a more further embodiment of the combination of the stage apparatus 50 and the electron beam emitting tip 72 of the electro-optical system 70. In this embodiment, a bottom of the column 71, i.e., the electron beam emitting tip 72 is attached to a main housing 30 which defines a working chamber 31. A base or fixed table of the X-Y stage of the stage apparatus 50 is fixed on a bottom wall of the main housing 30, and a Y-table 52 is mounted on the fixed table 51. On both sides of the Y-table 52 (on left and right sides in FIG. 21), protrusions are formed, which are protruding into recessed grooves of a pair of Y-direction guides 7a-2 and 7b-2 carried on the fixed table 51 formed in the sides facing the Y-table. The recessed grooves extend in the Y-direction (the direction perpendicular to the drawing surface) substantially over the entire length of the Y-direction guides. Hydrostatic bearings 11a-2, 9a-2, 11b-2, 9b-2 in a known structure are disposed on the top surface, bottom surface and side surfaces of the protrusions protruding into the recessed grooves, respectively. A high pressure gas is blown off through these hydrostatic bearings to support the Y-table 52 with respect to the Y-direction guides 7a-2, 7b-2 in a non-contact manner and to allow the same to smoothly reciprocate in the Y-direction. Also, a linear motor 12-2 in a known structure is disposed between the pedestal table 51 and the Y-table 52 to drive the Y-table in the Y-direction. The Y-table 52 is supplied with a high pressure gas through a flexible pipe 22-2 for high pressure gas supply, so that the high pressure gas is supplied to the hydrostatic bearings 9a-2 to 11a-2 and 9b-2 to 11b-2 through a gas passage (not shown) formed in the Y-table. The high pressure gas supplied to the hydrostatic bearings blows out into a gap of several microns to several tens of microns formed between opposing guiding surfaces of the Y-direction guide to serve to precisely position the Y-table 52 with respect to the guide surfaces in the X-direction and Z-direction (upward and downward directions in FIG. 21).

An X-table 53 is carried on the Y-table 52 for movement in the X-direction (in the left-to-right direction in FIG. 21). On the Y-table 52, a pair of X-direction guides 8a-2, 8b-2 (only 8a-2 is shown) identical in structure to the Y-direction guides 7a-2, 7b-2 for the Y-table are disposed with the X-table 53 interposed therebetween. A recessed groove is also formed in the side of the X-direction guide facing the X-table 53, and a protrusion is formed in a side portion of the X-table (a side portion facing the X-direction guide), protruding into the recessed groove. The recessed groove extends substantially over the entire length of the X-direction guide. Hydrostatic bearings (not shown) similar to the hydrostatic bearings 11a-2, 9a-2, 10a-2, 11b-2, 9b-2, 10b-2 are disposed on the top surface, bottom surface and side surfaces of the protrusion of the X-table 53 protruding into the recessed groove in similar positioning. Between the Y-table 52 and the X-table 53, a linear motor 13-2 in a known structure is disposed so that the X-table is driven in the X-direction by means of the linear motor. Then, the X-table 53 is supplied with a high pressure gas through a flexible pipe 21-2 to supply the high pressure gas to the hydrostatic bearings. The high pressure gas is blown out from the hydrostatic bearings to the guide surfaces of the X-direction guide to highly accurately support the X-table 53 with respect to the Y-direction guide in a non-contact manner. The vacuum working chamber 31 is evacuated by vacuum pipes 19-2, 20a-2, 20b-2 connected to a vacuum pump or the like in a conventional structure. The inlet sides (within the working chamber) of the pipes 20a-2, 20b-2 extend through the pedestal or fixed table 51 and are open near a position at which the high pressure gas is pumped from the X-Y stage on the top surface of the table 51, to maximally prevent the pressure within the working chamber 31 from rising due to the high pressure gas blown out from the hydrostatic bearings.

A differential pumping mechanism 25-2 is disposed around the electron beam emitting tip 72, so that the pressure in the electron beam irradiation space 30-2 is held sufficiently low even if the pressure in the working chamber 31 is high. Specifically, an annular member 26-2 of the differential pumping mechanism 25-2 attached around the electron beam emitting tip 72 is positioned with respect to the main housing 30 such that a small gap (from several micron to several hundred microns) 40-2 is formed between the lower surface (the surface opposing the wafer W) and the wafer, and an annular groove 27-2 is formed on the lower surface thereof. The annular groove 27-2 is connected to a vacuum pump or the like, not shown, through an pumping pipe 28-2. Therefore, the small gap 40-2 is evacuated through the annular groove 27-2 and an evacuate port 28-2, so that even if gas molecules attempt to invade from the working chamber 31 into the electron beam irradiating space 30-2 surrounded by the annular member 1626, they are pumped. In this way, the pressure within the electron beam irradiation space 30-2 can be held low to irradiate an electron beam without problem.

The annular groove 27-2 may be in a double structure or in a triple structure depending on the pressure within the chamber or the pressure within the electron beam irradiation space 30-2.

For the high pressure gas supplied to the hydrostatic bearings, dry nitrogen is generally used. However, if possible, a highly pure inert gas is further preferable. This is because if impurities such as moisture and oil components are included in the gas, these impurity molecules will attach on the inner surface of the housing which defines the vacuum chamber, and on the surfaces of components of the stage to deteriorate the degree of vacuum, and will attach on the surface of the sample to deteriorate the degree of vacuum in the electron beam irradiation space.

In the foregoing description, the sample or wafer W is not generally carried directly on the X-table 53, but carried on a wafer base or holder which has functions of removably holding the wafer, and making a slight positional change with respect to the X-Y stage, and so on. However, since the presence or absence of the sample base, and its structure are not related to the gist of the present invention, they are omitted for simplifying the description.

Since the electron beam apparatus described above can use a hydrostatic bearing stage mechanism used in the atmosphere as it is, a highly accurate X-Y stage equivalent to a highly accurate stage for atmosphere used in an exposure apparatus and so on can be implemented in an X-Y stage for an electron beam apparatus substantially at the same cost and in the same size.

The structure and positioning of the static pressure guides and actuators (linear motors) described above are merely embodiments in all sense, and any of static pressure guides and actuators can be applied if it is usable in the atmosphere.

Figure 22:
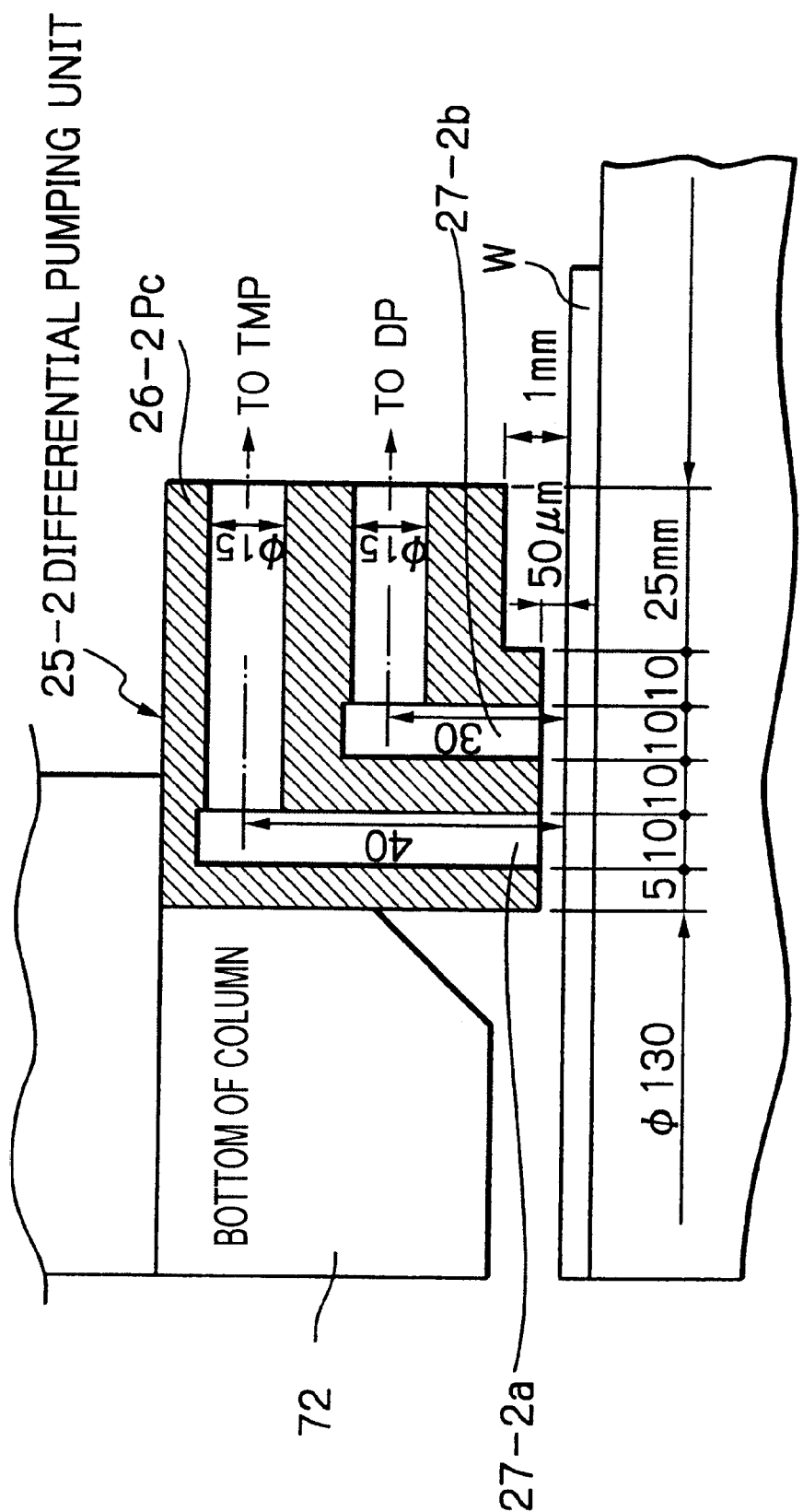
FIG. 22 illustrates an operation emission mechanism installed in the embodiment indicated in FIG. 21.

FIG. 22 shows exemplary values for the sizes of the annular member 26-2 of the differential pumping mechanism, and the annular groove 27-2 formed therein. In this example, the annular groove has a double structure comprised of 27a-2 and 27b-2 which are spaced apart in a radial direction.

A flow rate of the high pressure gas supplied to the hydrostatic bearings is generally at about 20 L/min (converted to the atmospheric pressure). Assuming that the working chamber 31 is evacuated by a dry pump having an pumping speed of 20000 L/min through a vacuum pipe having an inner diameter of 50 mm and a length of 2 m, the pressure in the chamber 31 is approximately 160 Pa (approximately 1.2 Torr). In this event, if the dimensions of the annular member 26-2 of the differential pumping mechanism, annular groove and so on are determined as shown in FIG. 22, the pressure in the electron beam irradiation space 30-2 can be set at 10–4 Pa (10–6 Torr).

Figure 23:
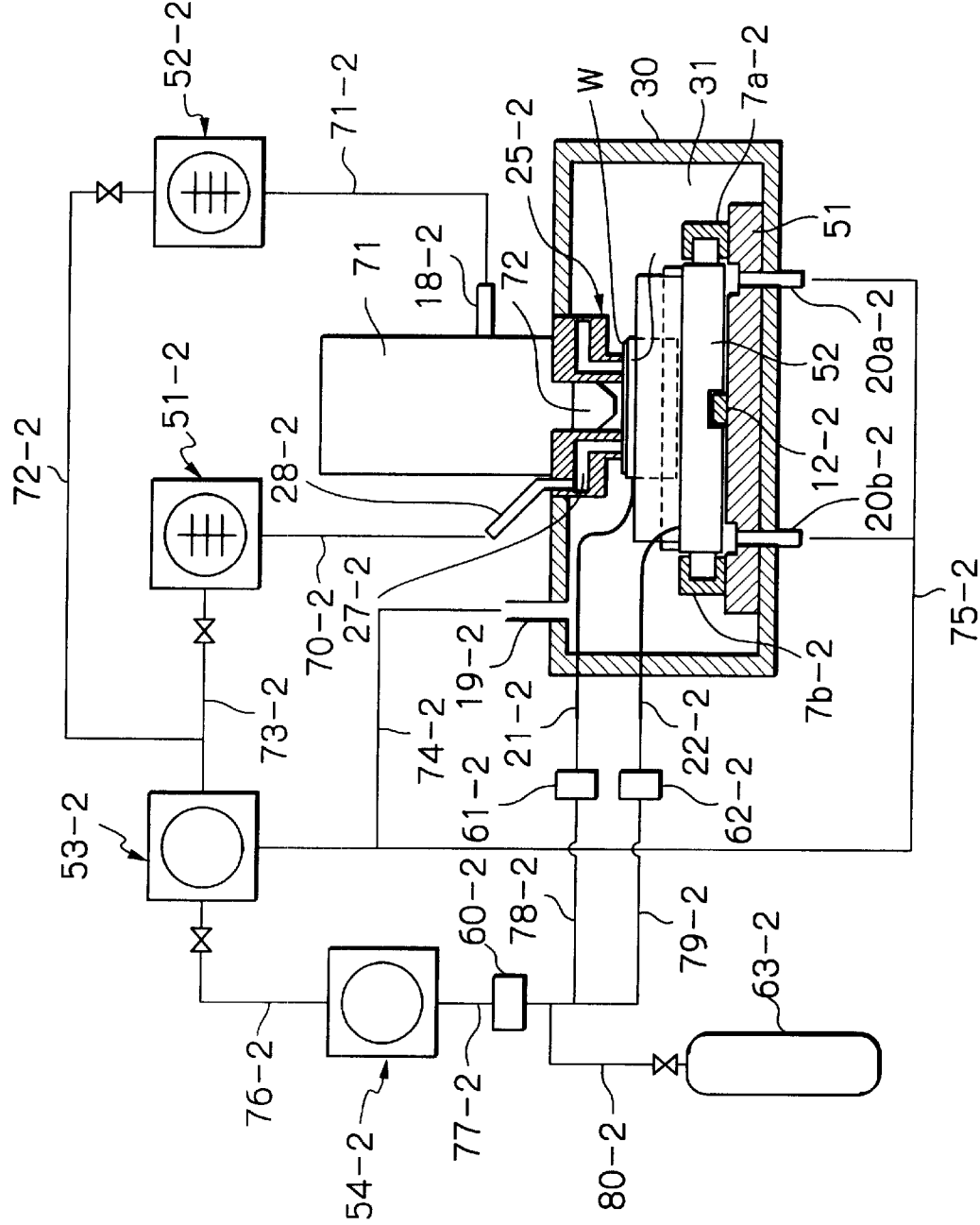
FIG. 23 illustrates a gas circulation piping mechanism installed in the embodiment indicated in FIG. 21.

FIG. 23 illustrates a piping system for the apparatus illustrated in FIG. 22. The working chamber 31 defined is connected to a dry vacuum pump 53-2 through vacuum pipes 74-2, 75-2. Also, the annular grove 27-2 of the differential pumping mechanism 25-2 is connected to a turbo molecular pump 51-2, which is an ultra-high vacuum pump, through a vacuum pipe 70-2 connected to an evacuate port 28-2. Further, the inside of the column 71 is connected to a turbo molecular pump 52-2 through a vacuum pipe 71-2 connected to the evacuate port 18-2. These turbo molecular pumps 51-2, 52-2 are connected to the dry vacuum pump 53-2 through vacuum pipes 72-2, 73-2. (While in FIG. 23, a single dry vacuum pump is in double use for a roughing pump as the turbo molecular pump and a vacuum evacuation pump for the vacuum chamber, it is contemplated that separate dry vacuum pumps may be used for evacuation depending on the flow rate of the high pressure gas supplied to the hydrostatic bearings of the X-Y stage, the volume and inner surface area of the vacuum chamber, and the inner diameter and length of the vacuum pipe.)

The hydrostatic bearing of the X-Y stage are supplied with highly pure inert gas ($N_2$ gas, Ar gas or the like) through the flexible pipes 21-2, 22-2. The gas molecules blown out from the hydrostatic bearings diffuse in the working chamber, and are exhausted by the dry vacuum pump 53-2 through the evacuate ports 19-2, 20a-2, 20b-2. Also, the gas molecules introducing into the differential pumping mechanism and the electron beam irradiation space are sucked from the annular groove 27-2 or the bottom of the column 71, evacuated by the turbo molecular pumps 51-2 and 52-2 through the evacuate ports 28-2 and 18-2, and evacuated by the dry vacuum pump 53-2 after they have been pumpinged by the turbo molecular pump. In this way, the highly pure inert gas supplied to the hydrostatic bearings is collected and evacuated by the dry vacuum pump.

On the other hand, the dry vacuum pump 53-2 has an evacuate port connected to a compressor 54-2 through a pipe 76-2, while the compressor 54-2 has an evacuate port connected to the flexible pipes 21-2, 22-2 through pipes 77-2, 78-2, 79-2 and regulators 61-2, 62-2. Therefore, the highly pure inert gas exhausted from the dry vacuum pipe 53-2 is again pressurized by the compressor 54-2, regulated to a proper pressure by the regulators 61-2, 62-2, and again supplied to the hydrostatic bearings of the X-Y table.

As described above, the gas supplied to the hydrostatic bearings must be purified as high as possible to maximally exclude moisture and oil components, so that the turbo molecular pumps, dry pump and compressor are required to have structures which prevent moisture and oil components from introducing into gas flow paths. It is also effective to provide a cold trap, a filter or the like (60-2) in the middle of the discharge side pipe 77-2 of the compressor to trap impurities such as moisture and oil components mixed in a circulating gas such that they are not supplied to the hydrostatic bearings.

In this way, since the highly pure inert gas can be an circulated for reuse, the highly pure inert gas can be saved. In addition, since the inert gas is not supplied in an uncontrolled manner into a chamber in which the apparatus is installed, the possibility of accidents such as suffocation by the inert gas can be eliminated.

The circulating pipe system is connected to a highly pure inert gas supply system 63-2 which serves to fill the highly pure inert gas into the entire circulating system including the working chamber 31, vacuum pipes 70-2–75-2, and pressurizing pipes 1676–1680, and to supply the shortage if the flow rate of the circulating gas is reduced by some cause.

It is also possible to use a single pump as the dry vacuum pump 53-2 and the compressor 54-2 by providing the dry vacuum pump 53-2 with a function of compressing to the atmospheric pressure or higher. Further, the ultra-high vacuum pump for use in evacuating the column 72 may be implemented by a pump such as an ion pump, a getter pump instead of the turbo molecular pump. However, when such an entrapment vacuum pump is used, a circulating piping system cannot be built in this portion. Also, a dry pump of another configuration such as a diaphragm dry pump may of course be used instead of the dry vacuum pump.

In the constitutions of the electron beam emitting tip and the pumping mechanisms for the space around the emitting tip as described above, the stage apparatus can be accurately positioned in the vacuum working chamber. Further, it is possible to create high quality image data because the pressure around the emitting tip is hardly increased. These constitutions are applicable to embodiments of the electron beam apparatus which will be explained below, as well as the apparatus shown in FIG. 8.

Figure 24:
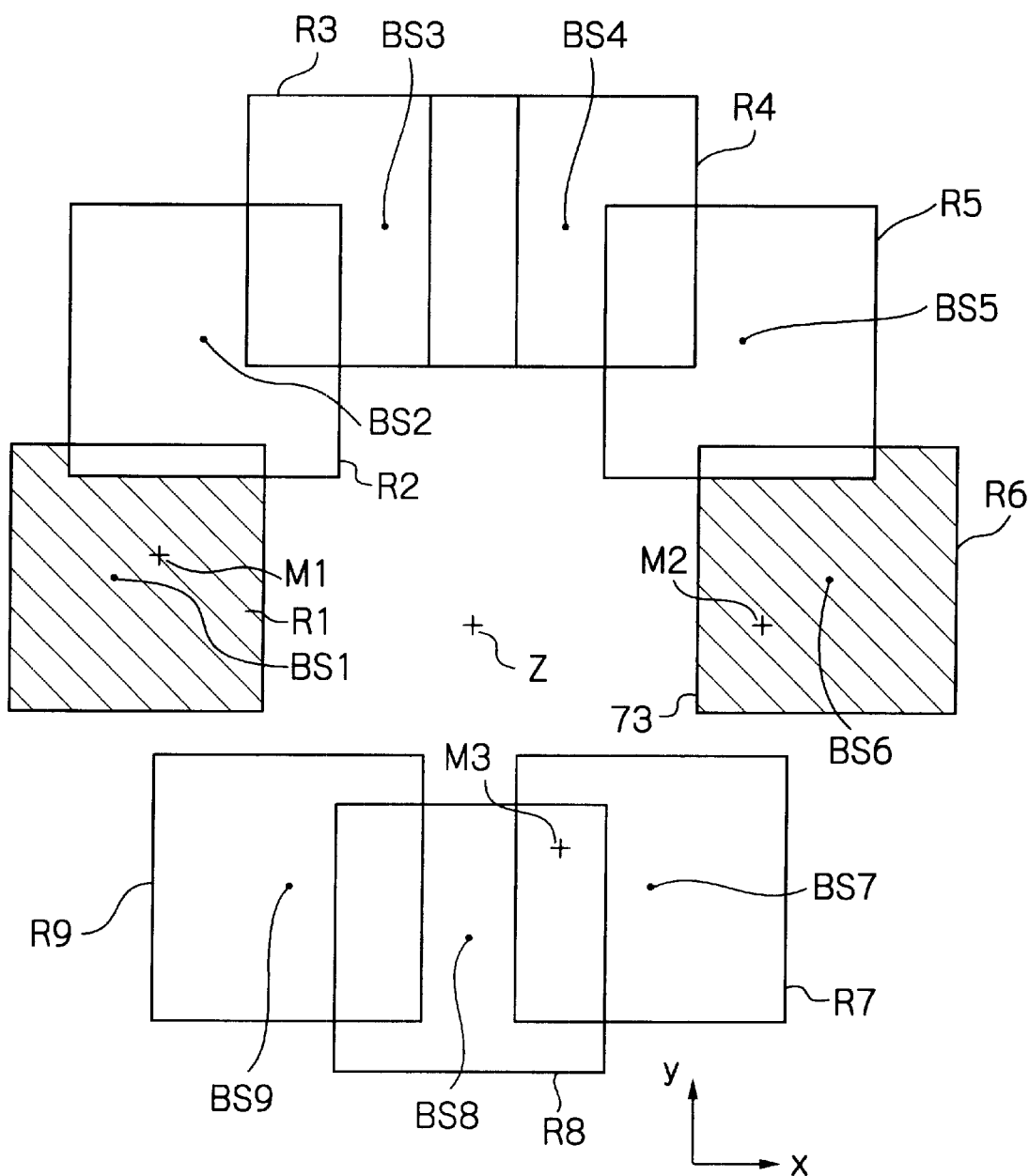
FIG. 24 illustrates a relationship between alignment marks and scanning arias of multi-beams on a wafer.

Next, referring to FIG. 24, the electron beam apparatus according to the present invention will be described for alignment of an electron optical system 70 to a wafer W at the start of testing. Generally, a wafer is formed with one or a plurality of alignment marks, and a primary electron beam is scanned at the start of testing to detect the alignment marks to align the wafer to the electron beam apparatus. FIG. 24 schematically illustrates the relationship between alignment marks and scanning regions by primary electron beams when the wafer is aligned. In FIG. 24, M1–M3 designate alignment marks on the wafer W; BS1–BS9 beam spots formed on the surface of the wafer by nine primary electron beams; R1–R9 regions scanned by these primary electron beams at the start of testing; and Z the optical axis of a primary optical system of the electron beam apparatus.

In FIG. 24, when any of the alignment marks M1–M3 is not included in the vicinity of the optical axis Z, i.e., in any of the regions R1–R9, the positions of the alignment marks cannot be detected. Also, when one alignment mark exists in both of two regions R7 and R8, as the alignment mark M3, the one alignment mark will be detected twice, possibly resulting in an erroneous mark detection.

On the other hand, when one alignment mark exists in one region, such as the alignment marks M1 and M2, a correct mark detection can be accomplished. In other words, only when a single primary electron beam is scanning one alignment mark, a signal detected thereby is utilized as an alignment signal. Also, in the illustrated example, the electron beams which scan the regions R1 and R6 are spaced furthest away from each other and include few overlapped region, so that an XY stage is preferably moved so as to utilize one of these electron beams for detecting the marks. By setting in this manner, even when the widest region is scanned upon alignment, it is possible to satisfy the same condition as the case where the alignment marks are scanned only with a single electron beam.

The foregoing alignment is applicable to other embodiments, later described, and modifications thereto, other than the electron beam apparatus of the embodiment illustrated in FIG. 8.

Next, description will be made on a method of improving the S/N ratio, which can be employed in the electron beam apparatus of the present invention. Assume in the following description that the beam diameter D of an electron beam refers to the dimension of the diameter of an image on the surface of a wafer formed by the electron beam (diameter or diagonal length), and the spacing between electron beams refers to the center-to-center distance between adjacent images on the surface of the wafer formed by adjacent electron beams. A modulation transfer function (MTF) is one of performance evaluation method for optical systems, also called a sinusoidal response function or a contrast transfer function, and refers to the ratio of image contrast to object contrast, when passing through an optical system. When defects are to be detected in patterns by the electron beam apparatus, a minimum line width corresponds to a minimum dimension of defects to be detected.

Conventionally, a beam diameter D sufficiently smaller than 0.1 $\mu m \phi$ has been empirically used for detecting a minimum line width d of 0.1 $\mu m$, and a beam having a beam diameter D sufficiently smaller than 0.05 $\mu m \phi$ has been used for evaluating patterns having a minimum line width d of 0.05 $\mu m$, without clarifying an optimal value for the ratio of the beam diameter D of an electron beam for testing to the minimum line width d of patterns to be detected.

However, when the beam diameter D of an electron beam is too small for the minimum line width d of patterns to be evaluated, a problem arises in that the S/N ratio (signal/noise ratio) is reduced due to a small beam current I and a small number of secondary electron beams per pixel, though the resolution is increased, thereby failing to improve the throughput for the evaluation, i.e., the amount of processing per unit time. Conversely, when the beam diameter D is too large, a problem arises in that a pattern image is blurred, i.e., MTF is too small, and the contrast of the pattern is too low, thereby failing to conduct a highly accurate test, and a problem arises in that the accuracy and throughput for the evaluation cannot be improved due to a low S/N ratio.

The inventors clarified the relationship between the FIE ratio D/d of the beam diameter D of an electron beam to a minimum line width (or defect size) d of a pattern to be evaluated and the S/N ratio, and enabled line width detection, defect detection, and the like with a high accuracy and high throughput by calculating D/d which can maximizes the S/N ratio, and D/d which can provide a high S/N ratio. In the following, setting of a beam diameter will be described in detail.

Figure 25:
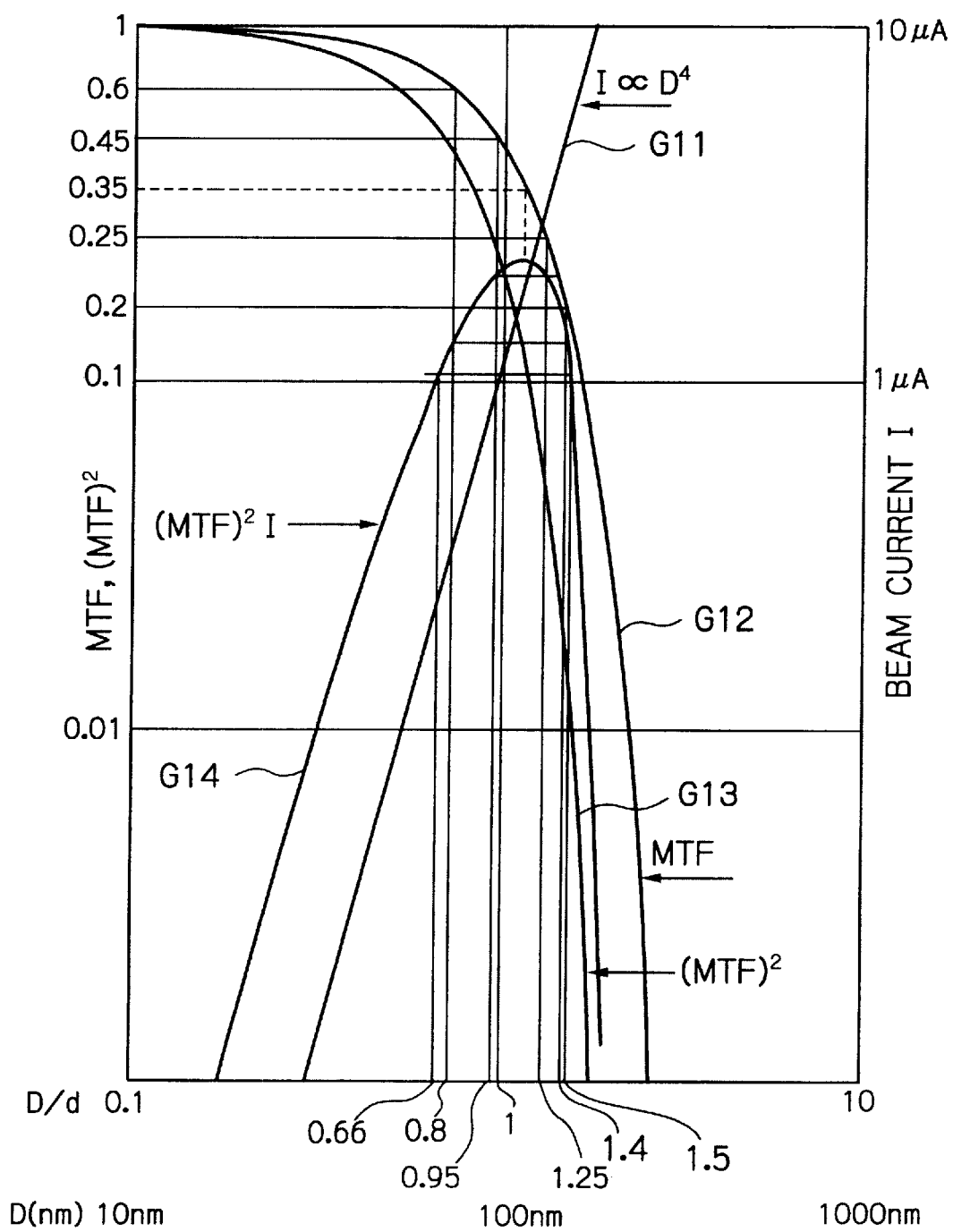
FIG. 25 shows a graph illustrating relationships between a beam current I, MTF, $MTF^2$, $MTF^2I$, and a ratio D/d where D is a beam diameter and d is a minimum line width.

FIG. 25 is a graph for use in calculating the value of beam diameter D/minimum line width d which provides the S/N ratio at a maximum value or near the maximum value, resulting from a simulation performed by the inventors. In FIG. 25, a graph G11 represents the relationship between the beam diameter D and a beam current (I D$^4$); a graph G12 represents the relationship between D/d and MTF; a graph G13 represents the relationship between D/d and (MTF)$^2$; and a graph G14 represents the relationship between D/d and (MTF)$^2$I. These graphs G11–G14 were produced in the following manner.

First, the S/N ratio of a signal generated when the surface of a wafer was scanned by a narrowed primary electron beam to detect secondary electrons generated from the wafer can be expressed by the following equation:

$$S/N = \{\text{Signal}/(\text{Offset Value} + \text{Signal})\}(\text{MTF})(N^*/2)^{1/2} \quad (1)$$

where MTF represents a reduction in contrast of a signal generated when scanning in a direction in which a one-dimensional pattern having a finite dimension is traversed by a beam of a finite dimension, and is a function of beam diameter/minimum line width=D/d. N* represents the number of secondary electrons detected per scanned pixel, and is proportional to the product of the beam current I and secondary electron transmittance. Stated another way:

$N^*$ (Beam Current $I$)(Secondary Electron Transmittance)  (2)

For maximizing the S/N ratio, $(S/N)^2$ may be maximized, so that equation (3) is derived from equation (1) and equation (2):

$(S/N)2 \ (MTF)^2 I$  (3)

MTF was calculated from the following equation:

$MTF$=Max (convolutional function of $f_1, f_2$)  (4)

$f_1$=1 when $NP/2x<(N+1)P/2$ $f_1=(N+1)$ when $P/2x<(NP/2)$  (5)

$f_2=1/\sigma(2\pi)\exp\{-x_2/2\sigma_2\}$  (6)

where N: Integer Number:

$P=2.34\sigma(D/d)$

σ: a constant of a Gaussian function, and variance.

For example, when the ratio D/d on the horizontal axis in the graph of FIG. 25 is 1.0, the value of MTF at this time is derived by determining the function $f_1$ with P=2.34σ, deriving a convolutional function with the function $f_2$, and calculating the amplitude of the resulting function (a maximum value because a minimum value is zero), thus deriving the value of MTF for 1.0 on the horizontal axis in FIG. 25.

In a similar manner, the value of MTF is derived by substituting 0.5, 1.5, 2.0, . . . , and the like into the ratio D/d, and the resulting values are plotted to derive the graph G12 which represents the relationship between MTF and D/d.

$(MTF)^2$ is found from the graph G12 to create the graph G13, and the product of the graph G11 representing I and the graph G13 representing $(MTF)^2$ is calculated as $(MTF)^2 I$ to derive the graph G14 which represents the right side of equation (3).

As is apparent from FIG. 25, the graph G14 shows that $(MTF)^2 I$ takes a maximum value with D/d1.1, at which $(S/N)^2$, i.e., the S/N ratio is maximized. MTF at this time is approximately 0.35. The graph G14 in turn shows that $(MTF)^2 I$ (i.e., the S/N ratio) presents a value near the maximum value with D/d in a range of 0.8 to 1.4. MTF at this time is in a range of 0.2 to 0.6. Further, according to the graph G4, the S/N ratio becomes higher when D/d lies in a range of 0.95 to 1.25. MTF at this time is in a range of 0.25 to 0.45.

Thus, the maximum S/N ratio can be achieved by approximating D/d extremely close to 1.1; a S/N ratio close to the maximum value can be achieved by selecting D/d in the range of 0.95 to 1.25; and a relatively high S/N ratio can be achieved by selecting D/d in a range of 0.8 to 1.4. Therefore, the value of D/d may be set depending on which degree of S/N ratio is required. For example, the D/d ratio may be positioned in a range of 0.66 to 1.5.

Converting the foregoing in a range of MTF, the maximum S/N ratio can be achieved when MTF is 0.35; a S/N ratio substantially close to the maximum value can be achieved when MTF is in a range of 0.25 to 0.45; and a relatively high S/N ratio can be achieved when MTF is in a range of 0.2 to 0.6. Depending on a tolerance for the S/N ratio, MTF may be set in a range of 0.35 to 0.86.

In some cases, it may be necessary to execute two or more detection modes using a single electron beam apparatus, such as the case where there are two requirements: when a testing time is desirably T with the minimum line width d1 of a pattern to be evaluated, and when a testing time is desirably reduced to T/4, for example, with the minimum line width d2 increased by a factor of two (d2=2d1). With two or more detection modes required, when a time for changing the beam diameter D can be sufficiently reduced, beam diameters D1, D2 used for the respective minimum line widths d1, d2 may be changed to simultaneously satisfy the following two conditions:

$0.B1/d1 \ 1.4$ $0.B2/d2 \ 1.4$ whereby the most suitable electron beams can be used for the respective minimum line widths. In this event, the beam diameter can be changed by providing two or more stages of lenses and varying only a reduction ratio without changing the focal plane, making use of a zoom action. In this event, in the electro-optical system 70 of the electron beam apparatus illustrated in FIG. 8, the position of a reduced image of an aperture 723a of a multiple-aperture plate 723 in a primary optical system is displaced in the Z-axis (optical axis) direction to change the reduction ratio related to the aperture 723a to a wafer W, and the beam diameter D is changed such that the value of D/d falls within a range of 0.8 to 1.4, by way of example. In this manner, the S/N ratio can be brought to a value substantially close to the maximum value.

The foregoing setting of the beam diameter D for improving the S/N ratio is applicable to other embodiments, later described, and modifications thereto, other than the electron beam apparatus of the embodiment illustrated in FIG. 8.

Next, description will be made on a method of detecting short-circuiting in a wiring pattern on a wafer W using the electron beam apparatus illustrated in FIG. 8. As described above, for testing a wafer for defects on the surface thereof and evaluating patterns formed on the surface of a sample, the wafer is set on the stage apparatus 50, and the amount of emitted secondary electrons, which varies in response to a potential applied by injected charges resulting from irradiation of the surface of the wafer with a plurality of electron beams, is observed by a plurality of detectors 761. Therefore, for injecting charges by scanning, for example, an LSI with an electron beam, a short-circuited wire portion in the LSI exhibits an initial potential value different from that of a normal wire portion, so that the short-circuited wire portion can be detected by making use of this phenomenon.

When an axially symmetric electrode 730 is applied with a voltage lower than that to the wafer W, the axially symmetric electrode 730 forms a constant potential barrier. Secondary electrons pass over the potential barrier or are blocked by the potential barrier depending on the potential possessed by a pattern on the wafer W. Therefore, secondary electrons which pass over the constant potential barrier are only detected by the respective detectors 761 corresponding thereto, so that the amount of detected secondary electrons increases or decreases depending on the potential possessed by the pattern. On the other hand, the pattern on the wafer is injected with charges by the irradiation of electron beam, generating a potential which is determined depending on the electrostatic capacitances possessed by these charges. Therefore, it can be assumed, for example, that even different chips have the same electrostatic capacitances if they have the same pattern, and they have the same potential if they are injected with the same amount of charges. The secondary electrons are observed based on such logic, and determination can be made that short-circuiting exists in a pattern if a potential lower than an expected value is detected for a pattern which is expected to have the same potential.

The foregoing detection of short-circuiting is also applicable to other embodiments, later described, and modifications thereto, other than the electron beam apparatus of the embodiment illustrated in FIG. 8.

Next, description will be made on a method of reducing the influence caused by charge-up executed in the electron beam apparatus according to the present invention. Conventionally, in electron beam apparatuses of the type which irradiates a wafer with multi-beams, i.e., a plurality of primary electron beams, a variety of technical issues remain unsolved, and one of the issues is the problem of charge-up which occurs on the surface of a wafer. The charge-up, i.e., charging refers to a phenomenon found on an object under observation, i.e., a sample on which an insulating material, a stray conductive material and the like exist, on which an irradiated portion is positively or negatively charged if the number of incident electron beams is not identical to the number of electrons emitted as secondary electrons or reflection electrons. The charge-up is a phenomenon inevitable in a semiconductor wafer on which an insulating material, a stray conductive material and the like exist. The occurrence of charge-up would result in failure in maintaining the surface of the wafer in an equi-potential state as well as a phenomenon in which potentials largely differ within a field of view due to local charging.

On the other hand, when low energy electrons such as secondary electrons are accelerated to make an enlarged projection at a high magnification using an electrostatic lens, a multi-beam has a narrow energy width, which can be condensed, due to axial chromatic aberration, and is sensitive to the uniformity of energy over the entire field of view. Therefore, if a potential distribution largely differs on the surface of a wafer, an image may be distorted or fails to focus in the vicinity of different potentials, resulting in a problem that a correct observation is prevented. In addition, if a wafer is overcharged, the sample itself could be damaged due to resulting discharge or breakdown.

The occurrence of charge-up is determined by the secondary electron yield. The secondary electron yield refers to the value calculated by dividing the number of generated secondary electrons and reflection electrons by the number of electrons irradiated to a wafer. When the secondary electron yield is larger than one, the wafer is positively charged. When the secondary electron yield is smaller than one, the wafer is negatively charged. It will therefore be understood that the problem as mentioned above could be reduced if primary electron beams were irradiated to bring the secondary electron yield as close as possible to one for an insulating material and a stray conductive material, however, the matter is not so simple in practice.

As a result, since a plurality of types of insulating materials and stray conductive materials having different secondary electron generation efficiencies mixedly exist on a semiconductor wafer in many cases, it is extremely difficult to capture an image without charging up these materials. In addition, there are images, such as a potential contrast image, which cannot be observed unless the charge-up is intentionally produced to some degree, in which case it is difficult to control the degree of charge-up.

Figure 26:
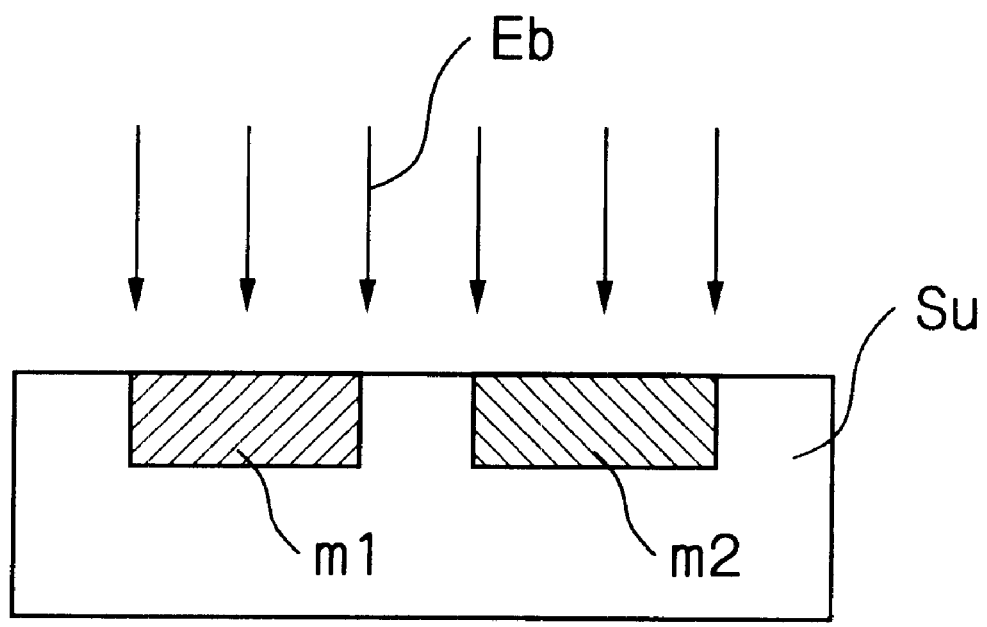
FIG. 26 shows a cross-sectional view explanatorily illustrating a wafer which is a sample.

For example, as a practical example of a semiconductor wafer including an insulating material, consider one which has a cross-sectional structure as illustrated in FIG. 26. In FIG. 26, Su denotes a silicon substrate which is a semiconductor; and m1, m2 are insulating materials of different kinds. Since the surface of the semiconductor wafer has been planarized in a process such as CMP, a normal edge-enhanced SEM observation, not to mention an optical microscopic observation, cannot provide a satisfactory observation image with low image contrast.

Figure 27A:
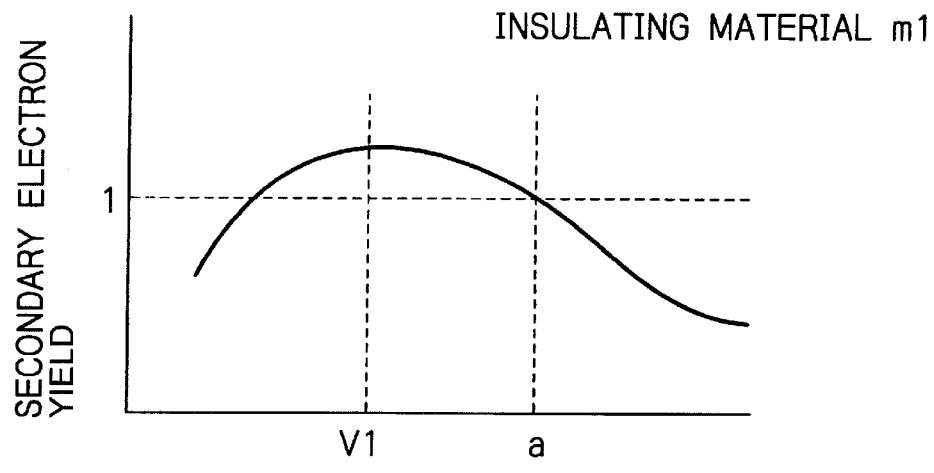
FIGS. 27A and 27B show graphs illustrating relationships between landing energy of an electron and secondary electron yield.

When this wafer is irradiated with an electron Eb having landing energy (incident energy) V1, charge-up occurs, causing the landing energy to shift. The amount of shift reaches points a, b in graphs of FIGS. 27A and b which represent the secondary electron generation efficiencies of the insulating materials m1 and m2, and enters an equilibrium state, as long as there is no leak current. As a result, charge-up potentials increase by $U_{S/A}$ (=a−V1) and $U_{S/B}$ (=b−V1), respectively.

In this event, the following two inequities may be simultaneously satisfied:

$$U_{min} < U_{S/A} < U_{max} \quad (7)$$

$$U_{min} < U_{S/B} < U_{max} \quad (8)$$

Figure 27B:
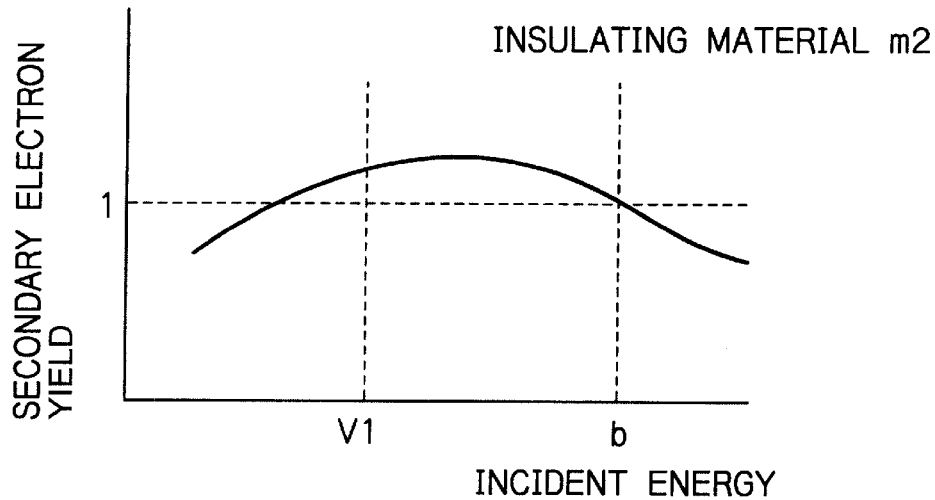

However, the simultaneous satisfaction of the two inequities cannot often be achieved even if the position of the landing energy V1 is changed in the graph of FIG. 27.

Figure 28:
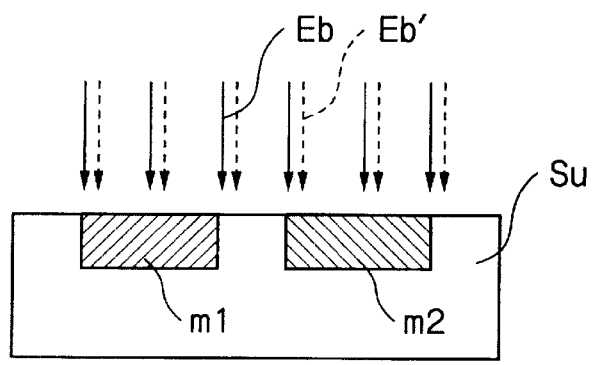
FIG. 28 shows a view for explaining adjustment of an electron beam for a wafer adjustment, according to the present invention.
Figure 29A:
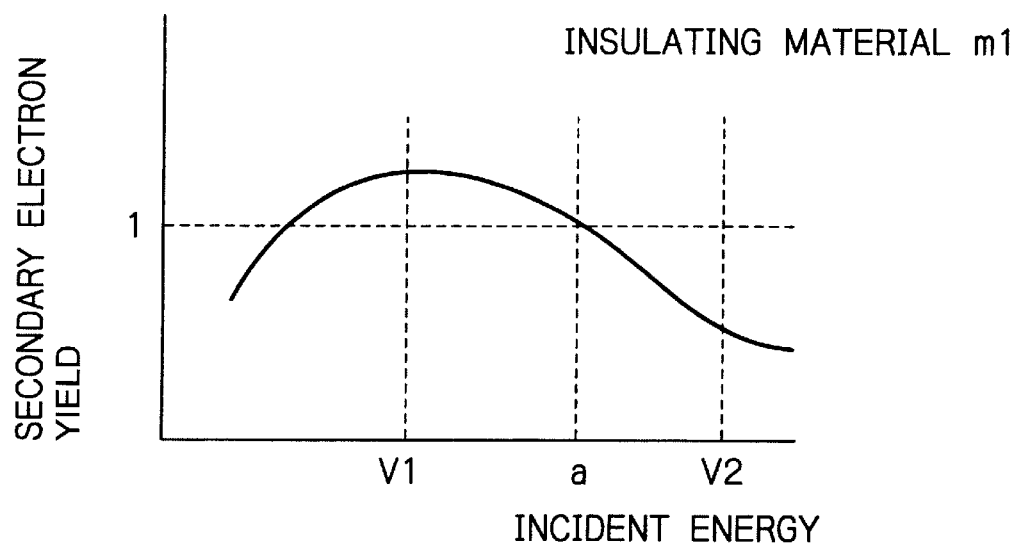
FIGS. 29A and 29B are graphs illustrating relationships between landing energy for two isolators and secondary electron generation efficiencies.
Figure 29B:
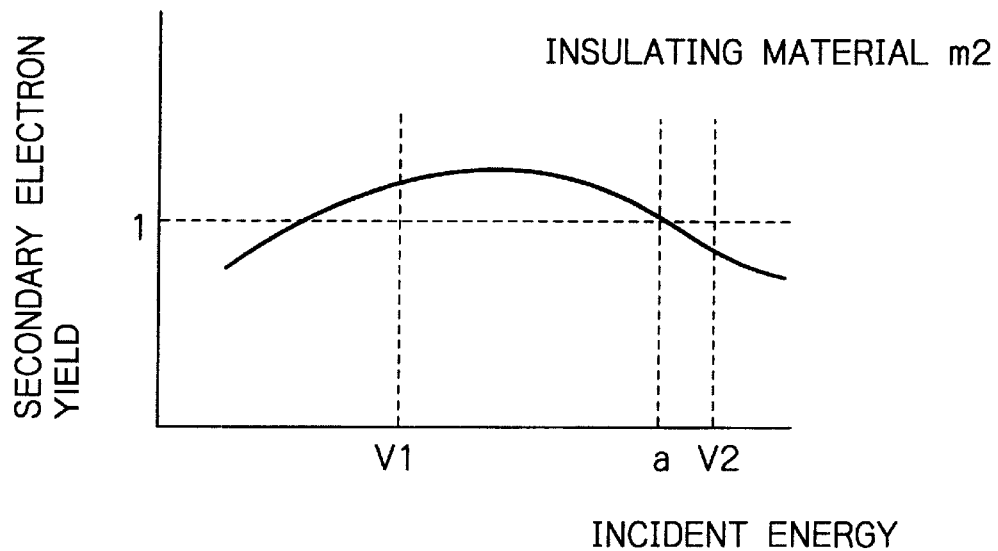

Thus, in the electron beam apparatus 70 according to the present invention, an electron Eb' having landing energy V2 is also irradiated in addition to the electron having landing energy V1, as illustrated in FIG. 28. Here, the landing energy V1 and V2 are set at positions on both sides of equilibrium points a and b of the insulating materials m1 and m2, as shown in FIG. 29.

Charge-up potentials of the respective insulating materials m1 and m2, irradiated with the two electrons having different energy, are detected in the following manner. Secondary electron efficiency curves of the insulating materials m1 and m2 for the energy V of irradiated electrons are represented by FA(V) and FB(V), respectively. Also, electron irradiation densities of the landing energy V1 and V2 on the wafer are represented by I1 and I2, respectively. The densities Q1 and Q2 of secondary electron amounts emitted from the surfaces of the insulating materials m1 and m2, caused by the irradiation of the energy, can be expressed as follows:

$$Q1 = I1 \cdot FA(V1) + I2 \cdot FA(V2)$$

$$Q2 = I1 \cdot FB(V1) + I2 \cdot FB(V2)$$

Generally, the values of Q1 and G2 are not identical to the electron irradiation densities I1 and I2. As a result, charge-up occurs, and the equilibrium states are reached after the surface potential changes only by $U_{S/A}$ and $U_{S/B}$ on the respective insulating materials. The equilibrium states can be expressed in the following manner:

$$I1+I2 = I1^*FA(V1+U_{S/A}) + I2^*FA(V2+U_{S/A}) \quad (9)$$

$$I1+I2 = I1^*FB(V1+U_{S/B}) + I2^*FB(V2+U_{S/B}) \quad (10)$$

These two equations (9) and (10) can be re-written in the following manner through transformation with substitution of I1/(I9+I2)=α:

$$I = \alpha^*FA(V1+U_{S/A}) + (1-\alpha)^*FA(V2+U_{S/A}) \quad (11)$$

$$I = \alpha^*FB(V1+U_{S/B}) + (1-\alpha)^*FB(V2+U_{S/B}) \quad (12)$$

$U_{S/A}$ and $U_{S/B}$ are determined to be particular values which satisfy inequities (7) and (8), and one of the ratios α of I1 to V1, V2 and total current irradiation density is used as a defined value, and the remaining two are calculated such that equations (11) and (12) are simultaneously satisfied, so that the wafer including the insulating materials can be observed in a good focused state. Then, on top of that, illumination can be made in the most preferable irradiation condition by adjusting the total current irradiation density.

Alternatively, when all of the ratio α for V1, V2 and total current irradiation density in equations (11), (12) are found as variables, insulating materials of up to three kinds can be supported. Further, since two new variables V and I are increased as one type of irradiation electron energy is increased, insulating materials which can be supported are increased two by two.

As described above, since the wafer can be simultaneously irradiated with a plurality of electron beams, and the current amount and incident energy from each electron source can be controlled independently, the current amount and incident energy can be set such that a change in surface potential due to charge-up of each insulating material or a stray conductive material reaches a target value. It is therefore possible to control a change ($U_S$) in surface potential due to charge-up of each insulating material or a stray conductive material to lie between a minimum amount ($U_{min}$) required for observing an image and a maximum value ($U_{max}$) with which a less distorted observation image can be produced without damaging the wafer itself, so that a clear image can be produced without distortion. Preferably, the field of view is illuminated in a uniform irradiation condition, resulting in a more clear image without light and dark image regions caused by partial charge-up and uneven irradiation within the field of view.

The foregoing method of controlling a change in the surface potential due to charge-up to a target value is applicable to other embodiments, later described, and modifications thereto, other than the electron beam apparatus of the embodiment illustrated in FIG. 8.

Preferably, the amount of current from at least one electron gun and the incident energy on the wafer are made controllable in a time division manner, thereby producing an effect that the amount of current and the incident energy appear as if a plurality of different electron guns are provided. Since temporal and spatial overlapping can be established in the charge-up, such a configuration can also reduce the problem of charge-up.

In this event, the detector which receives secondary electrons and transduces them into an electric signal may employ a combination of secondary electrons–optical transducer and an opto-electric transducer such as PTM, and charges for one period of illumination switched and irradiated in a time division manner are once stored in a CCD and extracted, whereby outputs for all different illuminating light can be output in combination. Even in this case, the field of view is preferably illuminated in a uniform illuminating condition.

Figure 30:
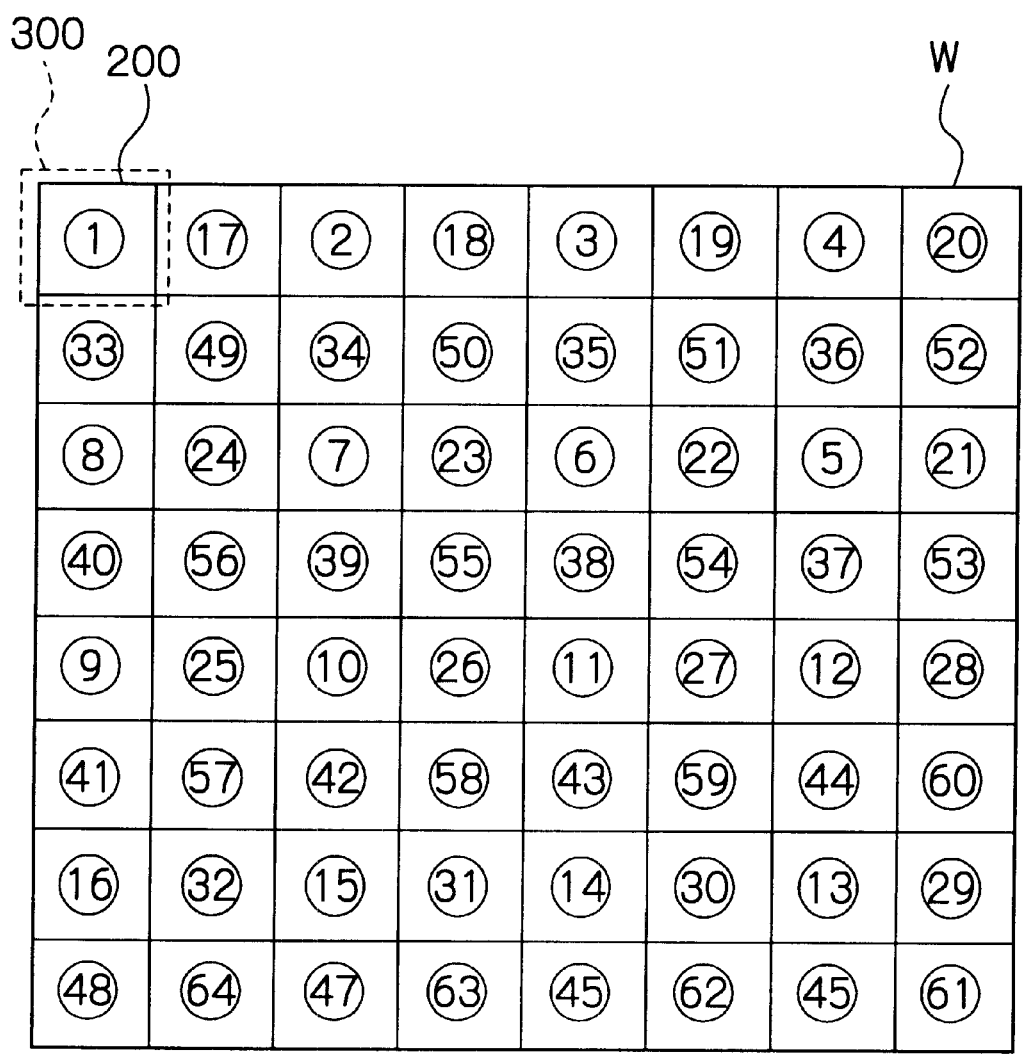
FIG. 30 is a drawing for explaining an example of a method of beam scanning on a wafer according to the present invention.
Figure 31:
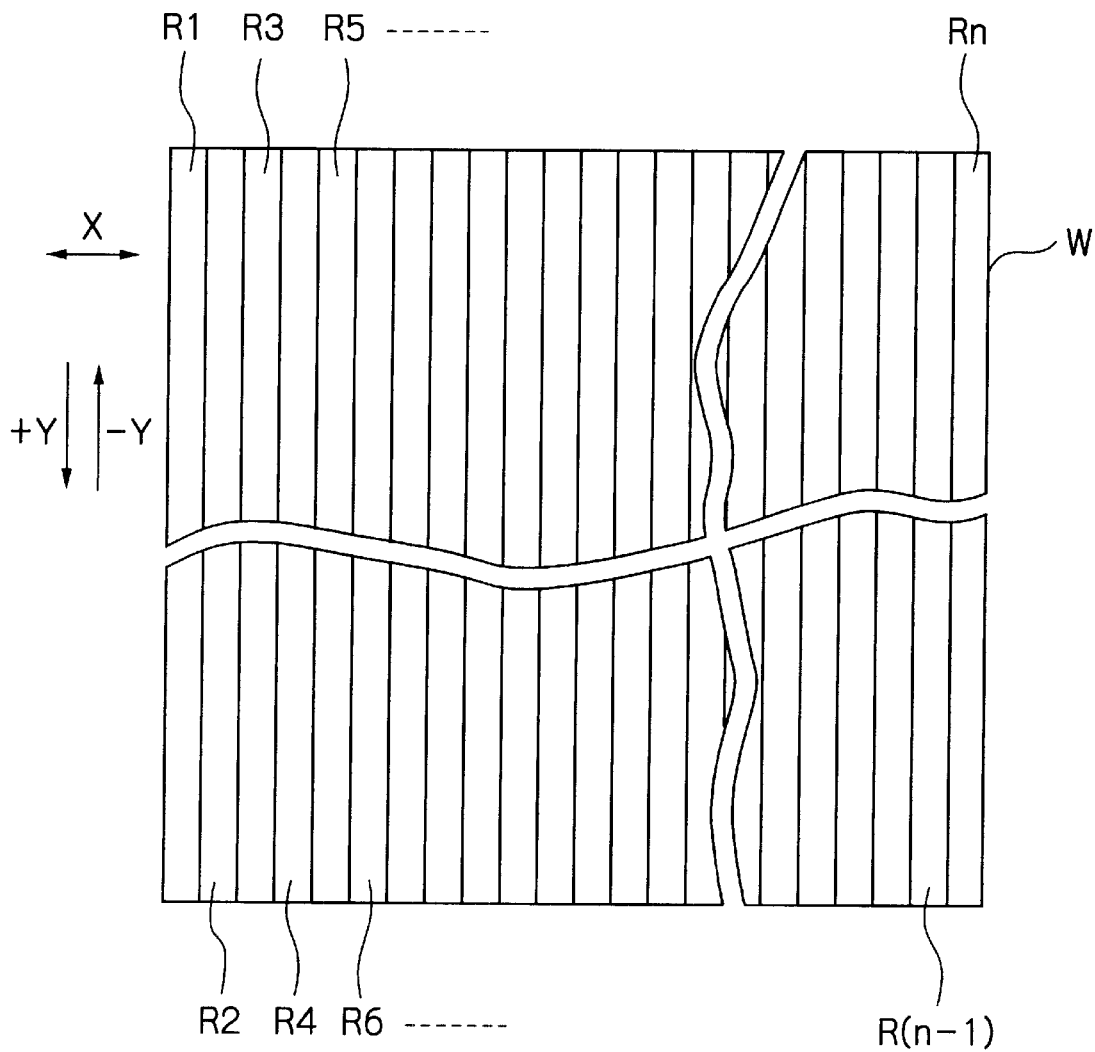
FIG. 31 is a drawing for explaining another example of a method of beam scanning on a wafer according to the present invention.
Figure 32:
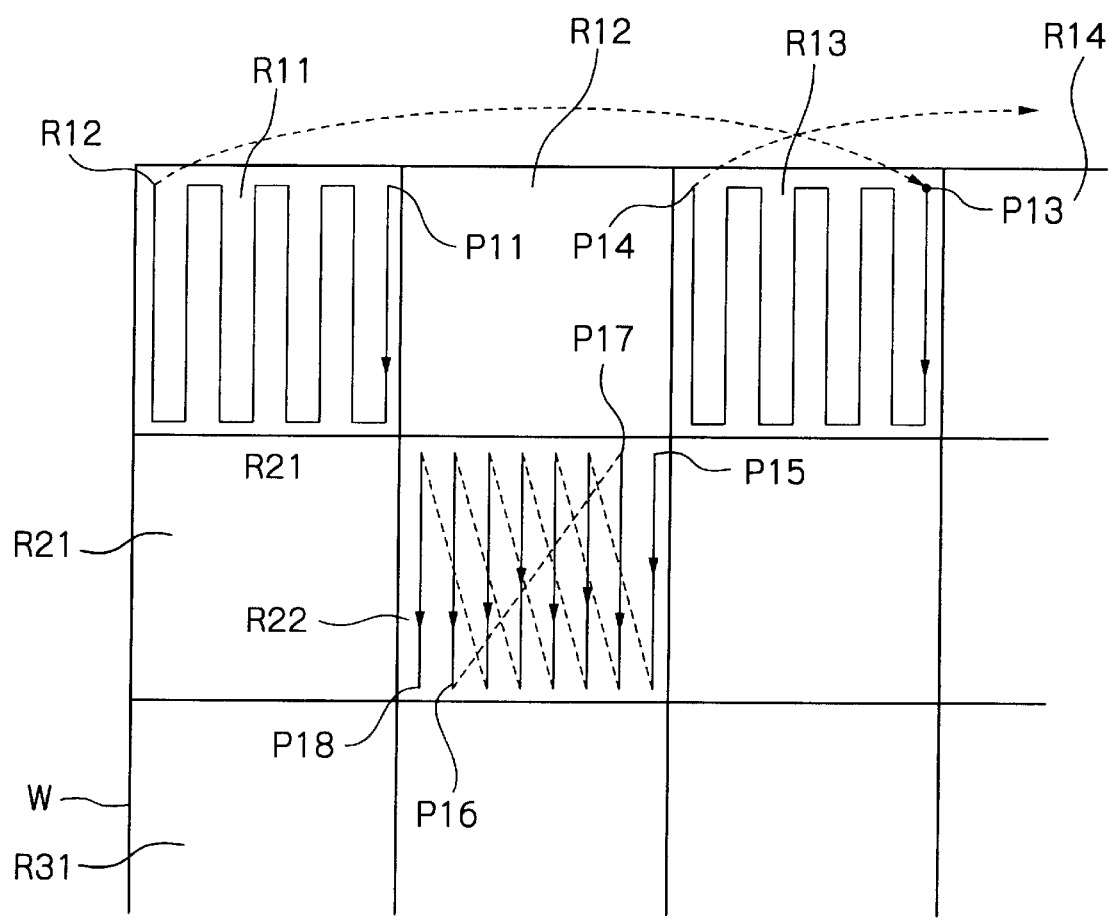
FIG. 32 is a drawing for explaining more further example of a method of beam scanning on a wafer according to the present invention.

Referring next to FIGS. 30 through 32, description will be made on a method of scanning a wafer W using the electron beam apparatus illustrated in FIG. 8.

In one scanning method, as illustrated in FIG. 30, the wafer W is scanned by a primary electron beam in units of small divided regions 200. In the electron beam apparatus, the small region 200 is set such that the field of view of the primary electron beam is chosen to be a slightly larger region 300 than the small region 200. The small region 200 corresponds to a region to which the primary electron beam can be electrically deflected. After detecting secondary electrons emitted from the wafer, the wafer is moved to irradiate the next small region 200, wherein the next region is an unirradiated small region, skipping at least one or more of adjacent small regions. Since charges decrease over time, the skipped small regions are irradiated after the lapse of time at which the influence of charged small region, after irradiation, has been sufficiently reduced. As an exemplary method of selecting an irradiation order, as 64 small divided regions are irradiated in the order of (1), (2), (3), . . . as illustrated in FIG. 30, a sufficient time can be taken after irradiation of a small region until irradiation of a small region adjacent to that small region. Preferably, while the wafer W is being moved, a test is conducted based on secondary electron beams detected from the irradiated small region.

The selection of the irradiating order for such small regions is applicable to an electron beam apparatus which uses a single primary electron beam.

FIG. 31 illustrates another scanning method, wherein a wafer W is divided into small regions R1, R2, R3, . . . in stripes. Then, as the primary electron beam is scanned in the minor axis direction (X-axis direction) of the small regions, the wafer is moved in the major axis direction (Y-axis direction) of the small regions. When one small region is skipped, the wafer is moved in the +Y-axis direction, while scanning, and the small region R1 is irradiated. Then, after the wafer is moved in the X-axis direction, the small region R3 is irradiated while the wafer is moved in the -Y-axis direction. Sequentially, every other small regions are irradiated, such that after irradiating a small region Ri, a small region R(i+1) (i=1, 2, . . . n−1) is irradiated.

FIG. 32 illustrates a further scanning method. In this method, for irradiating a small region by scanning, the scanning is started from the side near a small region to be scanned, and proceeds to the far side. Specifically, when the scanning is advanced for each column, a small region R11 is scanned, then a small region R12 is skipped, and a small region R13 is scanned, in which case the scanning of a small region R1 is started from a point P11 near the small region R13 and terminated at the furthest point P12. As the small region R11 has been scanned, the wafer W is moved in steps, and the scanning of the small region R13 is started from a point P13, and performed up to a point P14. Subsequently, R14 adjacent to the small region R13 is skipped, and a small region R15 is scanned. As the scanning of this row is terminated, the scanning proceeds to the next row, and each small region is scanned in a similar manner. According to such a scanning method, the influence by charging can be reduced. Alternatively, after a small region Rij has been scanned, an adjacent small region Ri(j+1) may be scanned without skipping this small region Ri(j+1) on the assumption that the scanning is started from a point in a small region far away from a scanning end point of the small region ij which has been scanned immediately before.

Also, in the scanning of each small region in FIG. 32, for example, as shown in a small region R22, the scanning may be started from a point P15, returns to a point P17 at the time a point P16 is reached, and then proceeds to a point P18. A broken line in the small region R22 indicates a fly-back line. By thus raster scanning every other small regions, the influence by the preceding scanning can be reduced. The number of skipped lines may be an arbitrary plurality of lines, instead of one.

In the scanning methods illustrated in FIGS. 30 through 32, the skipping of small regions can be electrically controlled, so that this will hardly cause a temporal loss and can reduce the influence due to the charging.

In the following, description will be made on a variety of embodiments of the electron beam apparatus according to the present invention, other than the embodiment illustrated in FIG. 8.

Figure 33:
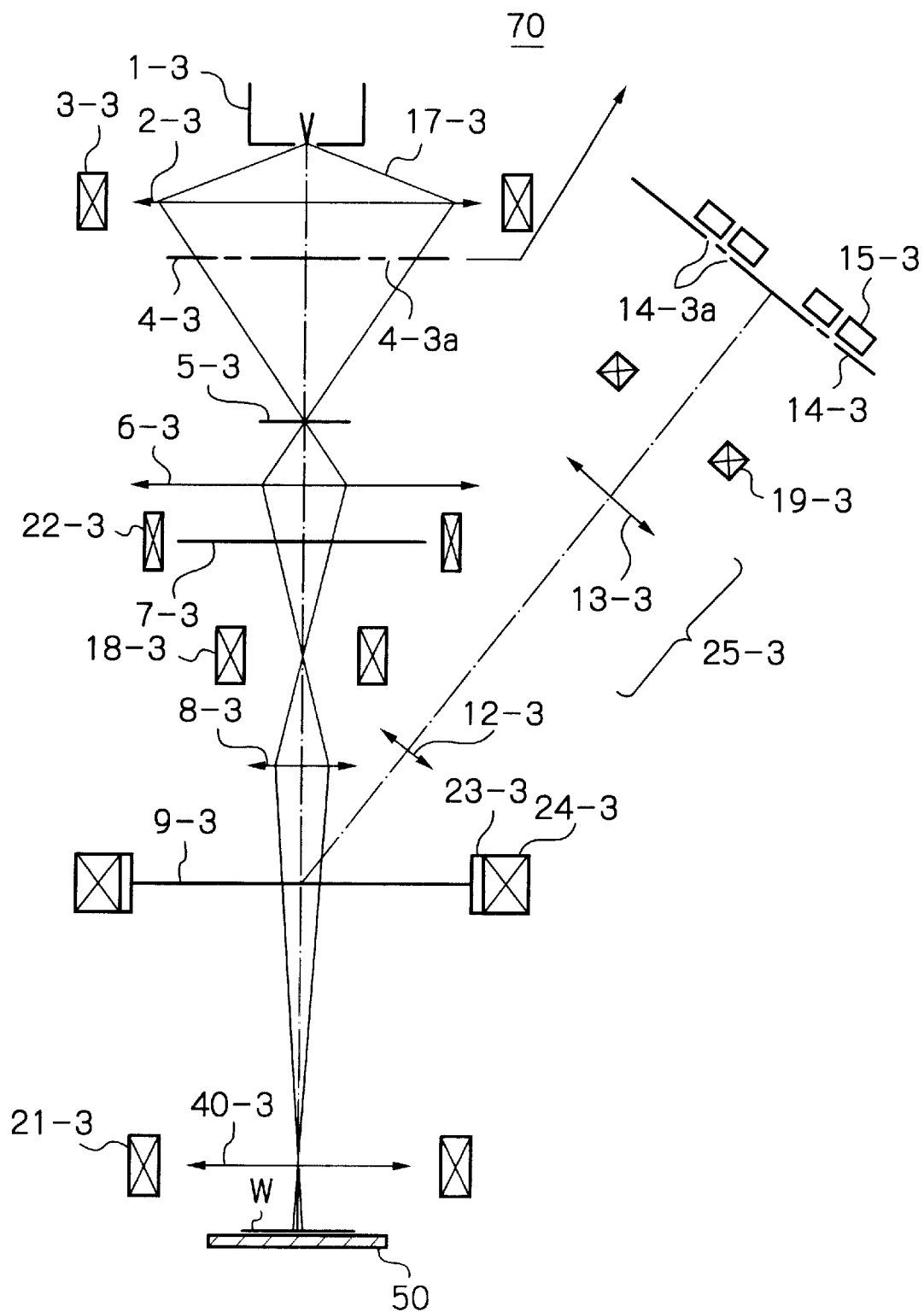
FIG. 33 schematically illustrates another embodiment of an electron beam apparatus according to the present invention.

FIG. 33 illustrates one embodiment of the electro-optical system 70 which is applicable to the electron beam apparatus according to the present invention. This embodiment has a function of rotating a plurality of apertures of the multi-aperture plate about the optical axis for adjustment in order to produce emitted electrons into a multi-beam.

Figure 34:
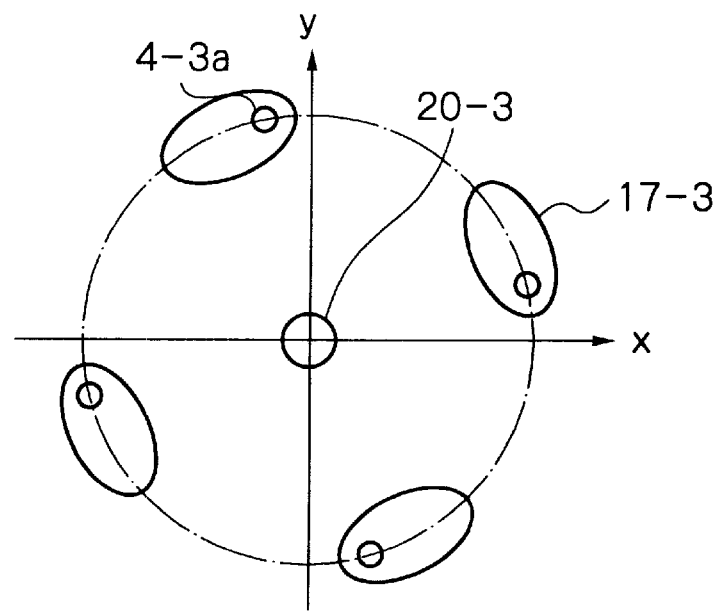
FIG. 34 is a cross-sectional view of electron beams emitted from an electron gum of the electron beam apparatus shown in FIG. 33, on a X-Y plane perpendicular to an optical axis.

As illustrated in FIG. 33, the electro-optical system 70 of this embodiment comprises an electron gun 1-3 for emitting an electron beam 17-3; and a secondary optical system (image projection unit) 25-3 for focusing secondary electrons from the surface of a wafer W irradiated with the electron beam on an aperture of the multi-aperture plate 14-3. The electron gun 1-3 is a ZrO thermal field emission electron gun, where Zr is soldered on a needle-shaped cathode made of tungsten having <001> orientation, and Zr is diffused at a leading end of the needle and activated in an oxygen atmosphere. It is known that the electron gun 1-3 thus formed emits a strong electron beam 20-3 in the direction of the optical axis (in the vertical direction on the sheet of FIG. 33, and along the Z-axis orthogonal to the sheet in FIG. 34), as shown in FIG. 34 as a beam cross-section on an X-Y plane, and emits a stronger electron beam 17-3 than that in the directions of four <001> orientations on side surfaces. The strong electron beam 17-3 is emitted in four directions about the optical axis, as illustrated in FIG. 34.

Five strong electron beams 17-3, 20-3 illustrated in FIG. 34 are converged by a condenser lens 2-3 to form a cross-over image 5-3. A multi-aperture plate 4-3 having apertures 4-3$a$ is positioned between the condenser lens 2-3 and the cross-over image 5-3 vertically to the optical axis. The multi-aperture plate 4-3 has four small apertures 4-3$a$ for discarding the electron beams 20-3 in the optical axis direction and letting the stronger electron beams 17-3 in the four directions about the optical axis pass therethrough. The electron beams passing through the four apertures 4-3$a$ are reduced by reducing lenses 6-3, 8-3, and focus four multi-beams having a diameter of 100 nm on the wafer W on a stage apparatus 50.

Generally, the center at which the electron beam 17-3 exhibits a maximum intensity deviates from the position of the aperture 4-3$a$ by a predetermined angle about the optical axis (Z-axis), so that a rotation lens 3-3 is provided to rotate the stronger electron beam 17-3 in the clockwise direction in FIG. 33 such that the center at which the electron beam 17-3 exhibits the maximum intensity is made coincident with the position of the aperture 4-3$a$. Also, the wafer W is continuously moved in the Y-axis direction by the stage apparatus 50 to scan the four stronger electron beams 17-3, which have passed through the apertures 4-3$a$, in the X-axis direction. For evaluating the wafer, the electron beams 17-3 are preferably projected in the X-axis direction at equal intervals between any beams. This is similar to the electro-optical system 70 of the electron beam apparatus which has been described with reference to FIG. 9A.

The rotation lens 3-3 is disposed at a position in the Z-axis direction identical to the condenser lens 2-3. The rotation lens 3-3 is comprised of an axially symmetric ferromagnetic core having an inverted C-shape in cross-section, and a coil wound about the optical axis and placed inside the core, and is capable of controlling the amount of rotation in accordance with the strength of a current which is applied to the coil. Further, the condenser lens 2-3 is configured as a uni-potential lens which has an upper electrode and a lower electrode connected to the ground, and a central electrode applied with a negative high voltage. Therefore, each electron beam has small energy at the position of the central electrode, and can be rotated in a small magnetic field produced by the rotation lens.

Figure 35:
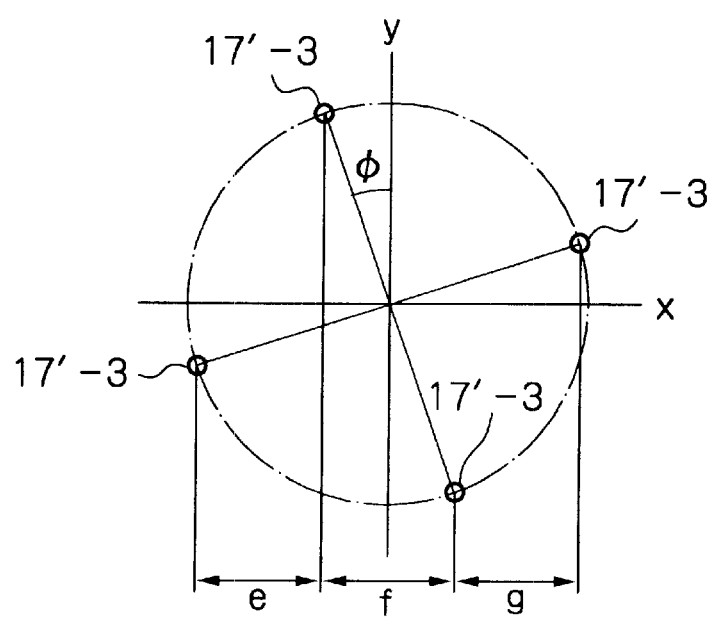
FIG. 35 is a drawing for explaining on how to design positions of four electron beams which are parallel to each others in a scanning direction.

FIG. 34 shows four stronger electron beams 17'-3 on the X-Y plane passing through the optical axis in parallel with the scanning direction (X-axis direction), at positions displaced by an angle $\phi$ from the Y-axis. As shown in FIG. 35, for spacings e, f, g in the X-axis direction to be equal to one another, e=cos$\phi$−sin$\phi$, f=2 sin$\phi$, and g=cos$\phi$−sin$\phi$, so that if the angle $\phi$ is set to satisfy:

$$2\sin\phi = \cos\phi - \sin\phi$$

the spacings e, f, g of the four electron beams 17'-3 in the X-axis direction can be made equal.

The process of adjusting the angle $\phi$ for the four electron beams 17'-3 is performed by a rotation lens 18-3. The rotation lens 18-3 is disposed coincident with the cross-over position of the electron beams 17'-3, such that the magnification of the cross-over image does not vary even if the intensity of the rotation lens 18-3 is changed.

Secondary electrons emitted from the wafer W are enlarged by an objective lens 40-3 to create an enlarged image approximately four times in front of a Wien filter (ExB filter) 23-3, deflected by the ExB filter to the right in FIG. 28, and focused by magnification lenses 12-3, 13-3 on a multi-aperture plate 14-3 in the secondary optical system. The multi-aperture plate 14-3 comprises four apertures 14-3$a$ (larger than the apertures 4-3$a$), and all electrons approaching nearby pass through the apertures and are detected by a detector 15-3. However, a rotating angle of each aperture 14-3 must match a rotating angle of each electron beam 17'-3 so as to prevent electrons generated from the surface of the wafer by each of the four primary electron beams 17'-3 from failing to enter the corresponding apertures 14-3$a$ and entering adjacent apertures. The process of matching the rotating angles is executed by a rotation lens 19-3 which is positioned between the magnification lenses 12-3, 13-3 and the multi-aperture plate 14-3.

The resolution of the electro-optical system 70 illustrated in FIG. 33 is determined by aberration of the objective lens 40-3. To reduce the aberration, a magnetic lens 21-3 is positioned near the objective lens 40-3. The magnetic lens 21-3 superimposes a lens electric field with a lens magnetic field to reduce the aberration. The position of the rotation lens 3-3 in the Z-axis (optical axis) direction is set as a position at which a maximum value of the magnetic field matches the position of the electrode which is applied with the lowest voltage, in consideration of voltages applied to respective electrodes of the electrostatic lens 2-3. In FIG. 33, the electron beam 20-3 emitted from the electron gun 1-3 in the optical axis direction is not utilized because the multi-aperture plate 4-3 is provided with no aperture corresponding thereto.

In the electro-optical system 70 illustrated in FIG. 33, defects on the surface of the wafer are detected by comparing an image generated by a captured image signal with standard pattern data, or by comparing detected images of dies with one another, and the defects on the surface of the wafer are reviewed by observing an image produced by scanning the beam on a monitor which is synchronized with the primary electron beam scanned on the surface of the wafer. Also, the pattern line width is measured based on an image produced by scanning the primary electron beam in the short side direction of a pattern on the surface of the wafer, while a pattern potential is measured by applying a negative potential to the electrode closest to the surface of the wafer, and selectively driving secondary electrons emitted from a pattern on the surface of the wafer having a high potential back to the wafer side.

As described above, the electro-optical system 70 illustrated in FIG. 33 is provided with a rotation lens near the electron gun to rotate electron beams about the optical axis, thereby eliminating a deviation of the central position at which electron beam exhibits the maximum intensity from the position of the hole, i.e., the aperture. In this way, the central position at which the electron beam exhibits the maximum intensity is highly accurately brought in line with the position of the hole. Also, in the process of scanning the four stronger electron beams in the X-axis direction on the wafer, the rotation lens is provided to rotate the four electron beams, thereby making it possible to adjust the spacings between the four electron beams projected in the X-axis direction to be equal between any beams. By positioning the rotation lens just at the cross-over position of the electron beams, it is possible to avoid the influence caused by changing the intensity of the rotation lens on the magnification of the cross-over image and focusing conditions.

Further, the aberration of the objective lens, which determines the resolution of the optical system can be reduced by providing the magnetic lens near the objective lens and adjusting the lens. Since the magnetic lens is positioned near an aperture image on the wafer, the rotation of electron beams can be controlled without exerting the influence on the focusing condition of the cross-over image or the focusing condition of the aperture image. Then, the aberration of the objective lens can be reduced by superimposing the lens electric field with the lens magnetic field. Furthermore, since the rotating angle of the apertures of the multi-aperture plate for detection in the secondary optical system and the rotating angle of the secondary electron beams can be adjusted to match by the rotation lens 19-3 positioned between the magnification lenses 12-3, 13-3 and the apertures for detection, the image produced by the secondary electron beams can be brought in line with the rotating direction of the apertures for detection to reduce cross-talk.

It goes without saying that the number of multi-beams is not limited to four.

Figure 36:
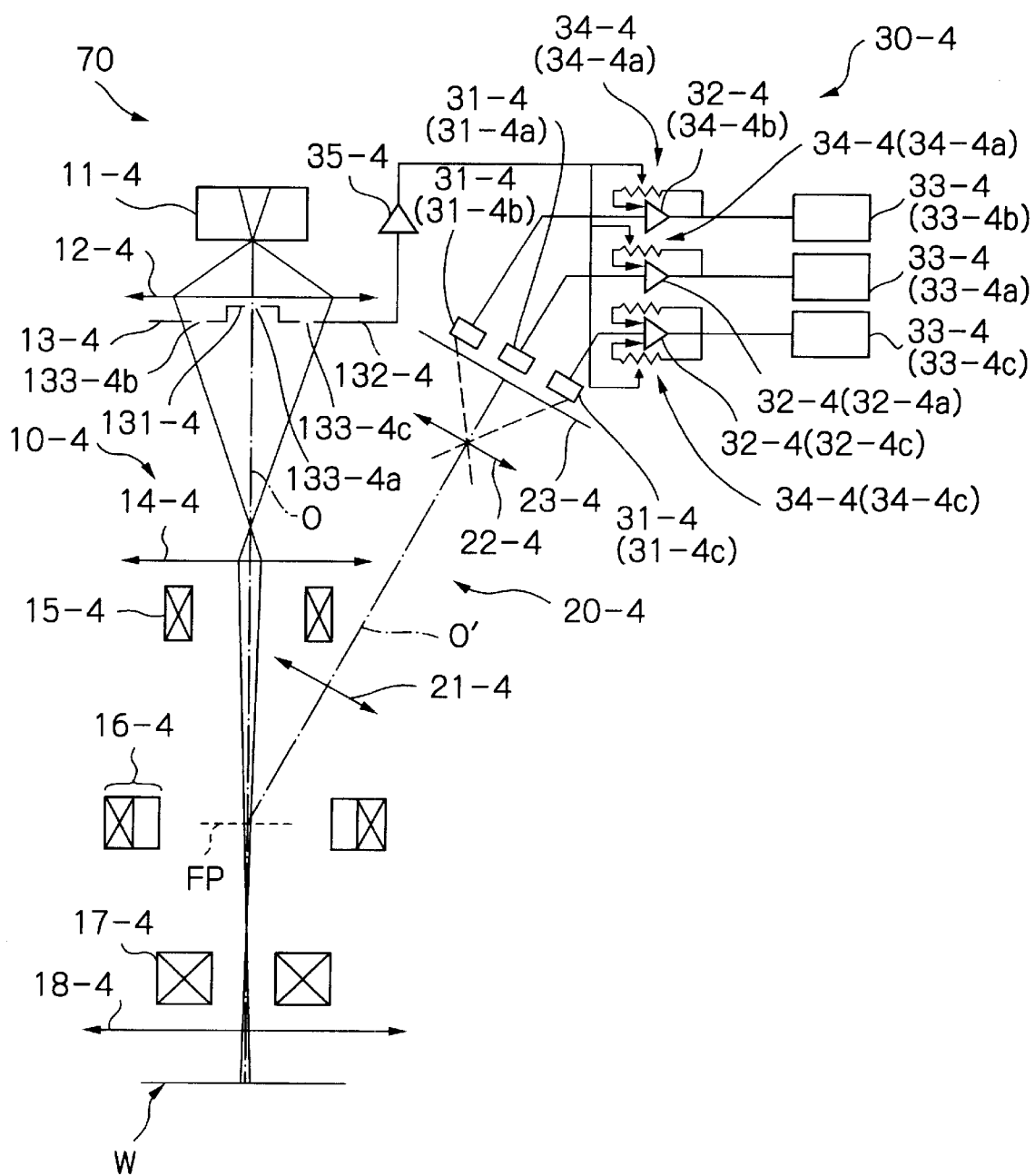
FIG. 36 illustrates another embodiment of an electron beam apparatus according to the present invention.

FIG. 36 illustrates another embodiment of the electron beam apparatus according to the present invention. This embodiment is particularly characterized by the configuration of a multi-aperture plate for generating multi-beams in the primary optical system, the ability to correct temporal fluctuations in the intensity of electron beams in real time, and the ability to correct variations of the multi-aperture plate and the transmittance of secondary electrons by adjusting the gain of an amplifier.

The electron beam apparatus illustrated in FIG. 36 comprises a primary optical system 10-4; a secondary optical system 20-4; and a testing unit 30-4. The primary optical system 10-4 comprises an electron gun 11-4 for emitting electron beams; an electrostatic lens 12-4 for converging electron beams-emitted from the electron gun 11-4; a multi-aperture plate formed with a plurality of small apertures (referred to as an aperture plate electrode as well since it functions as an electrode in this embodiment) 13-4; an electrostatic intermediate lens 14-4 for converging electron beams; an electrostatic deflector 15-4; an ExB separator/deflector 16-4; an electrostatic deflector 17-4; and an electrostatic objective lens 18-4, all of which are positioned in order with the electron gun 11-4 placed at the top, such that the optical axis O of the electron beams emitted from the electron gun is normal to the surface of a wafer W (surface of a sample), as illustrated in FIG. 36.

Figure 37:
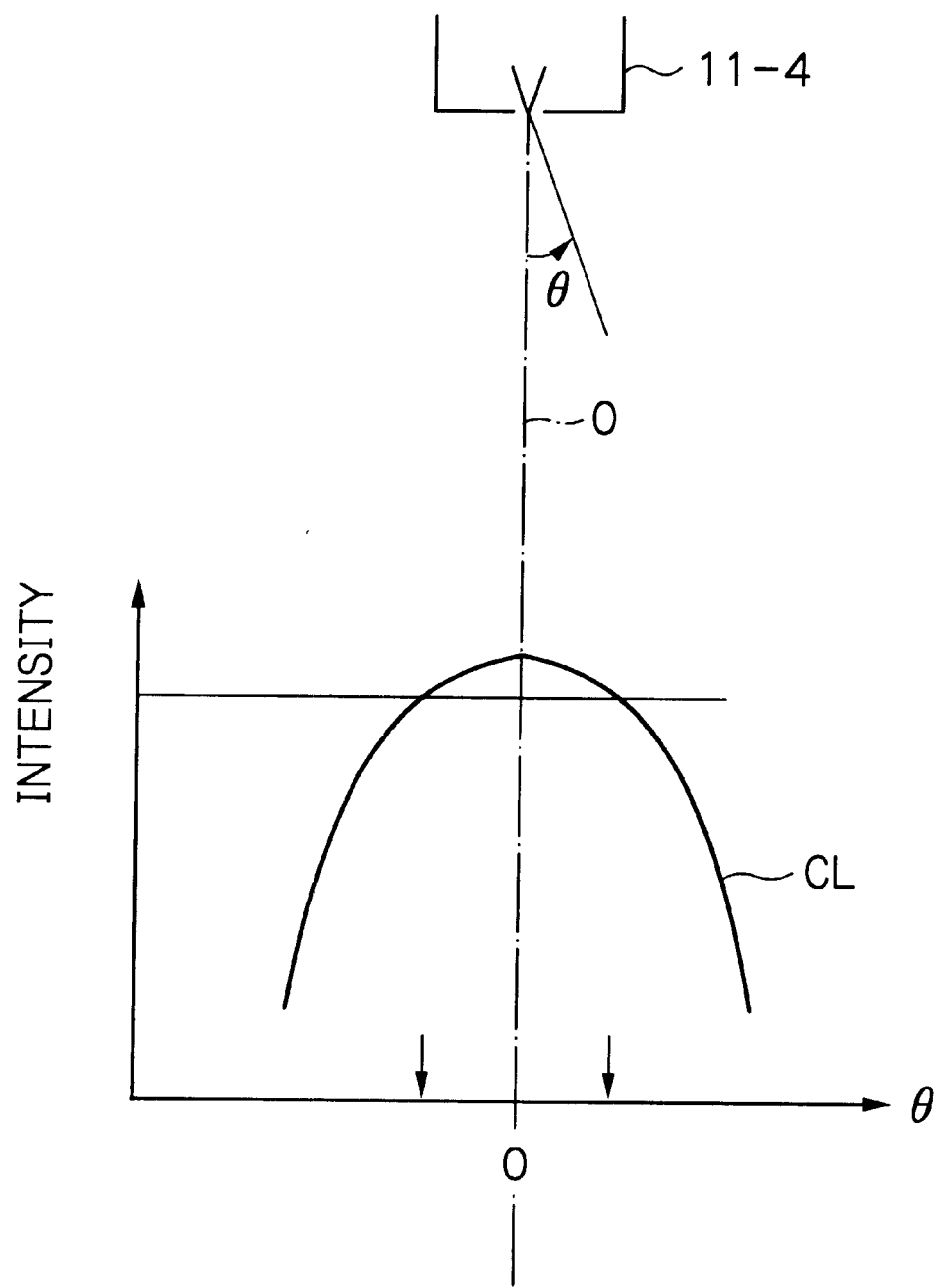
FIG. 37 shows a graph illustrating intensity distribution of electrons emitted from an electron gun.

In this embodiment, the electron gun 11-4 is a thermal field emission electron gun which has a single cathode coated with Zr on a tungsten needle, the leading end of which is pointed for enabling thermal field emission. The coating of Zr on the cathode is subsequently processed in an oxygen atmosphere to change into ZrO, resulting in a lower work function. An intensity distribution of the electron beam emitted from the electron gun 11-4 has a shape, as shown by a graph CL in FIG. 37, in which the intensity is maximal at the center (position of the optical axis) and axially symmetrically decreases at positions further away from the optical axis.

As an electron gun, the intensity of which does not decrease so much even far away from the optical axis, an electron gun having an $LaB_6$ cathode may be used, in which case a large number of beams can be generated since the electron gun can have a large emittance. Also, this electron gun is advantageously used in a space charge limited condition because of its smaller shot noise.

Figure 38A:
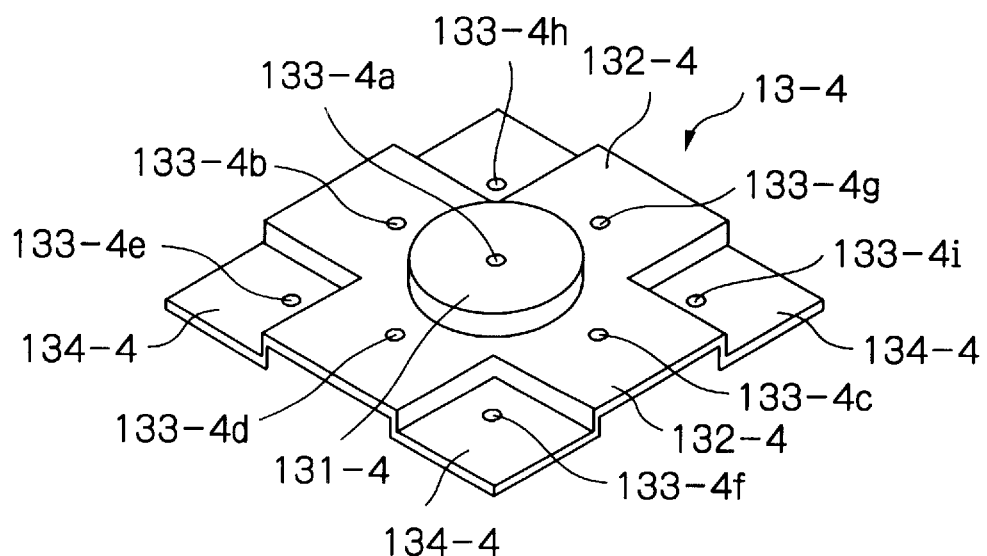
FIGS. 38A and 38B illustrate examples of an aperture electrode usable in the electron beam apparatus shown in FIG. 36.
Figure 38B:
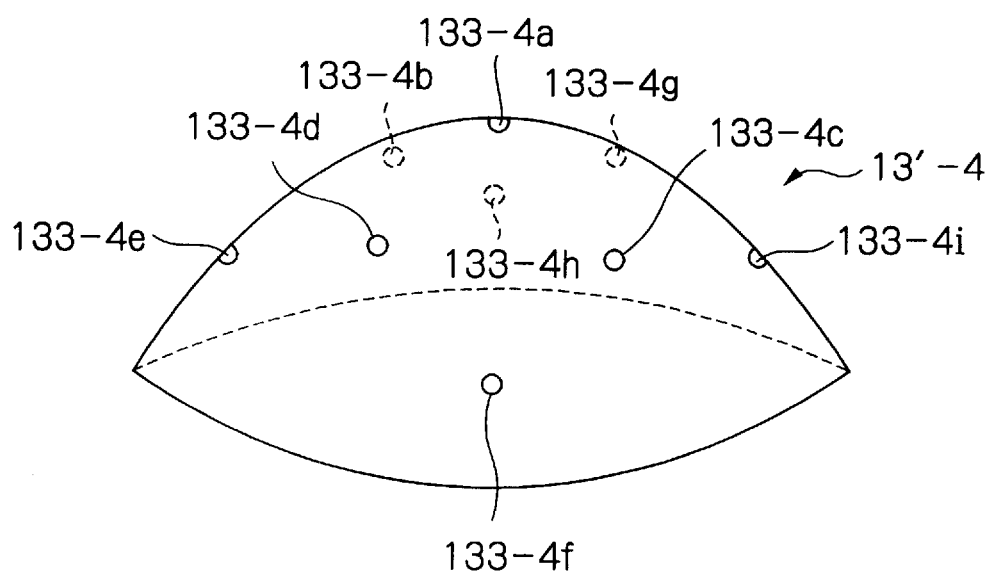

The aperture plate electrode 13-4 has a three-step structure, as illustrated in FIGS. 36 and 38A, for correcting field curvature of the primary optical system 10-4, where a central portion 131-4 protrudes more to the electron gun 11-1 than the remaining peripheral portion 132-4, and four corner portions 134-4 protrude to the side opposite to the electron gun. The aperture plate electrode 13 is made, for example, of a refractory metal such as Ta, Pt or the like. In this example, as illustrated in FIG. 38, it is formed with a total of nine apertures in a matrix of three rows and three columns, i.e., small holes (or apertures) 133-4a–133-4i. The central portion 131-4 is formed with the hole 133-4a, the peripheral portion 132-4 is formed with holes 133-4 (133-4b, 133-4c, 133-4d and 133-4g), and the four corner portions 134-4 are formed with holes 133-4(133-4e, 133-4f, 133-4h and 133-4i), and positioned as illustrated in FIG. 38A. The number of these holes is not limited to nine. These holes have the shape of 2-$\mu$m$\phi$ circle, and the pitch between adjacent holes is 1000 $\mu$m, although the size and pitch may be arbitrarily selected. It should be noted that the holes 133-4b, 133-4c, 133-4d and 133-4g are positioned on a circle about the optical axis, and that the holes 133-4e, 133-4f, 133-4h and 133-4i are positioned on the same circle. Then, a shift amount λ of the stepped structure is a value corresponding to the field curvature of the primary optical system. The hole 133-4a positioned on the optical axis O is closer to the electron gun than the other holes 133-4b, 133-4c, 133-4d and 133-4g by the value λ corresponding to the field curvature, and the holes 133-4b, 133-4c, 133-4d and 133-4g are closer to the electron gun than the holes 133-4e, 133-4f, 133-4h and 133-4i by the value λ corresponding to the field curvature. In the aperture plate electrode 133-4 illustrated in FIG. 38[A], the central portion 131-4 is circularly protruded, however, it may be rectangularly protruded. Also, the central portion 131-4 and portion 132-4 may be circularly protruded with respect to the portion 134-4. Further, as indicated by 13'-4 in FIG. 38[B], the aperture plate electrode may be in a curved shape having a convex central portion. In this case, similar to the aperture plate electrode in FIG. 38[A], the holes 133-4b, 133-4c, 133-4d and 133-4g are positioned on the same circumference about the optical axis, while the holes 133-4e, 133-4f, 133-4h and 133-4i are positioned on the same circumference. Then, the hole 133-4a positioned on the optical axis O is closer to the electron gun than the other holes 133-4b, 133-4c, 1333-4d and 133-4g by the value λ corresponding to the field curvature, and the holes 133-4b, 133-4c, 133-4d and 133-4g are closer to the electron gun than the holes 133-4e, 133-4f, 133-4h and 133-4i by the value λ corresponding to the field curvature.

Figure 39:
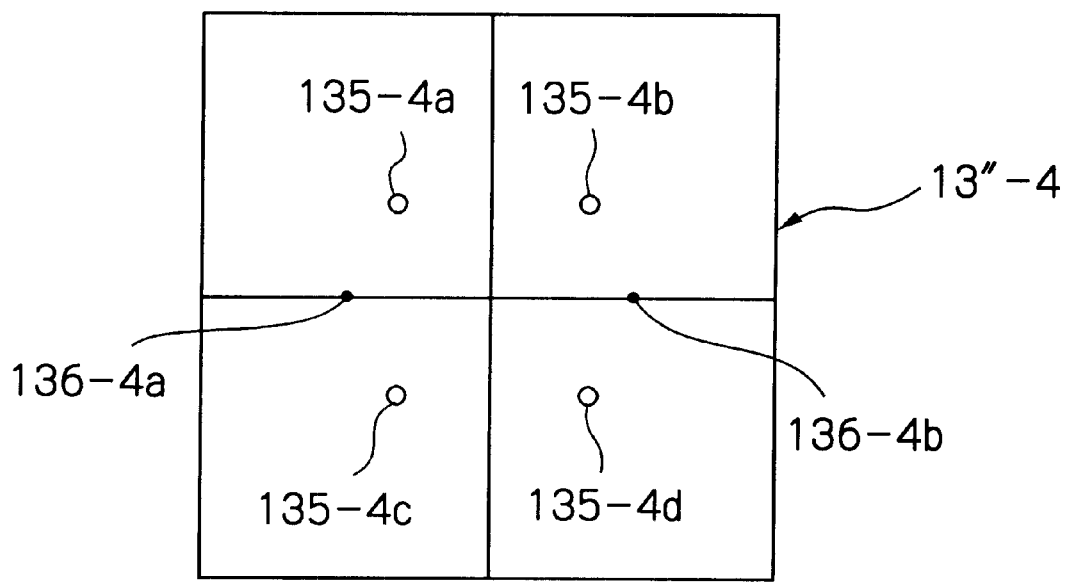
FIG. 39 shows another example of an aperture electrode usable in the electron beam apparatus shown in FIG. 36.

The electrostatic deflectors 15-4 and 17-4 are octal pole deflectors in this embodiment. Since the octal pole deflectors 15-4 and 17-4, electrostatic lenses 12-4, 14-4 and 18-4 are of known structure per se, detailed description on them is omitted. The ExB separator, i.e., ExB deflector 16-4 has been already shown in FIG. 10. Also, the small holes formed through the aperture plate electrode are not limited to a matrix of three rows and three columns. As shown in FIG. 39 as aperture plate electrodes 13"-4, with four circular small holes 135-4a –135-4d, or two circular small holes 136-4a and 136-4b, electron beams passing through the respective small holes can be made identical in beam intensity. In addition, since the distances from the optical axis are equal to one another, the field curvature need not be corrected.

Turning back to FIG. 36, the secondary optical system 20-4 comprises converging lens 21-4 and 22-4 positioned along an optical axis O' inclined by a predetermined angle to the optical axis O in the vicinity of a focal plane FP near the ExB deflector 16-4 in the primary optical system; and a multi-aperture plate 23-4. The multi-aperture plate 23-4 is formed with nine apertures (three of which are only illustrated in FIG. 36) in a matrix of three rows and three columns, corresponding to the holes of the multi-aperture plate 13-4 in the primary optical system. The electro-optical system 70 has a detector 31-4 (only 31-4a, 31-4b, 31-4c are illustrated in FIG. 36) for each aperture of the multi-aperture plate 23-4. Signal processors 33-4 (only 33-4a, 33-4b, 33-4c are illustrated in FIG. 36) are connected to the respective detectors 31-4 through amplifiers 32-4 (only 32-4a, 32-4b, 32-4c are illustrated in FIG. 36), respectively. Each of the amplifiers is provided with a gain adjuster 34-4 (only 34-4a, 34-4b, 34-4c are illustrated in FIG. 36) to adjust the gain or offset value of the associated amplifier. The gain adjusters 34-4 are electrically connected to the aperture plate electrode 13-4 through a common amplifier 35-4 to send a signal indicative of a change in a current flowing through the aperture plate electrode to the gain adjusters 34-4. Since the electron beams emitted from the thermal field emission electron gun 11-4 fluctuates in the beam intensity over time, the aperture plate electrode 13-4 is insulated from the ground, and a beam current is measured to feed a measured value of beam current fluctuations back to the amplification ratio of a secondary electron signal, i.e., the gain or an offset value in real time to prevent the fluctuations in the beam current from influencing on the signal. As noted above, the number of holes formed through the aperture plate electrode is not limited to nine. In this case, as a matter of course, the number of apertures formed through the multi-aperture plate 23-4, detectors, amplifiers and the like should also be the same as that number, and they are positioned correspondingly. The apertures are shaped in a circle having a diameter of 2 $\mu$m$\phi$, and the pitch between adjacent apertures is 1200 $\mu$m. The holes of the aperture plate electrode and the holes of the aperture plate may be formed in a rectangle shape, not limited to a circular shape.

Next, description will be made on the operation of the electron beam apparatus illustrated in FIG. 36. An electron beam emitted from the electron gun 11-4 having a single cathode is converged by the condenser lens, i.e., electrostatic lens 12-4, and irradiated to the aperture plate electrode 13-4. The electron beam passes through a plurality of small holes 133-4 formed through the aperture plate electrode 13-4 to travel toward a sample, and is reduced by the electrostatic intermediate lens 14-4 and electrostatic objective lens 18-4 provided midway to focus on the surface of the wafer W (surface of the sample).

Secondary electrons are emitted from the surface of the wafer by the irradiation of the primary electron. The secondary electrons are accelerated, and converged by an acceleration electric field for the secondary electrons, applied between the electrostatic objective lens 18-4 and the wafer W. The resulting beam having a relatively small diameter passes through the electrostatic objective lens 18-4, and substantially focuses in front of the focal plane FP of the primary beam. The secondary electrons are deflected to travel along the optical axis O' by the ExB deflector 16-4 at the position of the focal plane FP. The deflected secondary electrons are incident on the electrostatic lens 21-4. The electrostatic lens 21-4 is excited to focus electrons at 2 eV on the surface of the wafer in front of the lens 21-4. The secondary electrons are further enlarged by the electrostatic lens 22-4 to focus on the multi-aperture plate 23-4 for detection. The secondary electrons emitted from the surface of the wafer by beams, which have passed through the respective holes 133-4 of the aperture plate electrode 13-4, are led to the corresponding detectors through the corresponding apertures of the aperture plate 23-4.

An image formed on the multi-aperture plate 23-4 in the foregoing manner is detected through the respective apertures of the aperture plate by the detectors 31-4 positioned at the back of the aperture plate for each aperture, and are transduced to electric signals by these detectors 31-4. The signals from the detectors are amplified by the amplifier 32-4, and sent to the signal processing circuits 33-4 corresponding thereto. These signal processing circuits perform a test of the wafer for defects on the surface thereof, measurements of line widths of a formed pattern, review of defects, and the like. Then, with the octal pole deflectors 15-4 and 17-4, a predetermined area on the surface of the wafer is scanned by a plurality of electron beams which travel through the primary optical system 10-4 for conducting a test and the like about the area. In this event, by optimizing the deflection sensitivity ratio of the octal pole deflectors by a known method, a blurred beam can be minimized, when largely deflected, depending on at which position in the vicinity of the main surface of the electrostatic objective lens 18-4, a deflected trajectory defines the Z-axis direction position on the optical axis. For scanning over the entire surface of the wafer with the beam, the scanning of the beam within the above area is performed in combination with a movement of the surface of the wafer in the X-Y direction.

For amplifying a signal by the amplifier 34-4, the gain or offset value is adjusted by a gain adjuster for each amplifier, in order to correct the non-uniformity in the amounts of the electron beams passing through the small holes of the aperture plate electrode 13-4. In this event, the electron beam is irradiated to measure time fluctuations in a current which flows through the aperture plate electrode, and the result is input to the gain adjuster of the amplifier in the secondary electron detectors. While the foregoing description has been made on an example which uses the aperture plate electrode 13-4 in a stepped shape in combination with the amplifier which can adjust the gain or offset value, a flat aperture plate electrode may be used in combination with a gain adjustable amplifier.

For testing the surface of the wafer for defects, measuring critical dimension of a pattern, reviewing the defects, and the like using the electron beam apparatus illustrated in FIG. 36, a wafer formed with no pattern is set at a predetermined position, and the electron beam apparatus is operated in order to previously correct the size of the small holes for forming beams on the aperture plate, and variations in the secondary electron transmittance. Then, the respective amplifiers are corrected for the gain and offset value by the respective gain adjusters 34-4 such that the respective amplifiers 324 generate the same outputs. Next, a wafer under testing is set, and the electron beam apparatus is operated as described above to detect secondary electrons emitted from the surface of the wafer by the detectors, and electric signals amplified by the amplifiers are processed by the signal processing circuits 33-4. This signal processing circuit may be replaced with a defect detector circuit for detecting the presence or absence of defects in patterns formed on the wafer and the positions of defects by comparing the processed signals with reference data on patterns as designed, stored in a storage unit, for example, by a comparator circuit, not shown, to conduct a defect test. Alternatively, the signal processing circuits may be replaced with a line width measuring apparatus to measure line widths of patterns formed on the surface of the wafer. Further, a monitor such as a CRT may be connected to the signal processing circuits to review the defects. Furthermore, when the primary optical system may be provided somewhere with a function of blanking beams, the electron beam apparatus can also be used as an EB tester.

According to the electron beam apparatus illustrated in FIG. 36, since temporal fluctuations in the intensity of electron beam from the electron gun can be corrected in real time, a test can be correctly conducted. Also, since variations in the multi-aperture plate and the transmittance of secondary electrons can be corrected by adjusting the gains of the amplifiers, outputs from the respective detectors are free from variations.

FIG. 40 illustrates an electro-optical system 70 which is applicable to the electron beam apparatus according to the present invention. As illustrated in FIG. 40, in this embodiment, an electron beam emitted from an electron gun 1-5 is enlarged by three condenser lenses 3-5, 5-5, 6-5 to focus a light source image on an incident pupil of a final lens 8-5 (indicated by a solid line 16-5 in the figure). A multi-aperture plate 4-5 formed with four holes at equal intervals on the same circumference about the optical axis is provided on the wafer W side of the condenser lens 3-5. Electron beams passing through these holes are reduced by two condenser lenses 5-5, 6-5 and an objective lens 8-5, and focused on the wafer W (indicated by a broken line 14-5). An ExB separator 7-5 is provided on the electron gun side of the objective lens 8-5 for deflecting a primary electron beam by 10° to the right of the traveling direction, and for deflecting secondary electron beams by 30° to the right of the traveling direction. In other words, the amount of deflection of the primary electron beam by an electric field generated by the ExB separator 7-5 is set one half of the amount of deflection by a magnetic field. Since deflection chromatic aberration by the electric deflection is one half of deflection chromatic aberration by the magnetic deflection, the deflection chromatic aberration by the electric deflection and the deflection chromatic aberration by the magnetic deflection cancel each other, thereby making it possible to reduce the deflection chromatic aberration substantially to zero. Secondary electrons emitted from four points on the wafer W irradiated with the primary electron beams form four enlarged images in front of an magnification lens 10-5, and are further enlarged by the magnification lens 10-5 to focus images on the multi-aperture plate 11-5 having four holes (indicated by one-dot chain lines 12-5). Detectors 13-5 are positioned at the back of the respective holes of the multi-aperture plate for detecting the focused secondary electron images to output the images as electronic signals.

Since the center of deflection of the ExB separator 7-5 does not match the focal point of the primary electron beam, the primary electron beam is likely to suffer from larger deflection aberration. For this reason, the amount of deflection by the magnetic field is selected twice the amount of deflection by the electric field to reduce the deflection chromatic aberration. Specifically, the electron beam is deflected by 10° to the left by the electric field, and by 20° to the right by the magnetic field, such that the electron beam is deflected by 10° to the right as a balance. Corresponding to this, the wafer W is inclined by 10° for vertically receiving the incident primary electron beams. Of course, the wafer may be placed horizontally and the primary optical system be inclined by 10°.

A cathode 2-5 within the electron gun is a cathode for a thermal field emission electron gun which has an optical axis direction in <100> orientation, and emits stronger beams in four directions of <310> or <100> orientations on side surfaces than in the optical axis direction, so that emission in <100> orientation is discarded, and emission in <310> or <100> orientation on the side surfaces alone is passed below. Since the radiation in <310> or <100> orientation on the side surfaces are emitted in a sufficiently wide direction, a beam current irradiated to the respective holes of the multi-aperture plate 4-5 hardly changes, even if the excitation of the condenser lens 3-5 is changed and the cross-over dimension on the objective lens 8-5 is largely changed, thereby making it possible to make the beam current invariant.

The condenser lenses 5-5, 6-5 may be operated as a zoom lens, i.e., without changing a cross-over focusing condition and an aperture image focusing condition, to make the magnification of the cross-over variable to adjust the beam dimension and beam current. Alternatively, the two lenses may be replaced with a zoom lens to adjust the beam spacing.

According to the electro-optical system 70 illustrated in FIG. 40, the primary optical system is comprised of four lenses, while the secondary optical system is comprised of a single lens, so that the structure is simple, and its control, i.e., control for the beam spacing, beam dimension (diameter), and beam current is facilitated. Since the cross-over is formed by the enlargement made by all the lenses, and the aperture image is formed by the reduction provided by all the lens, the optical system is simplified. Also, in the secondary optical system, a sufficient magnification can be achieved with an objective lens and a single lens behind the ExB separator.

Though the apertures of the multi-aperture plates 4-5 and 11-5 must be positioned in correspondence, the number of apertures is not limited to four but may be set to an arbitrary plural number, as a matter of course.

Figure 41:
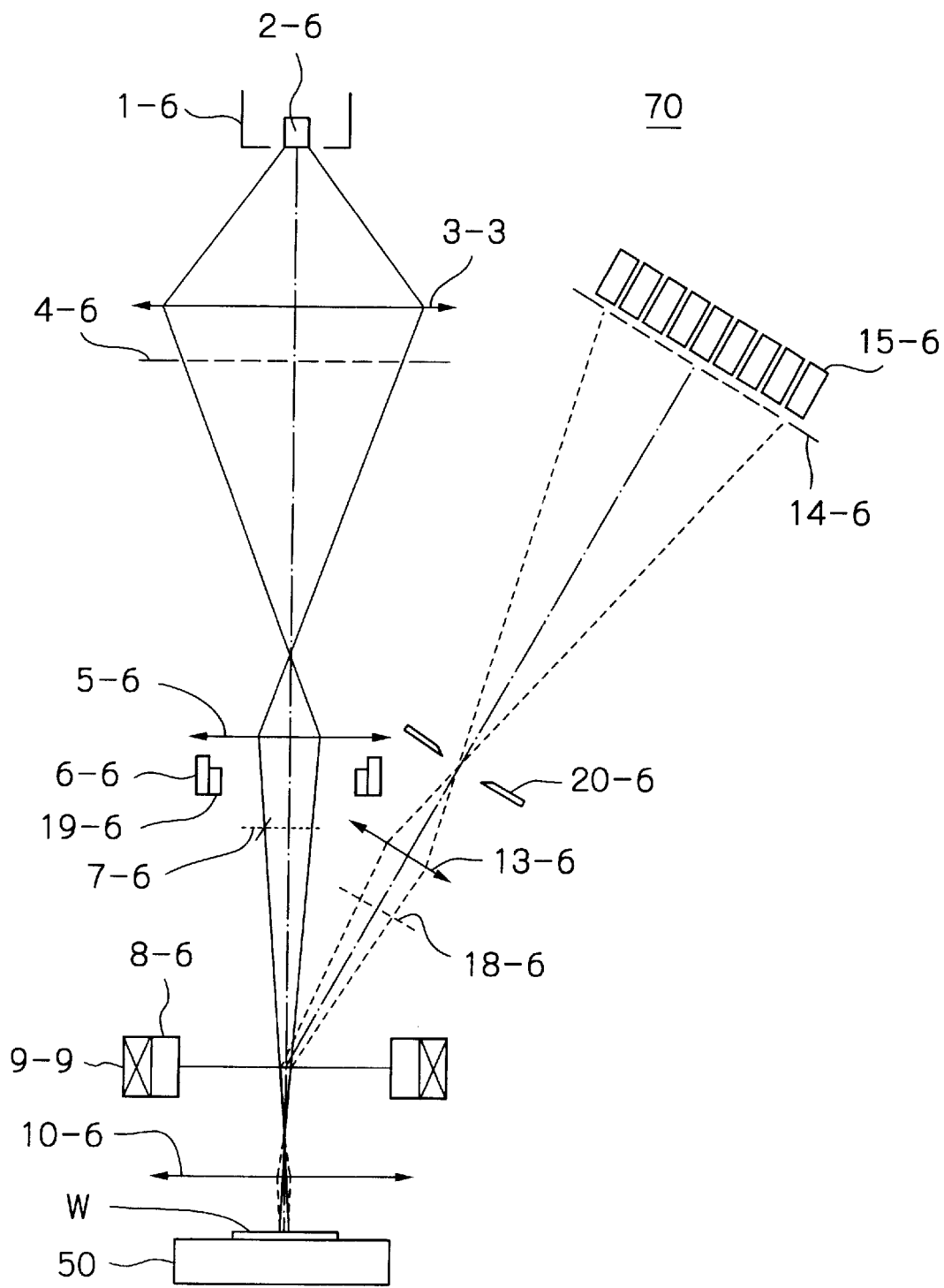
FIG. 41 schematically illustrates more further embodiment of an electron beam apparatus according to the present invention.

FIG. 41 illustrates a further embodiment of the electro-optical system 70 which is applicable to the electron beam apparatus according to the present invention. This embodiment reduces the number of lens stages as much as possible for simplification. Since the number of lens stages is reduced, the focusing and alignment of the primary electron beam and secondary electron beams can be readily achieved, and additionally the cross-talk can be reduced between the electron beams.

In the electro-optical system 70 illustrated in FIG. 41, a single crystal LaB6 cathode, which is machined in a shape which has protrusions juxtaposed on the circumference, is arranged within an electron gun 1-6. An electron beam emitted from the electron gun is converged by a condenser lens 3-6 and irradiated to a multi-aperture plate 4-6. The multi-aperture plate 4-6 has nine apertures arranged on the same circle, which are set such that the apertures, when projected on the X-axis, are spaced at equal intervals. This is similar to the case illustrated in FIG. 9A in connection with the electro-optical system 70 of the electron beam apparatus illustrated in FIG. 8. Also, the positional relationship between apertures of a multi-aperture plate 14-6 in the secondary optical system, later described, and a plurality of detectors 15-6 is similar to that illustrated in FIG. 9A.

An electron beam emitted from the electron gun 1-6 passes through the apertures of the multi-aperture plate 46 for conversion into multi-beams which are focused at a point 7-6 by a reducing lens 5-6, and is further focused on a wafer W through an objective lens 10-6. The objective lens 10-6 is a uni-potential type which has a central electrode applied with a positive high voltage, and a plurality of primary electron beams, i.e., multi-beams are decelerated by the objective lens when they are irradiated to the wafer W.

On the other hand, secondary electrons emitted from the wafer by the irradiation of the multi-beams are accelerated by an electric field created by the objective lens 10-6, deflected toward the secondary optical system by an ExB filter comprised of an electrostatic deflector 8-6 and an electromagnetic deflector 9-9, and focused on the multi-aperture plate 14-6 for the secondary optical system through an magnification lens 13-6. A dotted line 18-6 indicates the trajectory of the secondary electrons emitted vertically from the wafer, out of the secondary electrons emitted by the irradiation of the multi-beams. An aperture plate 20-6 for determining apertures for the secondary electrons is disposed at a position at which the secondary electrons create a cross-over. In this way, beams with large aberration can be removed.

In the electro-optical system 70 of FIG. 41, an optical path common to both primary electron beam and secondary electron beams extends between the ExB filter and the wafer W, where the objective lens 10-6 exists alone. Therefore, the focusing of the lens and the alignment of the lens are easy for the primary electron beam and secondary electron beams. This aspect is also similar to the electro-optical systems illustrated in FIG. 8 and the like. Stated another way, with respect to the electro-optical system 70 of FIG. 41, the objective lens 10-6 is only required to satisfy a focusing condition for the primary electron beam. The secondary electron beam can be focused, for example, by mechanically moving the positions of the multi-aperture plate 14-6 and numerical aperture plate 20-6.

The alignment to the objective lens 19-6 can be performed by an aligner 10-6 without shifting the axis of the secondary electrons. The alignment to the magnification lens 13-6 can be performed by adjusting the amount of deflection with the ExB filter, i.e., ExB separator, while satisfying the Wien condition for the primary electron beam, without exerting the influence on the axis of the primary electron beam.

A blur on the multi-aperture plate 14-6 on which the secondary electrons emitted from a point on the wafer W irradiated with the multi-beams are focused can be readily calculated if a simulation is performed with commercially available software. Also, when the beam spacing between the multi-beams is determined on the wafer, the blur on the wafer can be calculated by dividing the amount of blur on the multi-aperture plate 14-6 by the magnification from the wafer W to the aperture plate 14-6. The diameter of the numerical aperture plate 20-6 may be determined such that the amount of blur becomes smaller than the beam spacing. As an alternative method, with the diameter of the numerical aperture plate 20-6 set to a fixed value, the multi-beam spacing may be made larger than the blurred secondary electron beam converted to a value on the wafer.

In the electro-optical system 70 illustrated in FIG. 41, as is the case with the electro-optical systems of the other embodiments, since the primary electron beam is decelerated, the aberration can be reduced and the primary electron beam can be narrowed down. Also, the secondary electrons are accelerated by the objective lens, the secondary electrons, which have been emitted over a wide angle with respect to the optical axis, is also narrowed down to a fine beam bundle by the objective lens, so that the apertures in the secondary optical system can be reduced.

Figure 42:
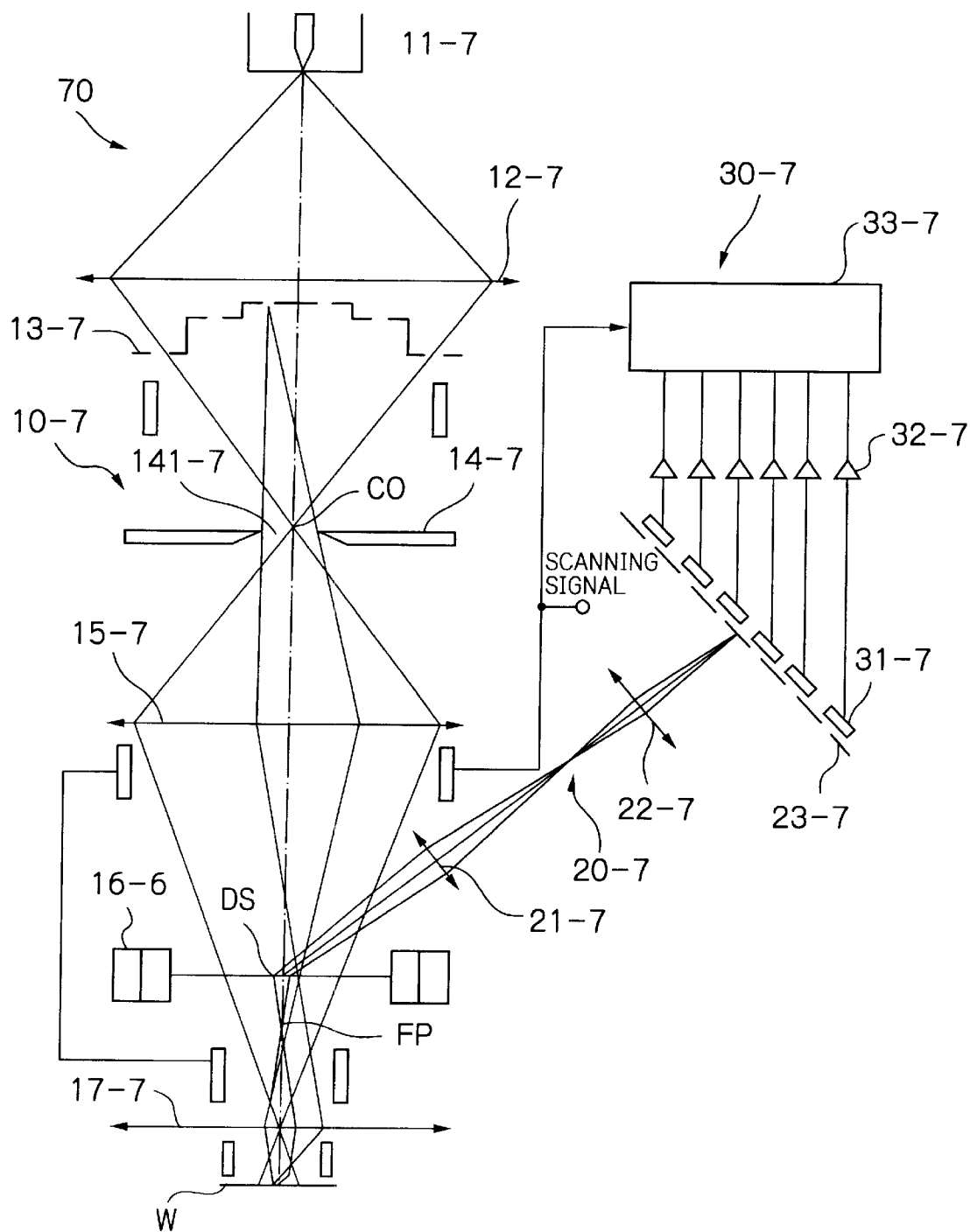
FIG. 42 schematically illustrates another embodiment of an electron beam apparatus according to the present invention.

FIG. 42 illustrates another embodiment of the electro-optical system 70 which is applicable to the electron beam apparatus according to the present invention. This embodiment comprises a primary optical system 10-7 for irradiating the surface of a wafer W with an electron beam; a secondary electron beam 20-7 as an electron beam focusing optical system for focusing secondary electrons emitted from the wafer W on a detecting plane; and a detecting system 30-7 for detecting the secondary electrons. In FIG. 42, the electron beam (primary electron beam) emitted from an electron gun 11-7 is converged by a condenser lens 12-7 comprised of an electrostatic lens to form a cross-over at a point CO. At this cross-over point CO, an iris 14-7 is positioned having an aperture 141-7 for determining NA.

Below the condenser lens 12-7, a multi-aperture plate 13-7 having a plurality of apertures is placed for forming a plurality of primary electron beams. Each of the primary electron beams formed by the multi-aperture plate 13-7 is reduced by a reducing lens 15 comprised of an electrostatic lens, and is focused on a deflection main surface DS of an ExB filter, i.e., ExB separator 16-7. Then, after focused at the point DS, the primary electron beam is focused on the wafer W by an objective lens 17-7 comprised of an electrostatic lens. A plurality of primary electron beams exiting the multi-aperture plate 13-7 are deflected by a deflector positioned between the reducing lens 15-7 and an objective lens 17-7 such that they simultaneously scan on the surface of the wafer W.

For correcting field curvature aberration for the reducing lens 15-7 and objective lens 17-7, the multi-aperture plate 13-7 has a stepped structure, as illustrated in FIG. 42, where the distance from the condenser lens 12 is larger from the center to the periphery.

A plurality of focused primary electron beams are irradiated to a plurality of points on the wafer W, and secondary electrons are emitted from the plurality of irradiated points. The emitted secondary electrons are attracted by an electric field of the objective lens 17-7, and narrowed down and converged to focus at a point FP in front of the ExB separator 16-7. This is because each primary electron beam has energy of 500 eV on the surface of the wafer W, whereas the secondary electron beams merely have energy of several eV. A plurality of secondary electron beams emitted from the wafer W are deflected outward of the optical axis of the primary optical system 10-7 by the ExB separator 14-7 to be separated from the primary electron beam, and directed into the secondary optical system 20-7.

The secondary optical system 20-7 includes magnification lenses 21-7, 22-7 comprised of electrostatic lenses. The secondary electron beams passing through these magnification lenses 21-7, 22-7 pass through a plurality of apertures of a multi-aperture plate 23-7 in the secondary optical system, and focus on a plurality of detectors 31-7. A plurality of apertures formed through the multi-aperture plate 23-7 positioned in front of the detectors 31-7 correspond in a one-to-one relationship to a plurality of apertures formed through the multi-aperture plate 13-7 in the primary optical system, and a plurality of detectors 31-7 also correspond in a one-to-one relationship to them.

Each of the detectors 31-7 transduces a detected secondary electron beam to an electric signal indicative of the intensity. The electric signal thus output from each detector is amplified by each amplifier 32-7 before received by an image processor 33-7 which converts the electric signal to image data. The image processor 33-7 is supplied with a scanning signal for deflecting the primary electron beam, so that the image processing unit 33-7, by processing the electric signal based on the scanning signal, can form image data representative of the surface of the wafer W. Defects on the wafer can be detected by comparing the image of the wafer formed in this way with a standard pattern.

In addition, line widths of patterns on the wafer can be measured by moving the wafer close to the optical axis of the primary optical system by registration, line-scanning the wafer to extract a line width evaluation signal, and calibrating the line width evaluation signal as appropriate.

When the primary electron beams passing through the apertures of the multi-aperture plate 13-7 in the primary optical system are focused oh the surface of the wafer, and the secondary electrons emitted from the wafer are focused on the detectors 31-7, particular attention is required to minimize the influence exerted by three types of aberrations: comma aberration, field curvature and astigmatism occurring in the primary optical system and secondary optical system. Also, in regard to the relationship between the spacing between points irradiated by a plurality of primary electron beams and the secondary optical system, cross-talk between a plurality of electron beams can be eliminated by spacing the respective primary electron beams apart by a distance larger than the aberration in the secondary optical system.

Figure 43:
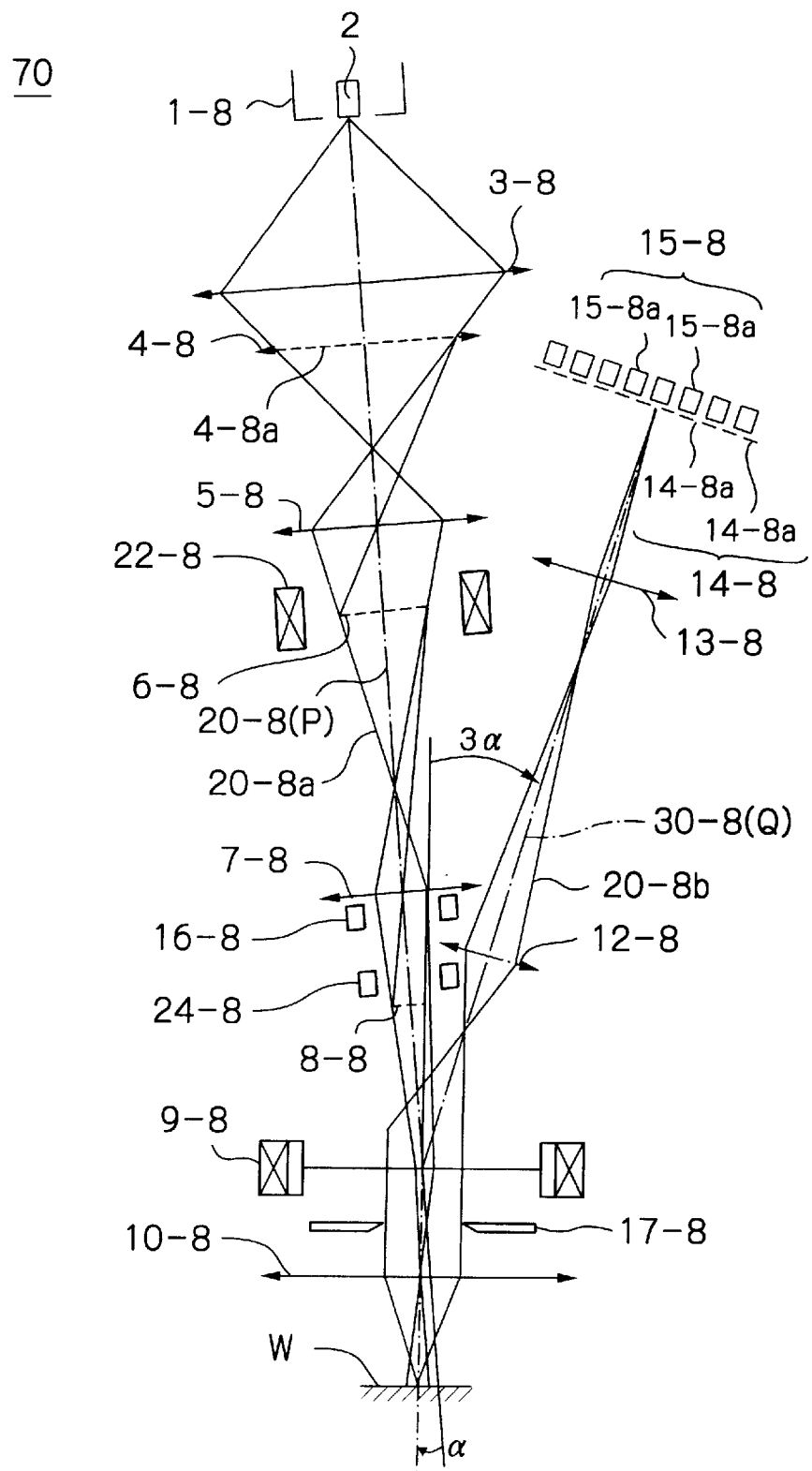
FIG. 43 schematically illustrates another embodiment of an electron beam apparatus according to the present invention.

FIG. 43 illustrates a further embodiment of the electro-optical system 70 which is applicable to the electron beam apparatus according to the present invention. This embodiment can eliminate deflection chromatic aberration due to an ExB separator.

Specifically, in an electro-optical apparatus using an ExB separator, the ExB separator inevitably has aberration for a primary optical system, giving rise to such a problem that deflection chromatic aberration, in particular, is large. Due to this deflection chromatic aberration, the primary electron beam cannot be focussed down to have a predetermined beam diameter on the surface of a wafer.

The electro-optical system 70 illustrated in FIG. 43 includes a primary optical system 20-8, a secondary optical system 30-8, and a detector 15-8. The primary optical system 20-8, which is an irradiation optical system for irradiating the surface (sample surface) of a wafer W with a plurality of primary electron beams, comprises an electron gun 1-8 for emitting a primary electron beam; a multi-aperture plate 4-8 having a plurality of two-dimensionally arranged small holes 4a; electrostatic lenses 3-8, 5-8, 7-8 for converging the primary electron beam emitted from the electron gun 1-8; an electrostatic deflector 16-8; an ExB separator 9-8; a numerical aperture 7-8; and an objective lens 10-8 which is an electrostatic lens.

The ExB separator is designed such that a deflection angle by an electromagnetic deflector is twice as wide as an electrostatic deflector. Therefore, by the action of the ExB separator 9-8, primary electrons are deflected by a to the left in the figure, while secondary electrons are deflected by α to the right. While the installation of the primary optical system inclined by α (for example, 5°) is problematic, the primary electron beam is separated from the primary electron beam by α (for example, 20°), so that they can be readily separated. Thus, advantageously, the deflection chromatic aberration due to the ExB separator is not generated in the primary electron beam.

As illustrated in FIG. 43, the primary optical system 20-8 is arranged such that the electron gun 1-8 is positioned at the top, and the primary electron beam emitted from the electron gun has an optical axis P vertical to the surface of the wafer W. Since no deflection chromatic aberration is generated in the primary electron beam in the ExB separator 9-8, the primary electron beam can be converged.

The secondary optical system 30-8 comprises an magnification lens 12 comprised of an electrostatic lens positioned along an optical axis Q inclined with respect to the optical axis P in the vicinity of the ExB separator in the primary optical system 20-8; and a multi-aperture plate 14-8 which has a plurality of two-dimensionally arranged apertures, i.e., small holes 14-8a. The detector 15-8 comprises a detecting element 15-8a for each small hole 14-8. The small holes 14-8a of the multi-aperture plate 14-8 correspond in number and arrangement to the small holes 48a of the multi-aperture plate 4-8 in the primary optical system. For eliminating cross-talk between a plurality of primary electron beams, the spacing between positions on the surface of the wafer irradiated with the plurality of primary electron beams is chosen to be a larger distance than aberration in the secondary optical system (aberration of the objective lens to the secondary electrons).

Figure 44:
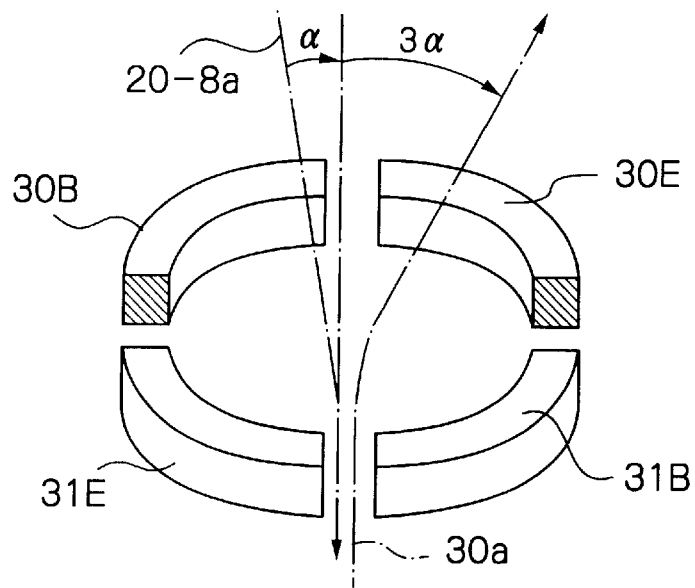
FIG. 44 is a drawing for explaining a function of an ExB separator.
Figure 45:
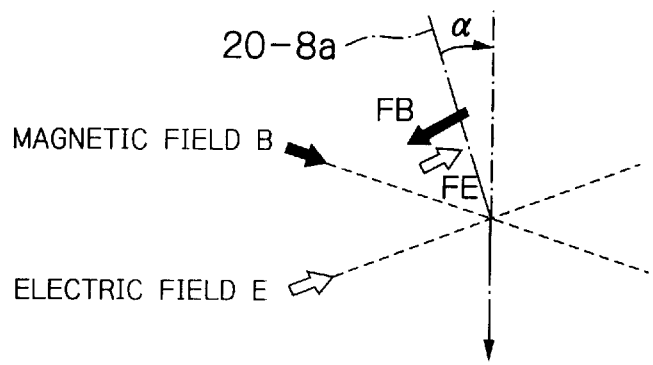
FIG. 45 is a drawing for explaining forces applied to a primary electron beam from a ExB separator.
Figure 46:
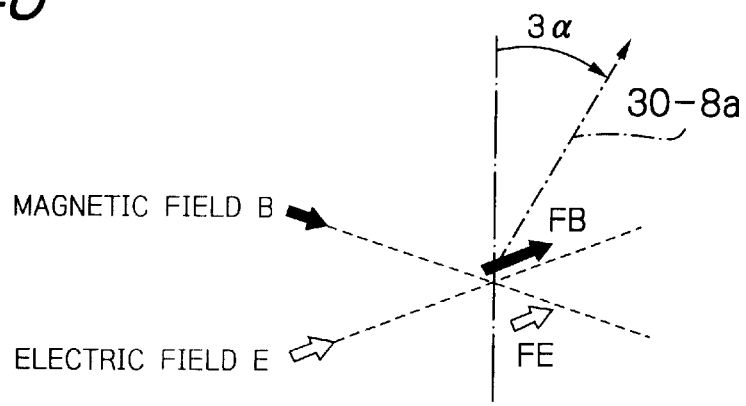
FIG. 46 is a drawing for explaining forces applied to a secondary electron beam from a ExB separator.

FIGS. 44 through 46 are perspective views for explaining the principles of the action of the ExB separator in the electro-optical system 70 of FIG. 43, wherein FIG. 44 is a schematic general view, FIG. 45 is a schematic view showing a force acting on a primary electron beam; and FIG. 46 is a schematic view showing a force acting on a secondary electron beam. As illustrated in FIG. 44, if when a magnetic core 31B for applying a magnetic field and an electrode 31E for applying an electric field are shifted by 90° in position, a force FB generated by the magnetic field and a force FE generated by the electric field act on a primary electron beam 20-8a in opposite directions, so that the beam trajectory is deflected by the difference between the two, as illustrated in FIG. 45. Specifically, assuming that a deflection angle by the electrostatic deflector is α and a deflection angle by the electromagnetic deflector is 2α, the primary electron beam is deflected by α. On the other hand, the force FB generated by the magnetic field and the force FE generated by the electric field act on the secondary electron beam 30-8a in the same direction to mutually intensify, as shown in FIG. 46, so that the secondary electron beam 30-8a is largely deflected, in the above-mentioned case, by 3α. This configuration is the same as a Wien filter which deflects a charged particle beam by an accelerating voltage.

Turning back to FIG. 43, the primary electron beam passing through the ExB separator 9-8 reaches the numerical aperture 17-8, and forms a cross-over image at the position of this numerical aperture 17-8. The primary electron beam passing through the numerical aperture 17-8 reaches the wafer W, receiving a lens action by the objective lens 10-8, to irradiate the surface of the wafer in a narrowly converged state.

From the wafer irradiated with the primary electron beam, secondary charged particles having a distribution in accordance with the surface shape, material distribution, change in potential, and the like of the wafer, i.e., secondary electrons, back scattered electrons and reflected charged particles (reflected electrons) are emitted as secondary electron beams 30-8. While any of them can be utilized depending on specifications, described herein are the secondary electrons selected for the purpose.

The emitted secondary electrons, receiving the action of the objective lens 10-8, passes through the numerical aperture 10-8 disposed at the focal position of the objective lens 10-8, and reaches the ExB separator 9-8. A magnetic field B and an electric field E, orthogonal to each other, formed by the ExB separator 9-8 are not set such that the secondary electrons from the wafer W satisfy the Wien condition. For this reason, the secondary electrons passing through the numerical aperture 17-8 are deflected by the ExB separator 9-8 to travel toward a plurality of stages of lenses 12-3, 13-8.

While the electro-optical system 70 illustrated in FIG. 43 uses the ExB separator which bends the trajectories of both the primary electron beam and secondary electron beams, the present invention is not limited to this but may employ, for example, an electromagnetic prism which lets the trajectory of the primary electron beam go straight and bends the trajectory of the secondary electron beams. The multi-aperture plate 14-8 in the secondary optical system is provided with a multiplicity of apertures 14-8$a$. The apertures 14-8$a$ are conjugate with the wafer W with respect to the objective lens 10-8 and lenses 12-8, 13-8. The secondary electrons deflected by the ExB separator further pass through a plurality of lenses 12-8, 13-8 and apertures 14-8$a$, and reach the detectors 15-8 which converts the secondary electrons to electric signals corresponding to the intensities of the secondary electrons which have reached them.

Figure 47:
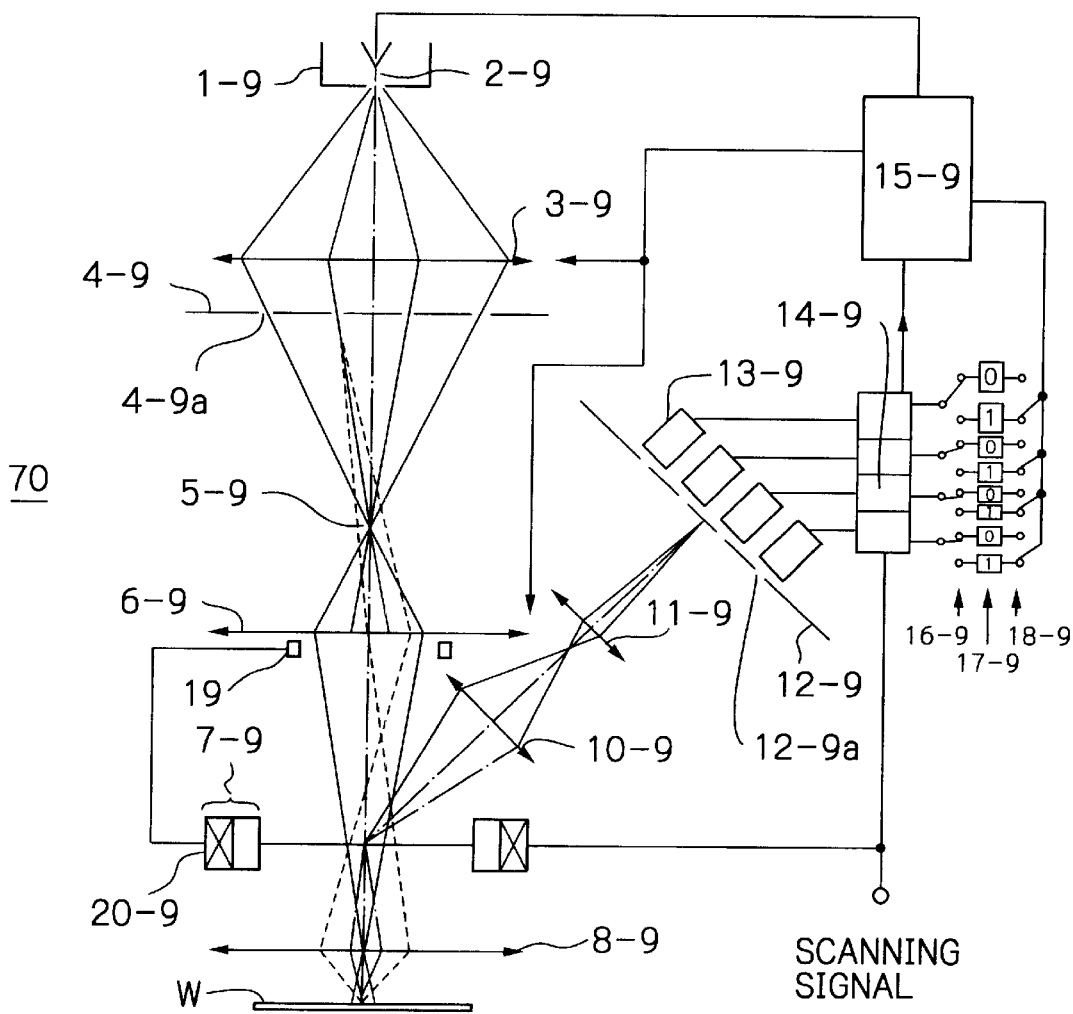
FIG. 47 schematically illustrates another embodiment of an electron beam apparatus according to the present invention.

FIG. 47 illustrates the electron beam apparatus according to the present invention. In this embodiment, an electron beam emitted from a cathode 2-9 of an electron gun 1-9 is converged by a condenser lens 3-9 to form a cross-over at a point 5-9. Below the condenser lens 3-9, a multi-aperture plate 4-9 having a plurality of apertures 49$a$ is positioned to form a plurality of primary electron beams. Each of the primary electron beams formed by the multi-aperture plate 4-9 is reduced by a reducing lens 6-9 and focused on the wafer W by an objective lens 8-9. A plurality of primary electron beams exiting the multi-aperture plate 4-9 are deflected by deflectors 19-9, 20-9 positioned between the reducing lens 6-9 and objective lens 8-9 to simultaneously scan on the surface of the wafer W.

For eliminating the influence of field curvature of the reducing lens 6-9 and objective lens 8-9, the small apertures 4-9$a$ of the multi-aperture plate 4-9 are positioned on the circumference, and points formed by projecting these apertures in the X-axis direction are set at equal intervals. This is similar to the description on the electron beam apparatus 70 of the first embodiment with reference to FIG. 9A. A plurality of points on the wafer are irradiated by a plurality of focused primary electron beams, and secondary electron beams emitted from the plurality of irradiated points are accelerated by an electric field of the objective lens 8-9 to be narrowly converged, deflected by an ExB separator 7-9, and detected by a plurality of detectors 13-9 through a secondary optical system.

The secondary optical system has magnification lenses 10-9, 11-9. The secondary electron beams passing through these magnification lenses 10-9, 11-9 focus on a plurality of apertures 12-9$a$ of a multi-aperture plate 12-9. The plurality of aperture 12$a$ of the multi-aperture plate 12-9 in the secondary optical system corresponds in a one-to-one relationship to the plurality of apertures 4-9$a$ of the multi-aperture plate 4-9 in the primary optical system. Each of the detectors 13-9 converts detected secondary electron beam to an electric signal indicative of the intensity thereof. The electric signals are each amplified by amplifiers 14-9, A/D converted, and then transmitted to an image processor 15-9 for conversion to image data. The image processor 15-9 is also supplied with a scanning signal for deflecting the primary electron beam to form an image representative of the surface of the wafer.

Defects on the wafer can be detected by comparing the image representative of the sample surface formed in the image processor 15-9 with a standard pattern. Also, line widths of patterns on the wafer can be measured by moving a pattern under evaluation of the wafer close to the optical axis of the primary optical system by registration, line-scanning the wafer to obtain a line width evaluation signal, and calibrating the line width evaluation signal as appropriate.

For focusing the primary electron beams on the surface of the wafer W and focusing the secondary electron beams emitted from the wafer W on the detecting systems 12-9, 13-9, it is desirable to minimize the influence exerted by three types of aberration, i.e., distortions, axial chromatic aberration and astigmatism generated in the primary optical system. In regard to the relationship between the spacing between a plurality of primary electron beams and the secondary optical system, cross-talk between a plurality of detected electron beams can be reduced by increasing a minimum value of the spacing between the primary electron beams larger than the aberration in the secondary optical system.

Further, in the electron beam apparatus of FIG. 47, a switch (single-pole double-throw switch) 16-9, two memories (memory 0 and memory 1) 17-9, and a switch (double-pole single-throw switch) 18-9 are connected at the back of each signal path comprised of the secondary electron detector 13-9 and amplifier 14-9. Digital signals are supplied to a CPU 15-9 through these components. The plurality of switches 16-9 are simultaneously switched, and the plurality of switches 18-9 are simultaneously switched as well. Further, the two sets of these switches are simultaneously switched from the scanning states. Therefore, in the scanning states, while digital signals corresponding to i-th raster scanning are being stored in the memory 0, digital signals generated in (i−1)th raster scanning and stored in the memory 1 are transferred from the memory 1 to the CPU 15-9. At the time the i-th raster scanning terminates, the two sets of switches are switched to supply the CPU 15-9 with the signal generated in the i-th raster scanning and stored in the memory 0 for processing, and simultaneously with this, signals generated in the (i+1)th raster scanning are stored in the memory 1. Then, as the (i+1)th raster scanning terminates, the two sets of switches are inverted. As a result, signals corresponding to the intensities of the secondary electron beams can be transferred with high fidelity even if high speed scanning is performed at clock frequency in a range of 500 MHz to 1 GHz.

Figure 48:
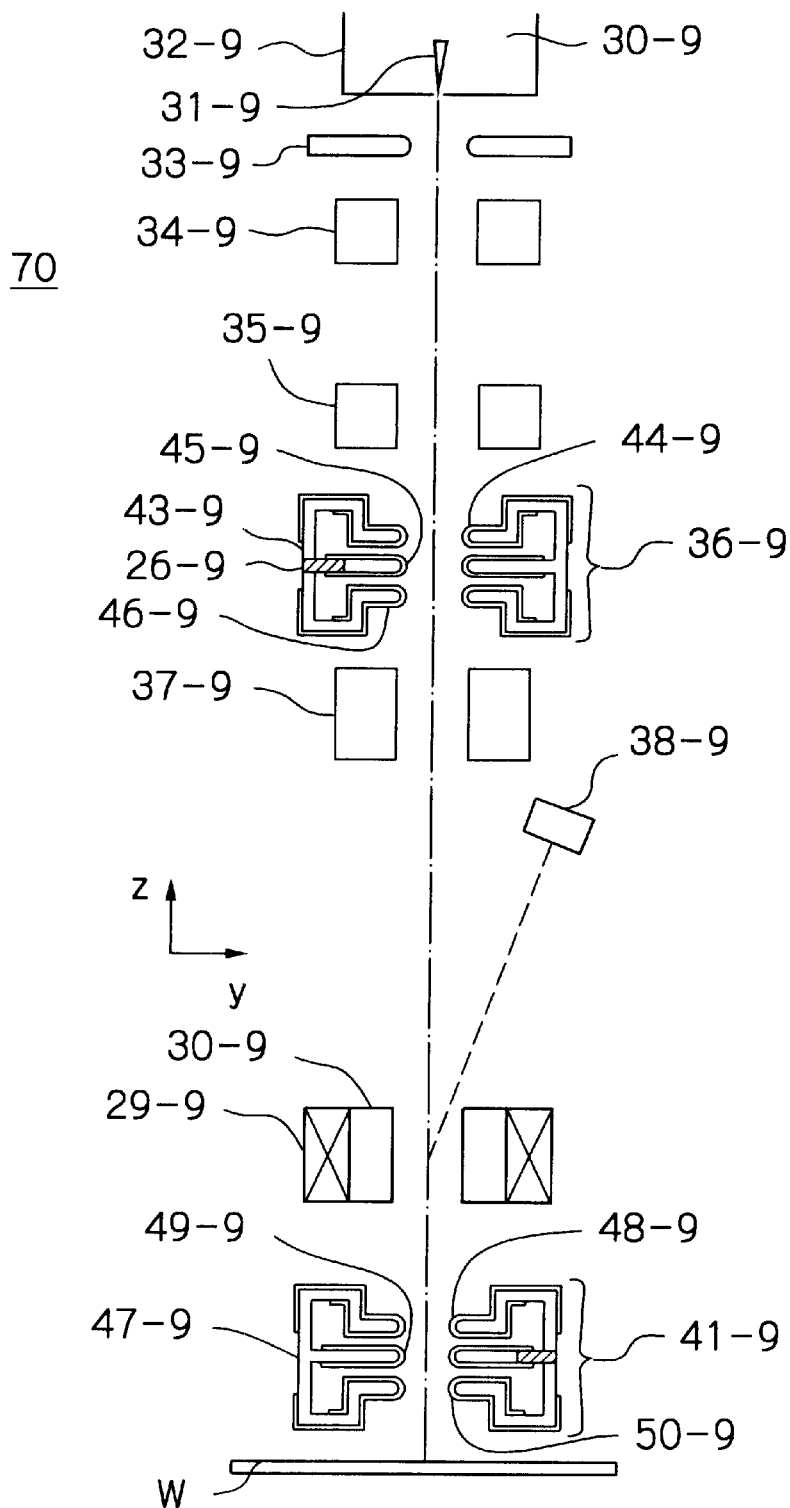
FIG. 48 schematically illustrates more further embodiment of an electron beam apparatus according to the present invention.

FIG. 48 illustrates another embodiment of the electro-optical system 70 which is applicable to the electron beam apparatus according to the present invention. This embodiment includes an electron gun 30-9 comprising electrodes, a cathode 31-9, a Wehnelt 32-9 and an anode 33-9; a primary optical system for focusing a primary electron beam emitted from the electron gun 30-9 on a wafer W; and a secondary optical system for guiding secondary electrons emitted from the wafer to a detector 38-9. In the primary optical system, the primary electron beam emitted from the electron gun 30-9 is aligned to a condenser lens 36-9 by alignment deflectors 34-9, 35-9, converged by the condenser lens 36-9, focused on the wafer by an objective lens 41-9, and deflected twice by an electrostatic deflector 37-9 and an electromagnetic deflector 29-9 to scan on the wafer.

Secondary electrons emitted from points on the wafer scanned by the primary electron beam are accelerated by a positive high voltage at a central electrode 49-9 of the objective lens 41-9, and narrowly converged to pass the objective lens. The secondary electrons passing through the objective lens 41-9 are deflected to the right in FIG. 51 by ExB separators 29-9, 40-9, and detected by the detector 38-9. In this event, while the condenser lens 36-9 and objective lens 41-9 are components which determine the dimension of the outer diameter of the optical system, the column of the electro-optical system 70 in this electron beam apparatus can have a smaller outer diameter by reducing the dimensions of outer diameters of these lenses 36-9, 41-9.

With a column having a smaller outer diameter, a plurality of such columns can be disposed on a single wafer, so that the wafer can be evaluated at a high throughput by the plurality of columns which simultaneously form images on the single wafer with a plurality of electron beams for evaluation.

Figure 49:
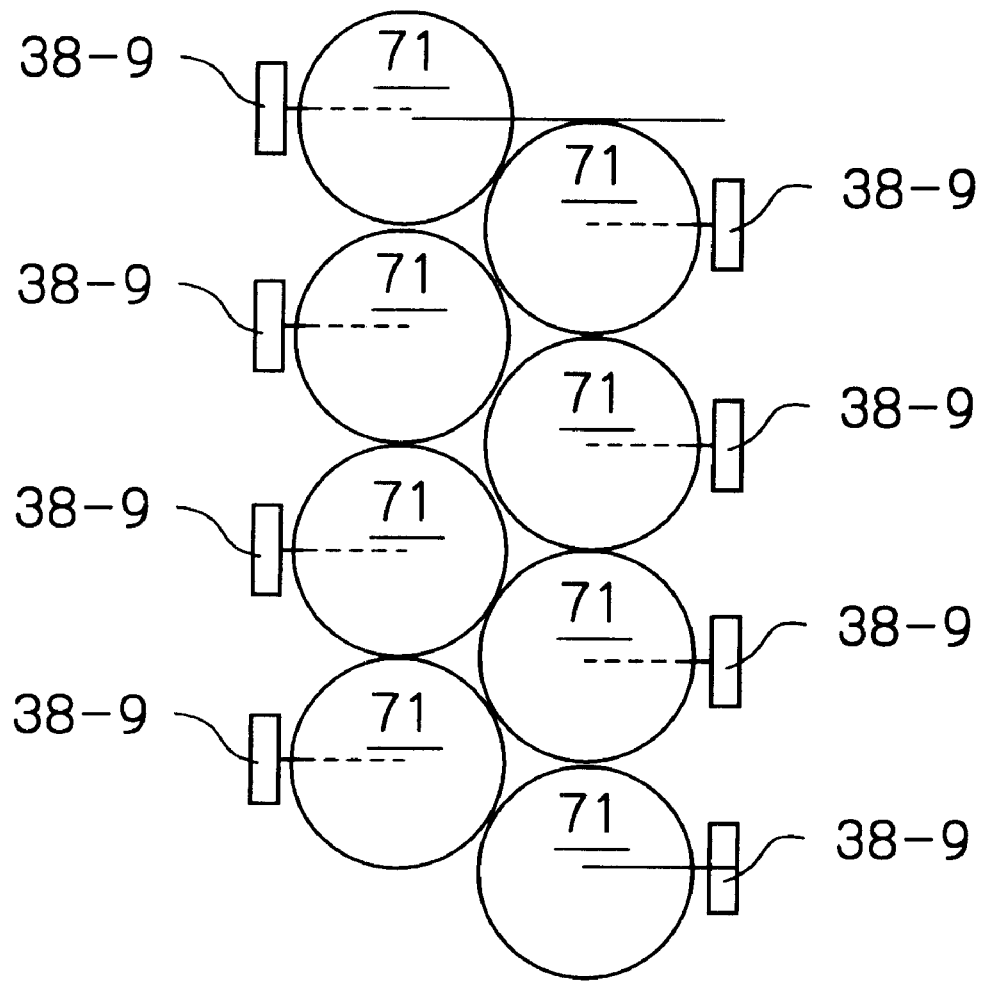
FIGS. 49–51 are drawing for respectively explaining embodiments in a case that a plurality of electron beam apparatuses are employed, according to the present invention.
Figure 50:
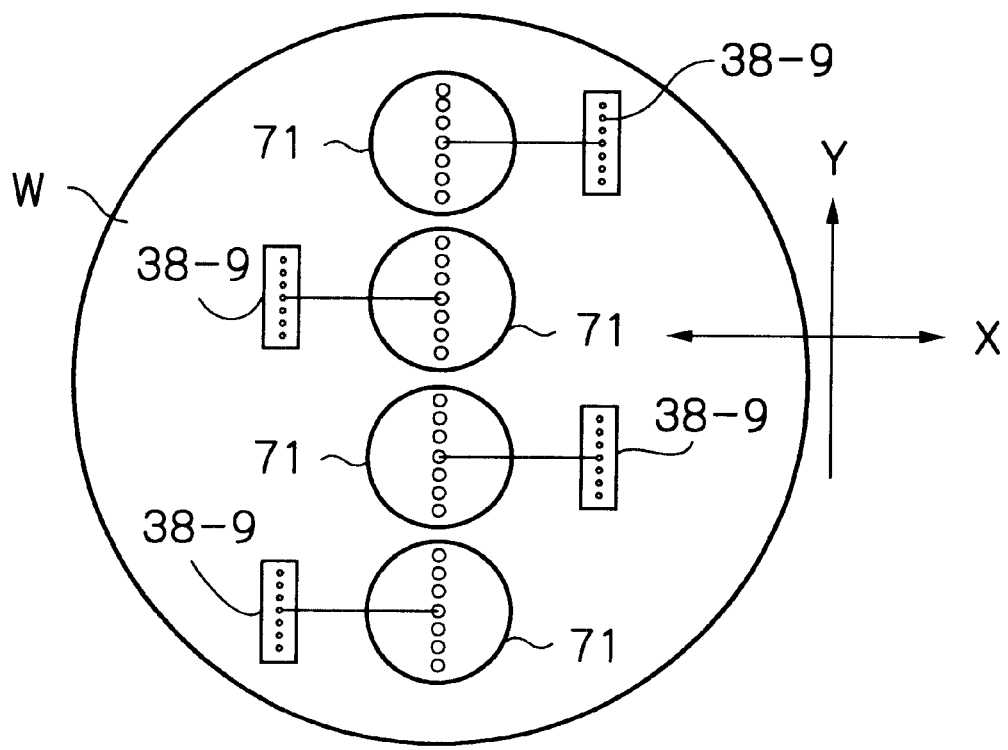
Figure 51:
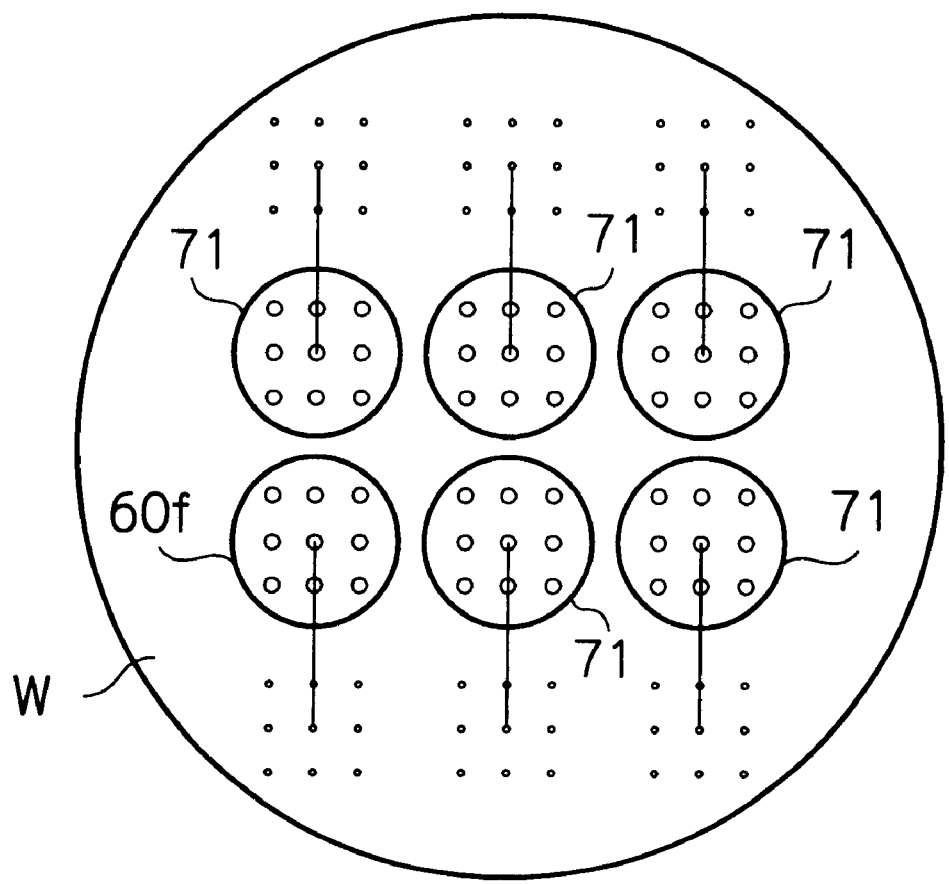

FIGS. 49 through 51 are explanatory diagrams for explaining embodiments of the electron beam apparatus according to the present invention when it is provided with a plurality of electro-optical systems.

In an embodiment illustrated in FIG. 49, columns 71 of stand-alone electro-optical systems are arranged in a matrix of four rows and two columns. This can be implemented by reducing the sizes of condenser lenses, objective lenses and the like to reduce the outer size of the column, and will be described for an electro-optical system illustrated in FIG. 48 taken as an example.

In the electro-optical system 70 illustrated in FIG. 48, a condenser lens 36-9 and an objective lens 41-9 are implemented as axially symmetric lenses. For reducing the outer dimensions of these lenses, the condenser lens 36-9 is manufactured by shaving an upper electrode 44-9, a central electrode 45-9 and a lower electrode 46-9 from an balk ceramics column 43-9, and coating a metal on the surface of the shaved ceramics. Similarly, the objective lens 41-9 is manufactured by shaving an upper electrode 48-9, a central electrode 49-9 and a lower electrode 50-9 from an integral ceramics column 47-9, and coating a metal on the surface of the shaved ceramics.

With the foregoing manufacturing method, the dimension of the outer diameter of each lens can be reduced to 40 mm φ or less, so that the columns 71 can be disposed on the surface of an 8-inch wafer in a matrix of four rows and two columns, as illustrated in FIG. 49. It has been found that platinum, which has a large work function, may be chosen as a metal material coated on the surface of the ceramics, whereby a high voltage can be applied across a small spacing between the electrodes. As a result, axial chromatic aberration can be reduced, and a large current can be generated with a beam of small dimension. For reference, in FIG. 48, a portion indicated by 26-9 is a voltage introducing terminal for applying a voltage to the central electrode 45-9 of the condenser lens 36-9. Also, in FIG. 49, 38-9 indicates the detector shown in FIG. 48.

A plurality of columns can be simultaneously disposed on a wafer for testing by taking the structure illustrated in FIG. 48 for the condenser lens and objective lens not only in the electro-optical system illustrated in FIG. 48 but also in any electro-optical system in an arbitrary embodiment previously described.

An embodiment illustrated in FIG. 50 shows an example in which four columns 71 of stand-alone electro-optical systems are arranged in a line, wherein a wafer W is irradiated with seven multi-beams in a line in each electro-optical system of the column 71. Therefore, the wafer can be scanned with 28 electron beams. For scanning the entire wafer, the wafer is moved sequentially in the X-axis direction and stepwisely in the Y-axis direction by a stage apparatus (not shown).

An embodiment illustrated in FIG. 51 shows an example in which six columns 71 of stand-alone electro-optical systems are arranged in a matrix of two rows and three columns, wherein a wafer W is irradiated with multi-beams in three rows and three columns in each electro-optical system of the column 71. Therefore, the wafer can be scanned simultaneously with 54 electron beams.

By thus disposing a plurality of electro-optical systems and providing multi-beams for irradiating the surface of the wafer and a plurality of detectors corresponding thereto in each optical system, the throughput (the amount of testing per unit time) can be largely improved for a test process.

Figure 52:
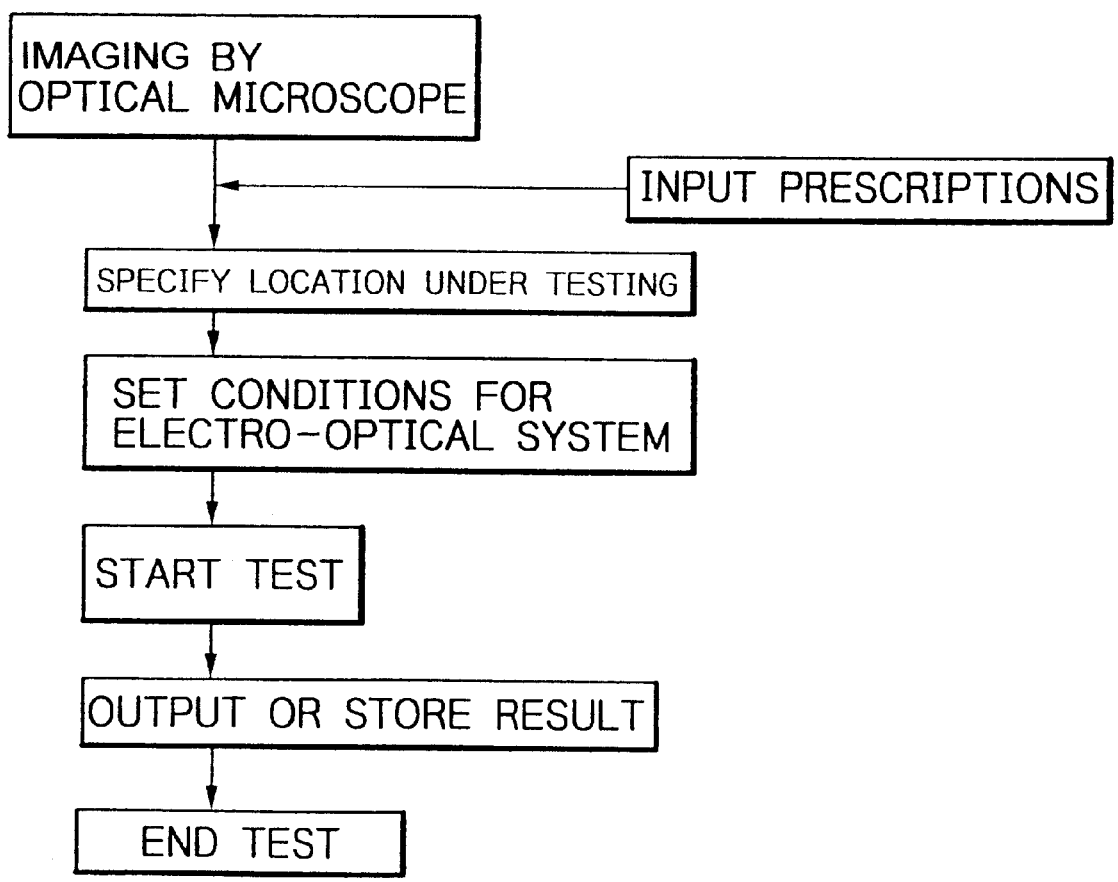
FIG. 52 is a flow chart depicting a method of evaluating according to the present invention.

As previously described in connection with FIG. 1, a wafer under testing, through an atmospheric conveyance system and a vacuum conveyance system, is aligned on a high precision XY stage, and then fixed by an electrostatic chuck mechanism or the like, followed by a defect test and the like in accordance with a procedure of FIG. 52. As illustrated in FIG. 52, first, an optical microscope is used to confirm the positions of respective dice and detect heights of respective locations as required, to store data. The optical microscope is also used to acquire optical microscopic images of sites at which defects and the like are preferably monitored for comparison with electron beam images, and the like. Next, the apparatus is applied with information on prescriptions in accordance with the type of wafer (after which process, whether the size of the wafer is 20 cm or 30 cm, and the like). Subsequently, after specifying locations to be tested, setting the electro-optical system, and setting testing conditions and the like, the wafer is tested for defects in real time while images are acquired. A high-speed information processing system comprising algorithms conducts the test through comparison of cells, comparison of dice and the like, and outputs the result of test to a CRT or the like, and stores the result in a storage device, as required. Defects include particle defects, abnormal shape (pattern defect), electric defects (disconnected wires, vias and the like, defective conduction, and the like), and the like. The information processing system is capable of automatically distinguishing such defects from one another, classifying the defects by size, and sorting out killer defects (grave defects which disable the use of a chip, and the like) in real time. The detection of electric defects can be achieved by detecting abnormal contrast. For example, irradiation of an electron beam (approximately 500 eV) to a defectively conducting location can result in distinction from normal locations because such location is generally charged in positive to cause lower contrast. An electron irradiating apparatus used herein refers typically to a low-potential energy electron beam generator (generation of thermal electron, UV/photoelectron) provided separately from an electron beam irradiating apparatus for testing in order to emphasize the contrast by potential difference. Before irradiating a region under testing with an electron beam for testing, this low-potential energy electron beam is generated for irradiation. For an image projection system which can positively charge an object under testing simply by irradiating the electron beam for testing, the low-potential electron beam generator need not be provided in separation depending on a particular use. Defects can also be detected from a difference in contrast (caused by a difference in the ease of flow in the forward direction and opposite direction of a device) by applying a wafer with a positive or negative potential with respect to a reference potential. This can be utilized in a line width measuring apparatus and an aligner.

As the electron beam apparatus operates, organic materials are deposited on a variety of electrodes used for forming and deflecting electron beams. Since insulating materials gradually deposited on surfaces in this manner adversely affect the formation of electron beams and the deflecting mechanism, the deposited insulating materials must be removed on a periodic basis. The periodic removal of insulating materials can be carried out by utilizing electrodes near regions on which insulating materials are deposited to create a plasma of hydrogen, oxygen or fluorine, and a compound including them, such as HF, $O_2$, $H_2O$, CMFM in vacuum, and removing only organic substances through oxidization, hydronization or fluorination.

Next, description will be made on a method of manufacturing semiconductor devices which includes a step for evaluating a semiconductor wafer in the middle of a process or after the process using the electron beam apparatus of the present invention.

Figure 53:
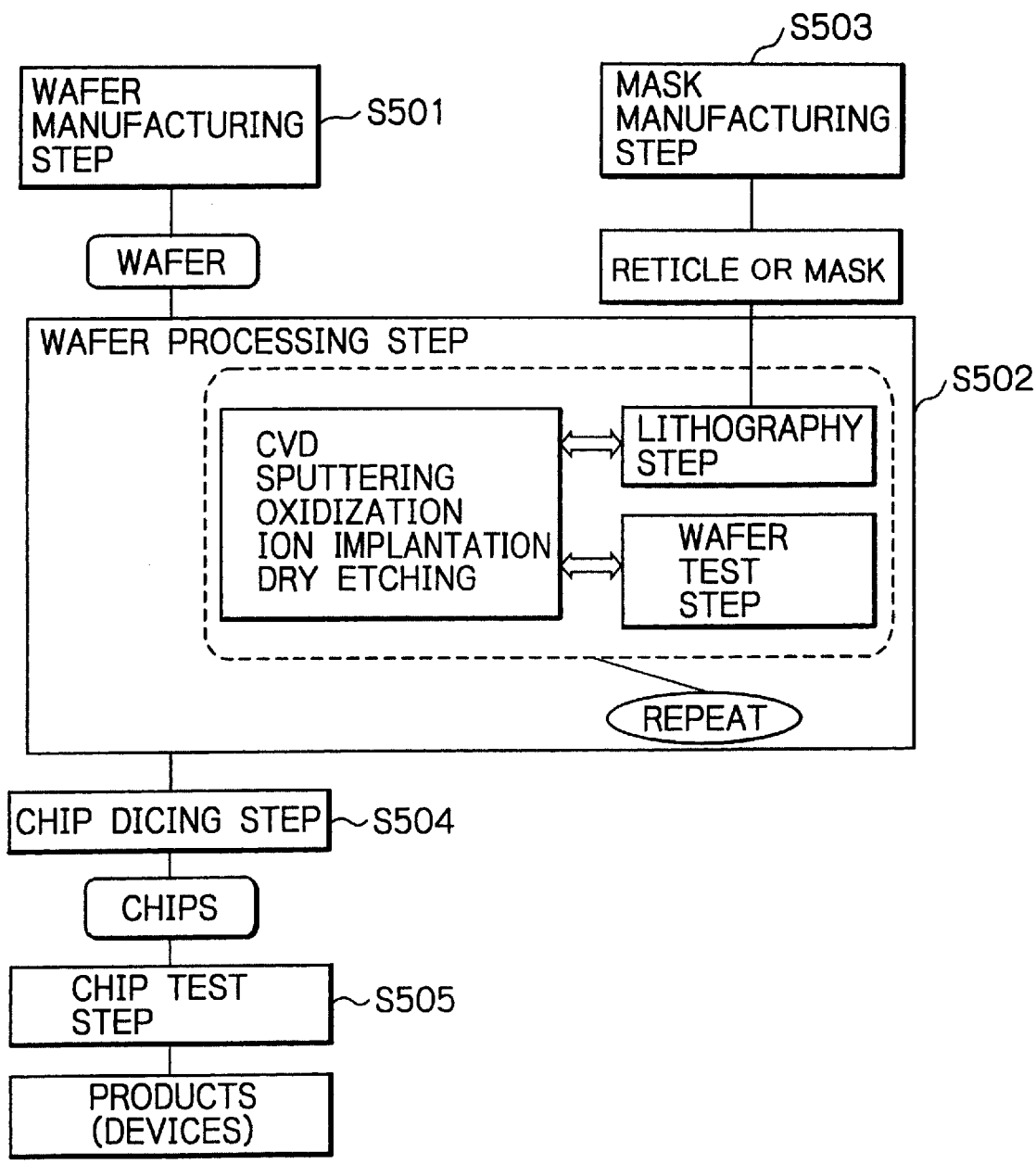
FIG. 53 is a flow chart depicting a method of fabricating semiconductor devices according to the present invention.

As illustrated in FIG. 53, the method of manufacturing semiconductor devices, when generally divided, comprises a wafer manufacturing step S501 for manufacturing wafers; a wafer processing step S502 for processing wafers as required; a mask manufacturing step S503 for manufacturing masks required for exposure; a chip assembly step S504 for dicing chips formed on a wafer one by one and bringing each chip into an operable state; and a chip testing step S505 for testing finished chips. Each of the steps may include several sub-steps.

In the respective steps, a step which exerts a critical influence to the manufacturing of semiconductor devices is the wafer processing step S502. This is because designed circuit patterns are formed on a wafer, and a multiplicity of chips which operate as a memory and MPU are formed in this step.

It is therefore important to evaluate a processed state of a wafer executed in sub-steps of the wafer processing steps which influences the manufacturing of semiconductor devices. Such sub-steps will be described below.

First, a dielectric thin film serving as an insulating layer is formed, and a metal thin film is formed for forming wires and electrodes. The thin films are formed by CVD, sputtering or the like. Next, the formed dielectric thin film and metal thin film, and a wafer substrate are oxidized, and a mask or a reticle created in the mask manufacturing step S503 is used to form a resist pattern in a lithography step. Then, the substrate is processed in accordance with the resist pattern by a dry etching technique or the like, followed by injection of ions and impurities. Subsequently, a resist layer is stripped off, and the wafer is tested.

The wafer processing step as described is repeated the number of times equal to the number of required layers to form a wafer before it is separated into chips in the chip assembly step S504.

Figure 54:
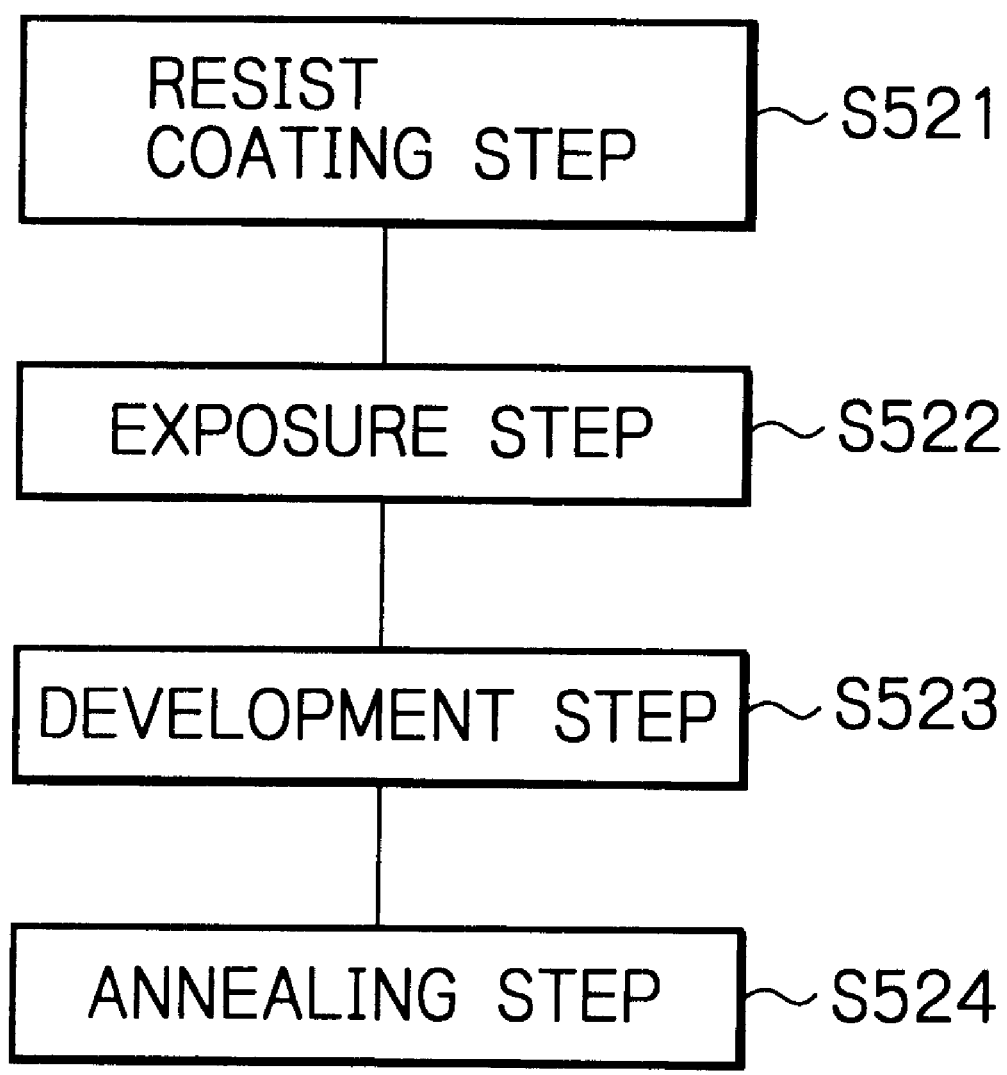
FIG. 54 is a flow chart depicting details of the lithography process indicated in FIG. 53.

FIG. 54 is a flow chart illustrating the lithography step which is a sub-step of the wafer processing step in FIG. 56. As illustrated in FIG. 57, the lithography step includes a resist coating step S521, an exposure step S522, a development step S523, and an annealing step S524.

After a resist is coated on a wafer formed with circuit patterns using CVD or sputtering in the resist coating step S521, the coated resist is exposed in the exposure step S522. Then, in the development step S523, the exposed resist is developed to create a resist pattern. In the annealing step S524, the developed resist pattern is annealed for stabilization. These steps S521 through S524 are repeated the number of times equal to the number of required layers.

In the process of manufacturing semiconductor devices, a test is conducted for defects and the like after the processing step which requires the test. However, the electron beam based defect testing apparatus is generally expensive and is low in throughput as compared with other processing apparatuses, so that the defect testing apparatus is preferably used after a critical step which is considered to most require the test (for example, etching, deposition, CMP (chemical mechanical polishing), planarization, and the like).

As described above, according to the present invention, since semiconductor devices are manufactured while they are tested for defects and the like after termination of each step, which requires the test, using a multi-beam based electron beam apparatus which presents a high throughput, the semiconductor devices themselves can be manufactured at a high throughput. It is therefore possible to improve the yield of products and prevent defective products from being shipped.

What is claimed is:

1. An electron beam apparatus for evaluating a sample surface, having a primary electro-optical system for irradiating a sample with primary electron beams, a detecting system, and a secondary electro-optical system for directing secondary electron beams emitted from the sample surface by the irradiation of the primary electron beams to the detecting system, the electron beam apparatus comprising:

a multi-beam generator included in the primary electro-optical system for arranging electrons emitted from an electron gun as a plurality of primary electron beams;

a scanning deflector included in the primary electro-optical system for simultaneously scanning the primary electron beams on the sample;

an objective lens included commonly in the primary electro-optical system and the secondary electro-optical system, for decelerating the primary electron beams to be irradiated to the sample, and for accelerating a plurality of secondary electron beams emitted from points of the sample irradiated with the primary electron beams;

a secondary electron beam separator included in the primary electro-optical system and the secondary electro-optical system, for deflecting the secondary electron beams passing through the objective lens from the primary electro-optical system to the secondary electro-optical system;

at least one stage of magnification lens included in the secondary electro-optical system, for magnifying the deflected secondary electron beams; and a plurality of detectors included in the detecting system and provided correspondingly to the secondary electron beams from the secondary electro-optical system, for detecting the secondary electron beams.

2. An electron beam apparatus according to claim 1, wherein:

the electron gun includes a plurality of electron sources each for emitting an electron beam;

the multi-beam generator comprises a first multi-aperture plate positioned between the electronic gun and the secondary electron beam separator and having a plurality of apertures for passing a plurality of electron beams from the electron sources therethrough to generate the primary electron beams; and the secondary optical system comprises a second multi-aperture plate positioned immediately in front of the detectors and having a plurality of apertures for leading the secondary electron beams to the detectors, the apertures corresponding one-to-one to the apertures of the first multi-aperture plate.

3. An electron beam apparatus according to claim 1, wherein:
the electron gun includes a single electron source;
the multi-beam generator comprises a first multi-aperture plate positioned between the electronic gun and the secondary electron beam separator and having a plurality of apertures for converting electrons from the single electron source to multi-beams as the primary electron beams; and
the secondary optical system comprises a second multi-aperture plate positioned immediately in front of the detectors and having a plurality of apertures for leading the secondary electron beams to the detectors, the apertures corresponding one-to-one to the apertures of the first multi-aperture plate.

4. An electron beam apparatus according to claim 2 or 3, wherein the first multi-aperture plate is formed in a curved shape or in a stepped shape so as to correct the field curvature for the primary electro-optical system.

5. An electron beam apparatus according to claim 2 or 3, wherein the plurality of apertures of the first and second multi-aperture plates are arranged in a linear fashion, or in a matrix of m rows and n columns.

6. An electron beam apparatus according to claim 2 or 3, wherein the apertures of the first multi-aperture plate are arranged substantially on the same circle about an optical axis of the primary electro-optical system at intervals, and arranged such that points projected on a line parallel with a direction in which the primary electron beams are scanned are spaced at equal intervals.

7. An electron beam apparatus according to claim 2, wherein:
the apertures of the first multi-aperture plate are arranged substantially on the same circle about an optical axis of the primary electro-optical system at intervals, and arranged such that points projected on a line parallel with a direction in which the primary electron beams are scanned are spaced at equal intervals, and
the primary optical system further comprises an electromagnetic lens positioned between the electronic gun and the sample for rotating the electron beams about the optical axis.

8. An electron beam apparatus according to claim 1, further comprising:
a plurality of amplifiers respectively provided at a back stage of the detectors in correspondence thereto; and
a device for individually adjusting gains or offsets for the amplifiers,
wherein the electron beams detected by the detectors can be corrected for non-uniformity.

9. An electron beam apparatus according to claim 2 or 3, further comprising:
a plurality of amplifiers respectively provided at a back stage of the detectors in correspondence thereto;
a device for measuring and monitoring the value of a current flowing through the first multi-aperture plate; and
a device for simultaneously adjusting gains and offsets of all the amplifiers based on measured current value, whereby the primary electron beams from the electron gun are corrected for temporal fluctuations in intensity.

10. An electron beam apparatus according to claim 9, further comprising a device for individually adjusting the gains or the offsets of the amplifiers, the device capable of correcting the amounts of electron beams detected by the detectors for non-uniformity.

11. An electron beam apparatus according to claim 1, wherein the primary electro-optical system further comprises at least two stages of lenses positioned between the electron gun and the objective lens for adjusting a magnification of a magnified image formed on an incident pupil of the objective lens, wherein a spacing and diameters of the primary electron beams can be adjusted by adjusting the lenses.

12. An electron beam apparatus according to claim 1, wherein the electron gun in the primary electro-optical system is a thermal field emission electron gun having an orientation in an optical axis direction thereof in <100> orientation, and configured to utilize an electron beam from <310> or <100> orientation on a side surface.

13. An electron beam apparatus according to claim 1, wherein spacing between the points on the sample irradiated with the primary electron beams is set larger than a value calculated by dividing a blurred enlarged image of the secondary electron beams on the detector by a magnification of the secondary optical system.

14. An electron beam apparatus according to claim 1, wherein:
the primary electro-optical system further comprises an aberration correcting device for correcting aberration of the primary electro-optical system, and
the aberration correcting device includes a combination of an electromagnetic lens and an electrostatic lens, a combination of an electromagnetic lens and an electrostatic deflector, or a combination of an electromagnetic lens and a lens for correcting astigmatism.

15. An electron beam apparatus according to claim 1, wherein:
the secondary electron beam separator is an ExB separator; and
the primary electro-optical system is further adapted such that an electro-magnetically deflected amount is double as much as an amount deflected by an electric field to cancel deflection chromatic aberration generated by the ExB separator for the primary electro-optical system.

16. An electron beam apparatus according to claim 1, wherein,
the apparatus further comprises an aligner for aligning a position on the sample to a point irradiated with the primary electron beam at the start of a test, and
the aligner utilizes a signal from an alignment mark on the sample as an alignment signal only when only one of the primary electron beams scans the alignment mark.

17. An electron beam apparatus according to claim 1, further comprising an irradiation energy adjusting device for adjusting irradiation energy of the primary electron beams to adjust a positionally fluctuating sample surface potential due to charge-up between a minimum amount required for observing an image and a maximum amount at which a distortion-free image is produced without damaging the sample.

18. An electron beam apparatus according to claim 2, wherein,
the apparatus further comprises an irradiation energy adjusting device for adjusting irradiation energy of the primary electron beams to adjust a positionally fluctuating sample surface potential due to charge-up between a minimum amount required for observing an image and a maximum amount at which a distortion-free image is produced without damaging the sample, and the irradiation energy adjusting device is configured to control a voltage applied to the electron sources to adjust the amount of electrons.

19. An electron beam apparatus according to claim 3, wherein, the apparatus further comprises an irradiation energy adjusting device for adjusting irradiation energy of the primary electron beams to adjust a positionally fluctuating sample surface potential due to charge-up between a minimum amount required for observing an image and a maximum amount at which a distortion-free image is produced without damaging the sample, the irradiation energy adjusting device is configured to control a voltage applied to an electron source in a time division manner.

20. An electron beam apparatus according to claim 1, wherein the apparatus is configured to optimize beam diameters of the primary electron beams at irradiated points on the sample to irradiate the sample with the primary electron beams having an optimal beam diameter which improves the S/N ratio.

21. An electron beam apparatus according to claim 20, wherein the beam diameter is set such that a ratio D/d of a minimum line width d of a pattern under testing of the sample to the beam diameter D of the primary electron beam is in a range of 0.95 to 1.25.

22. An electron beam apparatus according to claim 20, wherein the beam diameter is set such that a ratio D/d of a minimum line width d of a pattern under testing of the sample to the beam diameter D of the primary electron beam is in a range of 0.8 to 1.4.

23. An electron beam apparatus according to claim 20, wherein the beam diameter is set such that a ratio D/d of a minimum line width d of a pattern under testing of the sample to the beam diameter D of the primary electron beam is in a range of 0.66 to 1.5.

24. An electron beam apparatus according to claim 20, wherein the beam diameter is set such that a modulation transfer function MTF is in a range of 0.2 to 0.6 when scanning a periodic pattern having a pitch twice the minimum line width of the pattern under testing of the sample.

25. An electron beam apparatus according to claim 20, wherein the beam diameter is set such that a modulation transfer function MTF is in a range of 0.25 to 0.45 when scanning a periodic pattern having a pitch twice the minimum line width of the pattern under testing of the sample.

26. An electron beam apparatus according to claim 20, wherein:

in order to execute an evaluation mode of two or more line widths where the minimum line width of the pattern under testing of the sample is di (j=1, 2, . . . ), the beam diameter is set such that the beam diameter Di can be switched correspondingly to the minimum line width di and Di/di is in a range of 0.8 to 1.4.

27. An electron beam apparatus according to claim 1, wherein the apparatus is for use in a defect test, a line width measurement, an alignment accuracy measurement, or high time resolution voltage contrast measurement for a pattern of a semiconductor wafer which is the sample.

28. An electron beam apparatus according to claim 27, wherein the defect test includes a test for detecting short-circuiting between wires, and disconnected wires.

29. An electron beam apparatus according to claim 1, wherein, the apparatus further comprises an axially symmetric lens positioned between the sample and the objective lens, and the axially symmetric lens has axially symmetric electrodes forming a predetermined potential barrier to lead only secondary electron beams which go over the potential barrier to the secondary electron beam separator, depending on a potential possessed by the pattern on the sample.

30. An electron beam apparatus according to claim 1, wherein the lens included in the primary electro-optical system is comprised of axially symmetric lenses made of a ceramics material having surfaces coated with a metal.

31. An electron beam apparatus according to claim 1, wherein a plurality of the apparatuses are arranged in one or more columns, to test a single sample.

32. An electron beam apparatus according to claim 1, wherein, the apparatus further comprises an electron beam scanning controller, and the electron beam scanning controller is adapted to control such that the primary electron beams irradiate and scan, one by one, respective small region units divided from a region under measurement of the sample, and after completion of the scanning of a small region unit, do not scan a small region unit adjacent thereto by skipping at least the adjacent small region unit.

33. An electron beam apparatus according to claim 1, wherein, the apparatus further comprises an electron beam scanning controller, and the electron beam scanning controller is adapted to control such that the primary electron beams irradiate and scan, one by one, respective small region units divided from a region under measurement of the sample, and when executing the scanning of one small region unit, they start irradiating from a side near a small region unit which is to be next irradiated, and complete the irradiation on a far side.

34. An electron beam apparatus according to claim 1, wherein, the apparatus further comprises an electron beam scanning controller, and the electron beam scanning controller is adapted to control such that the primary electron beams irradiate and scan, one by one, respective small region units divided from a region under measurement of the sample, and during executing the scanning of one small region unit, they irradiate and scan to skip one or more scanning lines, and subsequently irradiate and scan the skipped scanning line.

35. An electron beam apparatus according to claim 1, further comprising a stage apparatus for carrying the sample thereon, the stage apparatus comprising:

a non-contact supporting mechanism based on a hydrostatic bearing, and a vacuum sealing mechanism based on differential exhaustion; and a partition positioned between a location on the sample surface irradiated with the primary electron beam and the hydrostatic bearing support of the stage apparatus for reducing conductance, whereby a pressure difference is produced between an electron beam irradiated region and the hydrostatic bearing support.

36. An electron beam apparatus according to claim 35, wherein the partition contains a differential pumping structure.

37. An electron beam apparatus according to claim 35, wherein the partition has a cold trap function.

38. An electron beam apparatus according to claim 35, wherein two of the partitions are provided in the vicinity of an electron beam irradiated position and in the vicinity of the hydrostatic bearing.

39. An electron beam apparatus according to claim 35, wherein a gas supplied to the hydrostatic bearing of the stage apparatus is dry nitrogen or highly pure inert gas.

40. An electron beam apparatus according to claim 35, wherein at least surfaces of parts of the stage apparatus facing the hydrostatic bearing are subjected to a surface treatment for reducing an emitted gas.

41. An electron beam apparatus according to claim 1, wherein,
the stage apparatus for carrying the sample thereon is accommodated in a housing and supported by the hydrostatic bearing with respect to the housing in a non-contact manner;
the housing for accommodating the stage apparatus is evacuated; and
the electron beam apparatus further comprises a differential pumping mechanism provided around a portion of the electron beam apparatus for irradiating the sample surface with the primary electron beams for evacuating the irradiated region on the sample surface.

42. An electron beam apparatus according to claim 41, wherein a gas supplied to the hydrostatic bearing of the X-Y stage is dry nitrogen or highly pure inert gas, the dry nitrogen or the highly pure inert gas being exhausted from the housing for accommodating the stage apparatus, pressurized, and again supplied to the hydrostatic bearing.

43. An evaluation system for testing a sample, comprising:
an electron beam apparatus according to claim 1;
a working chamber for accommodating a stage apparatus and a primary electron beam irradiating unit of the electron beam apparatus, the working chamber being controllable in a vacuum atmosphere;
a loader for supplying a sample onto the stage apparatus within the working chamber;
a potential applying mechanism disposed within the working chamber for applying the sample with a potential; and
an alignment controller for studying a surface of the sample to control alignment for positioning the sample with respect to an electro-optical system of the electron beam apparatus,
wherein the vacuum working chamber is supported through a vibration isolator for isolating vibrations from a floor.

44. An evaluation system according to claim 43, wherein:
the loader comprises a first loading chamber and a second loading chamber which are atmospherically controllable independently of each other, a first conveyer unit for conveying a sample between the inside and the outside of the first loading chamber, and a second conveyer unit provided for the second loading chamber for conveying a sample between the inside of the first loading chamber to the stage apparatus, and
the evaluation system further comprises an mini-environment space partitioned for supplying a sample to the loader.

45. An evaluation system according to claim 43, further comprising a laser interference measuring device for detecting coordinates of a sample under testing on the stage apparatus, wherein the alignment controller determines the coordinates of the sample under testing making use of a pattern which exists on the sample.

46. An evaluation system according to claim 44, wherein positioning of the sample includes rough positioning performed in the mini-environment space, and positioning in a X-Y axis direction and positioning in a rotating direction performed on the stage apparatus.

47. A method of manufacturing semiconductor devices, the method comprising a step of evaluating which is executed using an electron beam apparatus according to claim 1 for evaluation such as a defect test for semiconductor devices in the middle of or after termination of a manufacturing process.

48. A method of manufacturing semiconductor devices, the method comprising a step of evaluating which is executed using an evaluation system according to claim 43 for evaluation such as a defect test for semiconductor devices.

49. A method of evaluating a sample surface using an electron beam apparatus having a primary electro-optical system for irradiating a sample with primary electron beams, a detecting system, and a secondary electro-optical system for directing secondary electron beams emitted from the sample surface by the irradiation of the primary electron beams to the detecting system, the method comprising:
arranging electrons emitted from an electron gun as a plurality of primary electron beams;
simultaneously scanning the sample with the primary electron beams;
decelerating the primary electron beams and irradiating them to the sample through an objective lens included commonly in the primary electro-optical system and the secondary electro-optical system;
accelerating, by the objective lens, a plurality of secondary electron beams emitted from points of the sample irradiated with the primary electron beams;
deflecting the secondary electron beams passing through the objective lens from the primary electro-optical system to the secondary electro-optical system;
magnifying the deflected secondary electron beams by at least one magnification lens, and leading the secondary electron beams to a plurality of detectors provided correspondingly thereto; and
detecting the secondary electron beams from the secondary electro-optical system by the detectors provided correspondingly thereto.

50. A sample evaluation method according to claim 49, wherein:
the step of arranging the electrons includes steps of rotating the primary electron beams about an optical axis by a magnetic lens positioned between an electron gun and the sample, and converting the primary electron beams to multi-beams through a plurality of apertures of a first multi-aperture plate; and
the step of leading the secondary electron beams includes leading the secondary electron beams magnified by the magnification lens to the detectors through a plurality of apertures of a second multi-aperture plate.

51. A sample evaluation method according to claim 49, further comprising the steps of:
amplifying by a plurality of amplifiers provided at a stage behind the detectors in correspondence thereto; and
individually adjusting gains or offsets of the amplifiers, whereby the amounts of electron beams detected by the detectors can be corrected for non-uniformity.

52. A sample evaluation method according to claim 49, further comprising the step of adjusting a magnification of an enlarged image formed on an incident pupil of the objective lens, thereby a spacing and a beam diameter of the primary electron beams being adjustable.

53. A sample evaluation method according to claim 49, wherein:

the step of deflecting the secondary electron beam is executed by an ExB separator, and the sample evaluation method further comprises the step of setting the ExB separator such that an electromagnetically deflected amount is double as much as an amount deflected by an electric field to cancel deflection chromatic aberration generated by the ExB separator for the primary electro-optical system.

54. A sample evaluation method according to claim 49, further comprising a step of optimizing a beam diameter of the primary electron beams at irradiated points on the sample to improve the S/N ratio.

55. A sample evaluation method according to claim 54, wherein beam diameter is set such that a modulation transfer function MTF is in a range of 0.2 to 0.6 when scanning a periodic pattern having a pitch twice the minimum line width of the pattern of the sample under testing.

56. A sample evaluation method according to claim 49, wherein the lens included in the primary electro-optical system is comprised of axially symmetric lenses made of a ceramics material having surfaces coated with a metal.

57. A sample evaluation method according to claim 49, wherein the step of scanning is executed such that the primary electron beams irradiate and scan, one by one, respective small region units divided from a region under measurement of the sample, and after completion of the scanning of a small region unit, skip at least an adjacent small region unit, and then irradiate and scan a non-irradiated small region unit.

58. A sample evaluation method according to claim 49, wherein the step of scanning is executed such that the primary electron beams irradiate and scan, one by one, respective small region units divided from a region under measurement of the sample, and when executing the scanning of one small region unit, they start irradiating from a side near a small region unit which is to be next irradiated, and complete the irradiation on a far side.

59. A sample evaluation method according to claim 49, further comprising:

supporting a stage apparatus for carrying the sample thereon in a housing by a hydrostatic bearing in a non-contact manner;

evacuating the housing containing the stage apparatus; and exhausting the irradiated region on the sample surface by a differential pumping mechanism provided around a portion of the electron beam apparatus for irradiating the sample surface with the primary electron beams.

60. A sample evaluation method according to claim 59, wherein the step of supporting includes the step of supplying the hydrostatic bearing of the stage apparatus with dry nitrogen or highly pure inert gas, wherein the dry nitrogen or the highly pure inert gas is evacuated from the housing for accommodating the stage apparatus, pressurized, and again supplied to the hydrostatic bearing.

* * * * *